(12) United States Patent
Lampe et al.

(10) Patent No.: US 8,835,457 B2
(45) Date of Patent: Sep. 16, 2014

(54) BRIDGED BICYCLIC RHO KINASE INHIBITOR COMPOUNDS, COMPOSITIONS AND USE

(71) Applicants: John W. Lampe, Cary, NC (US); Paul S. Watson, Carrboro, NC (US); David J. Slade, Claremont, CA (US)

(72) Inventors: John W. Lampe, Cary, NC (US); Paul S. Watson, Carrboro, NC (US); David J. Slade, Claremont, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/918,020

(22) Filed: Jun. 14, 2013

(65) Prior Publication Data

US 2013/0281485 A1 Oct. 24, 2013

Related U.S. Application Data

(62) Division of application No. 12/965,615, filed on Dec. 10, 2010, now Pat. No. 8,476,295.

(60) Provisional application No. 61/286,291, filed on Dec. 14, 2009.

(51) Int. Cl.
*C07D 451/04* (2006.01)
*C07D 401/12* (2006.01)

(52) U.S. Cl.
USPC ............ 514/304; 514/310; 546/126; 546/143

(58) Field of Classification Search
USPC ............................ 546/126, 143; 514/304, 310
See application file for complete search history.

(56) References Cited

U.S. PATENT DOCUMENTS

| 6,909,000 B2 | 6/2005 | Farmer et al. |
| 7,491,722 B2 * | 2/2009 | Dal Piaz et al. .......... 514/252.01 |
| 8,071,779 B2 | 12/2011 | Lampe et al. |
| 2002/0091115 A1 | 7/2002 | Dyatkin et al. |
| 2009/0253687 A1 | 10/2009 | Fukumoto et al. |

FOREIGN PATENT DOCUMENTS

WO 2009108838 9/2009

OTHER PUBLICATIONS

International Search Report mailed Feb. 9, 2011 for PCT/US2010/059926.

* cited by examiner

*Primary Examiner* — Niloofar Rahmani
(74) *Attorney, Agent, or Firm* — Yong Zhao; Laura Ginkel

(57) ABSTRACT

The present invention is directed to synthetic bridged bicyclic compounds that are inhibitors of rho-associated protein kinase. The present invention is also directed to pharmaceutical compositions comprising such compounds and a pharmaceutically acceptable carrier. The invention is additionally directed to a method of preventing or treating diseases or conditions associated with cytoskeletal reorganization. The method comprises administering to a subject a therapeutically effective amount of a Rho kinase inhibitory compound of Formula I, wherein said amount is effective to influence the actomyosin interactions, for example, by leading to cellular relaxation and alterations in cell-substratum adhesions. In one embodiment, the method treats increased intraocular pressure, such as primary open-angle glaucoma. In another embodiment, the method treats diseases or conditions of the lung associated with excessive cell proliferation, remodeling, inflammation, vasoconstriction, bronchoconstriction, airway hyperreactivity and edema.

13 Claims, No Drawings

BRIDGED BICYCLIC RHO KINASE INHIBITOR COMPOUNDS, COMPOSITIONS AND USE

CROSS REFERENCE TO RELATED APPLICATION

This is a divisional application of U.S. Ser. No. 12/965,615, filed on Dec. 20, 1010, which claims priority from U.S. Ser. No. 61/286,291, filed on Dec. 14, 2009.

TECHNICAL FIELD

This invention relates to synthetic bridged bicyclic rho-associated kinase (RHO KINASE) inhibiting compounds. The invention also relates to using such compounds in the prevention or treatment of diseases or disorders that are affected or can be assisted by altering the integrity or rearrangement of the cytoskeleton, including but not limited to actomyosin interactions, tight junctional and focal adhesion complexes, such as ophthalmic and pulmonary diseases or conditions associated with inflammation, excessive cell proliferation, remodeling, neuritis retraction, corneal neurodegeneration, vasoconstriction, bronchoconstriction, airway hyperreactivity, excessive vaso-permeability and edema. This invention relates to methods for preventing or treating ophthalmic disorders including allergic conjunctivitis, corneal hyposensitivity and kerotopathy, dry eye disease, proliferative vitreal retinopathy, macular edema and degeneration, blepharitis, and disorders in which intraocular pressure is elevated, such as primary open-angle glaucoma. This invention also relates to methods of preventing or treating pulmonary diseases such as asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP, using novel Rho kinase inhibitor compounds.

BACKGROUND OF THE INVENTION

Rho Kinase as a Target

The Rho family of small GTP binding proteins can be activated by several extracellular stimuli such as growth factors, hormones and mechanic stress and function as a molecular signaling switch by cycling between an inactive GDP-bound form and an active GTP-bound form to elicit cellular responses. Rho kinase (RHO KINASE) functions as a key downstream mediator of Rho and exists as two isoforms (RHO KINASE1 and RHO KINASE2) that are ubiquitously expressed. RHO KINASES are serine/threonine kinases that regulate the function of a number of substrates including cytoskeletal proteins such as adducin, moesin, $Na^+$—$H^+$ exchanger 1 (NHE1), LIM-kinase and vimentin, contractile proteins such as the myosin light chain phosphatase binding subunit (MYPT-1), CPI-17, myosin light chain and calponin, microtubule associated proteins such as Tau and MAP-2, neuronal growth cone associate proteins such as CRMP-2, signaling proteins such as PTEN and transcription factors such as serum response factor (Loirand et al, Circ Res 98:322-334 (2006)). RHO KINASE is also required for cellular transformation induced by RhoA. As a key intermediary of multiple signaling pathways, RHO KINASE regulates a diverse array of cellular phenomena including cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. As a result of these cellular actions, RHO KINASE regulates physiologic processes such as vasoconstriction, tissue remodeling, inflammation, edema, proliferative disorders, neurite extension/retraction, and neurodegeneration.

The use of prototype non-potent Rho-kinase inhibitors, Y27632 or fasudil, in animal models has suggested a number of potential benefits of Rho-kinase inhibitors. Y27632 has shown favorable activity in animal models of respiratory disorders such as airway hyperreactivity and asthma (Schaafsma et al. *Respiratory Research* 7:121-127, 2006), airway remodeling and idiopathic pulmonary fibrosis (Shimizu et al. *Am J Respir Crit. Care Med* 163:210-217, 2001) and RSV infection (Hashimoto et al. *Thorax* 57:524-527, 2002). Fasudil has been shown to have favorable activity in models of asthma (Taki F et al. *Clin Exp Allergy,* 37:599-607, 2007); pulmonary hypertension (Shimokawa et al. *Arterioscler Thromb Vasc Biol* 25:1767-1775, 2005).

Glaucoma

Glaucoma is an ophthalmic disease that leads to irreversible visual impairment. It is the fourth most common cause of blindness and the second most common cause of vision loss in the United States, and the most common cause of irreversible vision loss among African-Americans. Generally speaking, the disease is characterized by a progressive optic neuropathy caused at least in part by deleterious effects resulting from increased intraocular pressure. In normal individuals, intraocular pressures range from 12 to 20 mm Hg, averaging approximately 16 mm Hg. However, in individuals suffering from primary open angle glaucoma, intraocular pressures generally rise above 22 to 30 mm Hg. In angle closure or acute glaucoma intraocular pressure can reach as high as 70 mm Hg leading to blindness within only a few days. Interestingly, the loss of vision can result from statistically normal intraocular pressures in individuals with unusually pressure-sensitive eyes; a condition known as normotensive glaucoma. [See, e.g., P. L. Kaufman and T. W. Mittag, "Medical Therapy Of Glaucoma," Ch. 9, Sec. II (pp. 9.7-9.30) In P. L. Kaufman and T. W. Mittag (eds.): Glaucoma (Vol. 7 of S. M. Podos and M. Yanoff (eds): Textbook of Ophthalmology Series). London, Mosby-Year Book Europe Ltd. (1994); A. C. Guyton, Textbook of Medical Physiology (W. B. Saunders Co., Sixth Ed.), pp. 386-89 (1981)].

Open-angle glaucoma constitutes approximately 90% of all primary glaucomas and is characterized by abnormally high resistance to fluid (aqueous humor) drainage from the eye. Normal resistance is required to maintain an intraocular pressure sufficient to maintain the shape of the eye for optical integrity. This resistance is provided by the trabecular meshwork, a complex, multilaminar tissue consisting of specialized cells with a dense actomyosin cytoskeletal network, collagenous beams and extracellular matrix. The resistance of the trabecular meshwork normally is such that intraocular pressure is ~16 mm Hg, a pressure at which aqueous humor leaves the eye at the same rate at which it is produced (2.5 μL/minute). In the glaucomatous eye, the rate of aqueous humor production remains constant, while it is the increased resistance to outflow that is responsible for the elevated intraocular pressure.

Typical treatments for glaucoma comprise a variety of pharmaceutical approaches for reducing intraocular pressure (TOP), each with their drawbacks. Beta-blockers and carbonic anhydrase inhibitors reduce aqueous humor production, which is needed to nourish the avascular lens and corneal endothelial cells, and the prostaglandins affect the uvealscleral outflow pathway, which only accounts for 10% of the total outflow facility. There are currently no commercially approved therapeutic agents which act directly upon the trabecular meshwork, the site of aqueous humor drainage where increased resistance to aqueous humor outflow is responsible for elevated IOP. Therefore, a medical need remains for improved IOP-lowering medications that target this structure. Pharmacological agents which target the trabecular meshwork may provide relief to the significant numbers of patients that do not respond adequately to current IOP-lowering medications and/or cannot tolerate the side effects associated with these agents. Additionally, these molecules may prove beneficial as adjunctive therapy in combination with other classes of IOP-lowering medications.

U.S. Pat. Nos. 6,586,425, 6,110,912, and 5,798,380 disclose a method for the treatment of glaucoma using compounds that affect the actin filament integrity of the eye to enhance aqueous humor outflow. These patents also specifically disclose kinase inhibitors as well as latrunculin-A, latrunculin-B, swinholide-A, and jasplakinolide, which cause a perturbation of the actin cytoskeleton and tight junctional complexes in the trabecular meshwork or the modulation of its interactions with the underlying membrane. Perturbation of the cytoskeleton and the associated adhesions reduces the resistance of aqueous humor flow through the trabecular meshwork and thereby reduces intraocular pressure.

Wound healing is another approach in which these classes of molecules can aid in modulating IOP. Trabeculectomy is the most common form of glaucoma filtration surgery and remains as the first-line therapy for surgical reduction of pharmacologically uncontrolled intraocular pressure in primary open angle glaucoma. This procedure establishes a limbal fistula through which aqueous humor drains into the subconjunctival space establishing a filtering bleb to lower intraocular pressure. The success of the procedure is highly dependent on pharmacological modulation/inhibition of wound healing.

A major advance in the surgical management of glaucoma has been the use of antimetabolites to prevent scarring after glaucoma filtration surgery. Postoperative scarring of the filtering bleb is the most crucial factor in determining the short and long-term outcome of modern glaucoma filtration surgery. The antimetabolites mitomycin C (MMC) and 5-fluorouracil (5-FU) are widely used to suppress scarring and thus failure of the filtering bleb. In a large retrospective study, conventionally performed trabeculectomy has shown a failure rate of up to 30% within 3 months after surgery. To lower the incidence of this detrimental complication, various methods have been investigated in order to avoid scarring of the filtering bleb, mostly dealing with the intraoperative or postoperative application of antimetabolic drugs Despite their positive long-term effect on prolonged filtration, the application of cytotoxic drugs to a surgically opened eye increases the incidence of severe complications such as concomitant increases in vision threatening complications. MMC exhibits a high incidence of severe post-application complications, as does 5-FU; although its side effects mainly affect the corneal epithelium its clinical use is limited by severe pain and discomfort to the patient. No sufficient method has been established to achieve satisfying postoperative long-term surgical results with only minimal or no side effects for the patient.

Allergic Conjunctivitis

Allergic eye disease primarily affects the conjunctiva. The signs and symptoms include itching, tearing, conjunctival edema, hyperemia, watery discharge, burning, and photophobia. Symptoms are usually bilateral; however, one eye can be affected more than the other. The most common allergic eye disease, allergic conjunctivitis (AC) can be subdivided into acute, seasonal and perennial. All three types result from classic Type I IgE-mediated hypersensitivity (Abelson, M B., et. al. *Surv Ophthalmol;* 38(S):115, 1993).

Two phases of the ocular allergic response have been indentified. The immediate response to allergens is mediated predominantly by mast cells, which are present in high concentrations in the normal conjunctiva, and increase further in patients with AC (Tsubota, K, et al., *Cornea,* 10:525, 1991). Mast cells become activated when allergen-IgE cross linking occurs, and chemical mediators are released by exocytosis. Histamine, the main mediator of the early response, causes vasodilatation, vasopermeability, and itching. Mast cells also release a variety of cytokines and chemokines, resulting in the influx of other inflammatory cells and continued inflammation, representing the late phase of the allergic reaction. Eosinophils, basophils, and neutrophils appear 6 to 10 hours after allergen challenge, followed by lymphocytes and monocytes.

Allergic conjunctivitis is a relatively benign ocular disease of young adults (average age of onset of 20 years of age) that causes significant suffering and use of healthcare resources, although it does not threaten vision. Ocular allergy is estimated to affect 20 percent of the population on an annual basis, and the incidence is increasing (Abelson, M B et. al., *Sury Ophthalmol.,* 38(S):115, 1993). AC impacts productivity and while there are a variety of agents available for the treatment of AC, numerous patients still lack good control of symptoms and some are tolerating undesired side effects. Surveys have shown 20% of patients with AC are not fully satisfied with their AC medications and almost 50% feel they receive insufficient attention from their physicians (Mahr, et al., *Allergy Asthma Proc,* 28(4):404-9, 2007).

Corneal Hyposensitivity and Neurodegeneration

An undesirable effect following laser photorefractive keratectomy (PRK), laser-assisted-in-situ keratomileusis (LASIK), and keratoplasty, is a functional reduction of corneal sensitivity, which occurs from approximately 3 weeks to one year and is due to severing of the corneal nerves during surgery. For example, it has been reported that the corneal nerve is apparently severed after LASIK (Tuuli U, et al., *Experimental Eye Research* 66: 755-763, 1998), and the corneal sensitivity decreases in a corneal region where, after LASIK, neurogram is not observed or the nerve bundle is too short to create connection (Tuuli U, et al., *Investigative Ophthalmology & Visual Sciences,* 41: 393-397, 2000). It has been demonstrated that the corneal hyposensitivity after PRK and LASIK causes lower lacrimal gland response and decreased lacrimal fluid (Ang R T, et al., *Current Opinion in Ophthalmology* 12: 318-322, 2001). As a result of the hypofunction of corneal sensitivity, patients after a corneal surgery blink less number of times, problematically showing the symptoms of dry eye. Additionally, in the patients with dry eye, lacrimal hypofunction gives rise to corneal hyposensitivity, which, upon combination with further lacrimal hypofunction, problematically aggravates the sensory component of the corneal surface. At present, recovery of corneal hyposensitivity following corneal surgery is left to spontaneous recovery, and in the treatment of dry eye, no active treatment is provided to recover corneal sensitivity. Moreover, while corneal hyposensitivity is caused by the diseases accompanying corneal neurodegeneration, such as neuroparalytic keratopathy, corneal ulcer, diabetic keratopathy and the like, no appropriate treatment is available at present.

Corneal hyposensitivity is caused by the diseases accompanying corneal neurodegeneration, such as neuroparalytic keratopathy, corneal ulcer, diabetic keratopathy and the like.

Rho is a low molecular weight G protein included in the Rho family (containing Rho, Rac, Cdc42, etc.), and is known to be involved in actin cytoskeleton organization and neurite retraction reaction. C3 enzyme, a Rho protein inhibitor, is known to extend cell protrusion of 3T3 fibroblast (Hirose, M. et al., The Journal of Cell Biology, 141: 1625-1636, 1998), and a method of promoting the growth of central nerve axon by the administration of an effective amount of Rho protein inhibitor to patients is disclosed (JP-T-2001-515018 and EP-1,011,330-A). In addition, a Rho kinase inhibitor, which is among the effector molecules of Rho protein, is known to have an axon extension action of retinal ganglion cells, and exhibit a regeneration promoting action on the optic nerve cell (WO 02/83175 and EP-1,142,585-A). WO 03/020281 teaches that a compound capable of promoting nerve regeneration or neurite extension can be used for the treatment of a disease state caused by a corneal nerve disorder after surgery such as LASIK and the like. As to the trigeminal nerve, it has been reported that, in a rat trigeminal nerve tissue culture (trigeminal tract in whole mount cultures) system, extension of neurotrophin-induced nerve axon of nerve growth factor (NGF) and the like is inhibited by a Rho activator (lysophosphatidic acid), and facilitated by introduction of dominant negative Rho into a cell (Ozdinler, P. Hande et al., The Journal of Comparative Neurology, 438:377-387, 2001).

Dry Eye

There are many ocular conditions where it is therapeutically desirable to correct improper tear fluid production. Dry eye is the general term for disease abnormalities that impact the pre-corneal tear film leading to a loss of mucous-containing goblet cells of the conjunctiva and eventually desquamation of the corneal epithelium that leads to destabilization of the cornea-tear interface (Gilbard J et al. *CLAO Journal* 22(2), 141-45 (1996)). There are several main structures responsible for maintaining the properties of the tear film such as the glands and ducts surrounding the eye and the ocular surface. These structures maintain the tear film via regulation of water and electrolyte transport and via mucin release by goblet cells. Among the ocular conditions where disruption of one of these structures can cause or lead to "dry eye disease" are: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies, pharmacologic side effects, eye stress and glandular and tissue destruction, environmental exposure to smog, smoke, excessively dry air, airborne particulates, autoimmune and other immunodeficient disorders, and comatose patients rendered unable to blink. This is not to be considered an exhaustive list but is used to describe some of the diseases that can lead to dry eye disease.

Treatment for dry eye disease is effective regulation of the tear film. This can be accomplished by enhancing natural production or improving flow from the glands surrounding the eye or applying artificial tears to the ocular surface. The glands can be blocked due to inflammation of the surrounding tissue or the duct and gland itself. Blockage due to inflammation can be seen by increases in pro-inflammatory cytokines, redness and puffiness on and surrounding the ocular surface. Reduction of this inflammation can help return tear production to normal function and improve corneal health. (Wilson S et al. *American Academy of Ophthalmology* 114 (1), 76-79 (2007)).

Currently, the pharmaceutical treatment of dry eye disease is mostly limited to administration of artificial tears (saline solution) to temporarily rehydrate the eyes and to reduction of inflammation ((Riento K et al. *Nat Rev Mol Cell Biol,* 4:446-456, 2003)). However, artificial tears, the most widely used group of products, often have contraindications and incompatibility with soft contact lenses (Lemp M et al. *Cornea* 9(1), S48-550 (1990)).

Macular Edema and Degeneration

Macular edema is a condition that occurs when damaged (or newly formed) blood vessels leak fluid onto the macula, a critical part of the retina for visual acuity, causing it to swell and blur vision. Macular edema is a common problem in diabetic retinopathy, where retinal vessel injury causes edema. Edema also occurs in the proliferative phase of diabetic retinopathy, when newly formed vessels leak fluid into either, or both, the macula and/or vitreous. Macular edema is commonly problematic in age-related macular degeneration (wet form) as well, where newly formed capillaries (angiogenesis) leak fluid into the macula.

Age related macular degeneration (AMD) is a progressive eye condition affecting as many as 10 million Americans. AMD is the number one cause of vision loss and legal blindness in adults over 60 in the U.S. As the population ages, and the "baby boomers" advance into their 60's and 70's, a virtual epidemic of AMD will be prevalent. The disease affects the macula of the eye, where the sharpest central vision occurs. Although it rarely results in complete blindness, it robs the individual of all but the outermost, peripheral vision, leaving only dim images or black holes at the center of vision.

Macular degeneration is categorized as either dry (atrophic) or wet (neovascular). The dry form is more common than the wet, with about 90% of AMD patients diagnosed with dry AMD. The wet form of the disease usually leads to more serious vision loss. In the dry form, there is a breakdown or thinning of the retinal pigment epithelial cells (RPE) in the macula, hence the term "atrophy". These RPE cells are important to the function of the retina, as they metabolically support the overlying photoreceptors.

The clinical hallmark of atrophic AMD is accumulation of macular drusen, yellowish deposits just deep to the retinal pigment epithelium ("RPE"). Histopathologic examination of eyes with atrophic AMD reveals deposition of lipid and proteinaceous material deep to the RPE in Bruch's membrane. Drusen formation occurs naturally with age, with ocular exposure to visible light and UV light, metabolic changes of ocular cells related to age, and the formation of lipofuscin. Genetic predisposition can also factor into drusen formation. The formation of drusen can result in local inflammation as extracellular debris forms around the RPE, photoreceptors, and other ocular structures. The immune response which results brings about a number of components, one of which is membrane attack complex. The membrane attack complex can cause the death of host cells, which would include the RPE and photoreceptors. As a consequence, more cellular debris and drusen form as a result of the local inflammatory response, perpetuating the cycle (Nowak J Z *Pharmacol Rep.* 58(3):353-363, 2006).

In aged eyes with AMD, Bruch's membrane is often about 3 times thicker than normal. This thickening is thought to be comprised of lipid as well as modified and cross-linked protein, which impedes transport of nutrients across Bruch's membrane from the choriocapillaries to the outer retina. This thickened barrier comprised of lipid and cross-linked protein impedes transport of nutrients across Bruch's membrane from the choriocapillaries to the outer retina. At present, there is no proven effective treatment for dry AMD other than the use of multivitamins and micronutrients.

Wet AMD occurs when new vessels form and grow through Bruch's membrane into the sub-RPE and subretinal space. This neovascular tissue is very fragile and hyperpermeable.

Frequently, it bleeds causing damage to the overlying retina. As the blood organizes, functional macular tissue is replaced by scar tissue. To prevent vision loss, it would be desirable to intervene therapeutically prior to the development of neovascularization.

AMD is a challenging disease for both patient and doctor, because there are very few treatment options and, with the exception of anti-oxidants, no proven preventative therapy. While some individuals experience only minor inconvenience from macular degeneration, many others with more severe forms of macular degeneration are incapacitated. Patients may experience a loss of central vision accompanied by metamorphopsia, central scotomas, increased glare sensitivity, decreased contrast sensitivity, and decreased color vision (Rosenburg et al. *American Family Physician*, 77(10): 1431-1436, 2008). Current therapies, including laser photocoagulation, photodynamic therapy, and anti-angiogenic therapeutics have had mixed results, and, in certain instances, have caused deleterious side effects. A need exists for additional treatments that reduce the effects of macular degeneration and edema.

Proliferative Vitreal Retinopathy

One of the most common causes of retinal detachment is proliferative vitreoretinopathy (PVR), an intraocular, non-malignant cellular proliferation. This process results ultimately in a separation of the retina from the retinal pigment epithelium, or RPE, because of tractional forces applied directly to the inner and outer retinal surfaces. This is the major cause for failure of retinal re-attachment surgery. (Ryan et al. *Am J Ophthalmol*, 100:188-193, 1985). PVR is characterized by the formation of contractile cellular epiretinal membranes (ERMs) on both sides of the retina. (Clarkson, et al. *Am. J, Ophthalmol.*, 84:1-17, 1977). While the pathobiology of PVR is not clear, it appears that RPE cells are key to the development of these ERM. (Laqua, et al. *Am. J. Ophthalmol.*, 80:602-618, 1975). A large body of evidence supports the concept that previously quiescent RPE cells, when displaced into the vitreous cavity and exposed to the appropriate combination of cytokines, will divide and differentiate. This differentiation results in cells having myofibroblastic characteristics including adhesiveness and contractility. As these membranes form tight adhesions with the retinal surfaces, tractional forces are generated and detachment ensues. (Hiscott, et al. *Br. J. Ophthalmol.*, 68:708-715, 1984). Most evidence indicates retinal tears as the pathway through which RPE cells move in order to enter the vitreous cavity (Hiscott, et al. *Br. J. Ophthalmol.*, 68:708-715, 1984), and there is a clear association between the size of a retinal tear and the incidence of PVR. (Ryan et al. *Am. J. Ophthalmol.*, 100:188-193, 1985). Viable retinal pigment epithelial cells, displaced into the vitreous cavity, are exposed to a wide variety of proteins, cytokines, and chemoattractants. Extracellular matrix proteins have profound effects on cell morphology and behavior (Glaser, et al. *Ophthalmology*, 100:466-470, 1993). RPE cells, when exposed in vitro to the extracellular matrix proteins and collagens found in the vitreous, change from their typical epithelial cell morphology to a mesenchymal or fibroblast-like morphology (Hay, et al. Cell Biology of Extracellular Matrix, New York, Plenum Press, 1982). The pathobiology of PVR, while not understood completely, involves the exposure of previously quiescent cells to factors which promote abnormal differentiation and cell division. This differentiation results in adhesive cells which contract in an unregulated, disorganized fashion and produce the tractional forces which detach the retina. (Mandelcorn, et al. *Am J Ophthalmol*, 80:227-237, 1975).

The small GTPase, Rho, regulates the organization of the actin cytoskeleton by promoting the assembly of focal adhesions and actin stress fibers. A family of Rho-associated serine/threonine kinase isozymes named p160RHO KINASE and $ROK_\alpha$/Rho-kinase/RHO KINASE 2 has been identified as a class of Rho effectors that can induce focal adhesions and stress fibers in cultured fibroblasts and epithelial cells in vitro. (Amano M, Chihara K, Kimura K, et al. *Science*, 275:1308-1311, 1997). In patients with PVR, ERMs are characterized by the diffuse presence of α-smooth muscle actin (α-SMA)-positive myofibroblasts, which is presumed to be dedifferentiated RPE cells. (Casaroli-Marano R P et al. *Invest Ophthalmol Vis Sci*, 40:2062-2072, 1999). Dense bundles of α-SMA microfilaments forming stress fibers within the myofibroblast were observed by electron microscopy in the ERM of patients with PVR, which strongly suggests that α-SMA substantially contributes to PVR development. (Casaroli-Marano R P, et al. *Invest Ophthalmol Vis Sci.*, 40:2062-2072, 1999). A previous study has shown that the Rho kinase inhibitor Y-27632 suppresses type I collagen gel contraction in RPE cells, probably by suppressing expression of α-SMA, which led to attenuation of PVR in an animal model. (Zheng Y. et al. *Invest Ophthalmol Vis Sci.*, 45(2):668-74, 2004).

The current treatment for PVR is vitreoretinal surgery. Although such treatment often is successful, recurrent vitreoretinal traction may result in redetachment. The resulting retinal detachment sometimes causes permanent impairment of visual function. Pharmacologic and other forms of therapy to inhibit recurrent membrane formation are needed.

Blepharitis

Blepharitis, also known as Lid Margin Disease (LMD), is a non-contagious inflammation of the eyelids that manifests itself through scaling and flaking around the eyelashes, excess sebum production and oily scaly discharge, mucopurulent discharge, and matted, hard crusts around the lashes. Accumulation of crust, discharge or debris on the eyelashes and lid margins creates an ideal environment for overgrowth of the staphylococcal bacteria naturally found on the skin of the eyelids and increases the chance of infection, allergic reaction and tear break down. Blepharitis disturbs the production of the critical, outer lipid layer of the tear film which causes the entire tear to evaporate, resulting in dry eye. A reduced tear quantity doesn't properly dilute bacteria and irritants, nor wash inflammatory products away from the lashes and lid margin, so they accumulate and lead to further inflammation worsening the cycle of disease, with blepharitis, meibomian gland dysfunction and dry eye perpetuating each other.

Routine examination of the eyelids of blepharitis patients shows redness caused by capillary congestion (erythema) as well as crusting of the lashes and lid margins. More detailed inspection using a high magnification slit lamp microscope reveals additional features, including loss of lashes (madarosis), whitening of the lashes (poliosis), scarring and misdirection of lashes (trichiasis), crusting of the lashes and meibomian orifices, eyelid margin ulcers, plugging of the meibomian orifices, and lid irregularity (tylosis).

Blepharitis is a common eye disorder throughout the Unites States and the world. There is an apparently high incidence in the general population based on the frequency of diagnoses in ophthalmologists' offices. It affects people of all ages; however blepharitis caused by seborrhea is seen more often in older patients around the age of fifty. Chronic blepharitis has been associated with occupations in which the hands are dirty for much of the day, since poor hygiene is a risk factor. Acute blepharitis results most commonly from an allergic reaction to a drug or chemical substance. Likewise, exposure to irritants such as chemical fumes, smoke, and environmental pollutants can exacerbate the condition of chronic blepharitis. The use of certain drugs can also cause blepharitis. It has been documented that some patients on cancer chemotherapeutic agents such as 5-fluorouracil develop ocular surface and lacrimal complications, including blepharitis, conjunctivitis, keratitis, and eyelid dermatitis (Eiseman A S et al. *Ophthal Plast Reconstr Surg,* 19:3:216-224, 2003).

Designing an effective treatment plan for blepharitis can be challenging. Treatment includes good hygiene and relies heavily on the patient as a partner in achieving disease management. Since lid scrubs and hot compresses are required multiple times daily, long-term compliance to produce positive results can be an issue. If left untreated, blepharitis can lead to a more serious condition called ulcerative blepharitis accompanied by eyelid scarring, scarring of the cornea, and eventually loss of visual function.

It is well known that during acute and chronic inflammation various putative mediators of inflammation are released by the inflamed tissues and by leukocytes. The concentrations of these mediators and leukocytes are indicative of the level or degree of inflammation. Likewise, a reduction in concentration of these mediators and leukocytes is an indication of the effectiveness of a drug in treating inflammation. Anti-inflammatory steroidal preparations (e.g., corticosteroids) are currently the drug of choice in the treatment of ocular inflammatory conditions. The use of a topical ophthalmic steroid can be helpful in reducing acute inflammation, however extended use is complicated by severe and numerous side effects. It would be highly desirable to develop new nonsteroidal drugs which have a high therapeutic effectiveness but which do not exhibit steroid-like side effects.

Rho kinase signaling pathways have been implicated in the down regulation of pro-inflammatory pathways (Riento K et al. *Nat Rev Mol Cell Biol,* 4:446-456, 2003). For example, Rho kinase inhibition by Y-27632 and fasudil in a murine model of airway hyper-reactivity has been shown to reduce the mediators of inflammation (Taki F et al. *Clinical and Experimental Allergy,* 37:599-607, 2007).

There is a need for an effective or improved method for treating ophthalmic disease such as allergic conjunctivitis, corneal hyposensitivity and kerotopathy, dry eye disease, proliferative vitreal retinopathy, macular edema and degeneration, and blepharitis.

Asthma

Asthma is a common chronic disorder of the airways characterized by variable and recurring symptoms, reversible airway obstruction, bronchial hyperresponsiveness, and an underlying inflammation. Acute symptoms of asthma include cough, wheezing, shortness of breath and nocturnal awakening. These symptoms usually arise from bronchospasm and require and respond to bronchodilator therapy (see Expert Panel Report 3: Guidelines for the Diagnosis and Management of Asthma, NIH Publication No. 07-4051, Bethesda, Md.: U.S. Department of Health and Human Services; National Institutes of Health; National Heart, Lung, and Blood Institute; National Asthma Education and Prevention Program, (2007) and references therein).

Central to the pathophysiology of asthma is the presence of underlying airway inflammation mediated by the recruitment and activation of multiple cell types including mast cells, eosinophils, T lymphocytes, macrophages, dendritic cells and neutrophils. Type 2 T-helper (Th2) cells appear to play a central role in the activation of the immune cascade that results in inflammation. Th2-derived cytokines include IL-5, which is needed for eosinophil differentiation and survival, and IL-4 which is important for Th2 cell differentiation and with IL-13 is important for IgE formation and leads to overproduction of IgE and eosinophilia. IgE-driven activation of mucosal mast cells releases bronchoconstrictor mediators such as histamine and cysteinyl-leukotrienes as well as inflammatory cytokines. Eosinophils contain inflammatory enzymes, generate leukotrienes, and express a wide variety of pro-inflammatory cytokines. Airway epithelial cells also play a role in the inflammatory process via release of cytokines such as eotaxin that direct and modify the inflammatory response. Acute and chronic inflammation can affect not only the airway caliber and airflow but also can increase the existing bronchial hyperresponsiveness to a variety of stimuli, which enhances susceptibility to bronchospasm.

As a consequence of airway inflammation and the generation of growth factors, the airway smooth muscle cell can undergo proliferation, activation, contraction, and hypertrophy—events that can influence airway airflow limitation. In asthma, the dominant physiological event leading to clinical symptoms is airway narrowing and a subsequent interference with airflow. In acute exacerbations of asthma, bronchial smooth muscle contraction (bronchoconstriction) occurs quickly to narrow the airways in response to exposure to a variety of stimuli including allergens or irritants. Allergen-induced acute bronchoconstriction results from an IgE-dependent release of mediators from mast cells that includes histamine, tryptase, leukotrienes, and prostaglandins that directly contract airway smooth muscle. The mechanisms influencing airway hyperresponsiveness are multiple and include inflammation, dysfunctional neuroregulation, and airway remodeling. Airway remodeling involves structural changes including thickening of the sub-basement membrane, subepithelial fibrosis, airway smooth muscle hypertrophy and hyperplasia, blood vessel proliferation and dilation with consequent permanent changes in the airway that increase airflow obstruction and that is not prevented by or fully reversible by current therapies.

Airway epithelium and endothelial cell function are also critically involved in asthma. Upon disease progression, epithelial subbasement membranes thicken with mucus hypersecretion and the formation of inspissated mucus plugs. Changes in endothelial cell integrity lead to edema, another key pathophysiology defining asthmatic change of the airway. These factors serve to further limit airflow and are not directly addressed by current therapies.

Current standard therapies for asthma are a combination of corticosteroids and $\beta_2$-agonists (anti-inflammatory and bronchodilator drugs). These drugs provide acceptable control of the disease for many asthmatics. However, it is estimated that 5 to 10% of the asthma patients have symptomatic disease despite treatment with this combination of corticosteroids and $\beta_2$-agonists (Chanez et al., J Allergy Clin Immunol 119: 1337-1348 (2007)).

Chronic Obstructive Pulmonary Disease

Chronic obstructive pulmonary disease (COPD) is the most common chronic lung disease associated with significant morbidity and mortality. In the United States, COPD is the fourth leading cause of death and accounts for more than $30 billion in annual health care costs. An estimated 16 million adults are affected by COPD, and each year ~120,000 Americans die of the disease. COPD is defined as a chronic disease characterized by airway/alveolar/systemic inflammation, with measured airflow obstruction ($FEV_1/FVC<70\%$ and $FEV_1<80\%$ predicted) that is partially improved with bronchodilator therapy. The local and systemic release of inflammatory mediators by the lung cells leads to airway disease (chronic obstructive bronchitis) and, in a minority of patients, to destruction of parenchymal tissue (emphysema), both of which can result in the airflow limitation that characterizes COPD (see Doherty D E et al, Clin Cornerstone 6:S5-16 (2004) and MacNee, Clin Ches Med 28:479-513 (2007)). The release of these inflammatory mediators by the lung cells may also exacerbate inflammation in other organ systems, such as that observed in coronary, cerebrovascular, and peripheral vascular conditions.

The chronic inflammation, airway obstruction, and tissue damage that occur in COPD all result from chronic exposure to inhaled toxic substances, primarily cigarette smoke. In response to the chemical insult of inhaled tobacco smoke, inflammatory cells (including macrophages, neutrophils, and T-lymphocytes, primarily CD8 lymphocytes) are activated in the small and large airways as well as in the lung parenchyma. These activated inflammatory cells release a host of cytokines and other mediators (including tumor necrosis factor-α, interleukin [IL]-8, and leukotriene $B_4$), which can cause damage to lung tissue. The end result of the release of these cytokines and mediators may be the development of chronic inflammation of the airways, mucus gland hypertrophy and goblet-cell hyperplasia with increased mucus secretion, fibrosis and narrowing of smaller airways, destruction of the parenchyma (the connective tissue/cells in the lungs), and changes in the blood vessels that may result in the development of pulmonary hypertension. These pathologic changes manifest themselves as mucus hypersecretion, limited airflow, hyperinflation, and gas exchange abnormalities which are the major physiologic abnormalities that characterize COPD. A loss in the integrity of the lung's connective tissue leads to a decrease of elastic recoil and hyperinflation.

Current therapies to treat COPD include bronchodilators, especially anticholinergic agents, that help to some degree decrease hyperinflation, therefore increasing inspiratory capacity and relieving dyspnea. Although corticosteroids are an effective treatment for most cases of asthma, the inflammatory cells and mediators in COPD are not sensitive to treatment with systemic or inhaled corticosteroids making treatment with these agents of limited usefulness in COPD.

RSV Infection

Respiratory syncytial virus (RSV) causes acute respiratory tract illness in persons of all ages. RSV is a leading cause of lower respiratory tract infection (LRTI) in children younger than 2 years. It is associated with up to 120,000 pediatric hospitalizations each year, and is increasing in frequency. RSV also is a significant cause of morbidity and mortality from LRTI in elderly patients (Collins et al., J Virol 82:2040-2055 (2008); Peebles et al., Proc Am Thorac Soc 2:110-115 (2005)).

After replicating in the nasopharynx, RSV infects the small bronchiolar epithelium and extends to the type 1 and 2 alveolar pneumocytes in lung. Pathologic findings of RSV include necrosis of epithelial cells, occasional proliferation of the bronchiolar epithelium, infiltrates of monocytes and T cells centered on bronchial and pulmonary arterioles, and neutrophils between the vascular structures and small airways. This leads to airway obstruction, air trapping and increased airway resistance, and also is associated with a finding of neutrophilia in bronchoalveolar lavage. The immune response to RSV, especially cytokine and chemokine release, appears to play a role in the pathogenesis and severity of bronchiolitis. There is a distinct pattern of cytokines and chemokines induced by RSV infection and some have been associated with disease severity. The cytokines IL-8, IL-6, TNF-alpha, and IL-1 beta can be detected in airway secretions of infected children (Smyth et al. Arch Dis Child 76:210 (1997)), and IL-6 levels correlate with severe disease. Chemokines identified in respiratory tract secretions of children include CCL3, CCL2, CCL11 and CCL5, but only the beta-chemokines, particularly MIP-1 alpha, are associated with severe disease (Welliver et al. Pediatr Infect Dis J 21:457 (2002)).

RSV can involve both lower and upper respiratory tract. Severe lower respiratory tract disease can involve bronchiolitis, bronchospasm, pneumonia, and acute respiratory failure in children. Lower respiratory tract involvement usually occurs with primary infection, and may occur in second infections and can cause wheezing, tachypnea and apnea. Repeat RSV infections occur frequently in children and young adults and result in significant upper respiratory tract symptoms. Signs include cough, coryza, rhinorrhea, and conjunctivitis. RSV infection in adults also may cause short-term airway reactivity.

There is no direct treatment for RSV infection and the respiratory complications it causes. The current therapy for RSV is primarily supportive. Bronchodilator therapy in infants with bronchiolitis, largely caused by RSV infection, did not demonstrate benefit in large randomized trials and systematic reviews. Prophylaxis with palivizumab, a humanized monoclonal antibody, has been indicated for a limited fraction of the pediatric patient population.

Pulmonary Arterial Hypertension

Pulmonary arterial hypertension (PAH) is a disease of the small pulmonary arteries, characterized by vascular narrowing leading to a progressive increase in pulmonary vascular resistance. The consequence of this increased right ventricle after-load is the failure of the afterload-intolerant right ventricle. The pulmonary vascular injury underlying PAH occurs in an idiopathic form or in association with other disease states such as congenital heart disease or COPD. Vasoconstriction, remodeling of the pulmonary vessel wall, and thrombosis contribute to the increased pulmonary vascular resistance in PAH. However, it is now recognized that pulmonary arterial obstruction by vascular proliferation and remodeling is the hallmark of PAH pathogenesis (Humbert et al. J Am Coll Cardiol 43:13 S-24S (2004) and Rubin Proc Am Thorac Soc 3:111-115 (2006)). The process of pulmonary vascular remodeling involves all layers of the vessel wall. Indeed, each cell type (endothelial, smooth muscle, and fibroblast), as well as inflammatory cells and platelets, may play a significant role in PAH. A feature common to all forms of PAH remodeling is the distal extension of smooth muscle into small peripheral, normally nonmuscular, pulmonary arteries within the respiratory acinus. In addition, a hallmark of severe pulmonary hypertension is the formation of a layer of myofibroblasts and extracellular matrix between the endothelium and the internal elastic lamina, termed the neointima.

Pulmonary vasoconstriction is believed to be an early component of the pulmonary hypertensive process. Excessive vasoconstriction has been related to abnormal function or expression of potassium channels and to endothelial dysfunction. Endothelial dysfunction leads to chronically impaired production of vasodilators such as nitric oxide and prostacyclin along with overexpression of vasoconstrictors such as endothelin 1.

Inflammatory mechanisms appear to play a significant role in some types of pulmonary hypertension. Indeed, a subset of PAH patients have circulating autoantibodies including antinuclear antibodies, as well as elevated circulating levels of proinflammatory cytokines IL-1 and IL-6. Lung histology also revealed inflammatory infiltrates (macrophages and lymphocytes) in the range of plexiform lesions in severe PAH as well as an increased expression of chemokines RANTES and fractalkine.

Current therapies for PAH include prostanoids, endothelin receptor antagonists, and phosphodiesterase type V inhibitors. Despite these treatments, the average life expectancy of a PAH patient is generally under five years from the diagnosis of the disease.

Lymphangioleiomyomatosis

Lymphangioleiomyomatosis (LAM) and tuberous sclerosis complex (TSC) are caused by mutations in either of the tuberous sclerosis genes, TSC1 or TSC2, which control cell growth, survival, and motility through the Akt/mammalian target of rapamycin (mTOR) signaling pathway (McCormack Chest 133:507-516 (2008)). Deficiency or dysfunction of the encoded proteins, hamartin or tuberin, respectively, results in a loss of regulation of signals from upstream sources including cell surface tyrosine kinase and G protein coupled receptors. The constitutive activation of mTOR kinase and the downstream S6 kinase (S6K) leads to increased protein translation, and ultimately to inappropriate cellular proliferation, migration, and invasion. These changes lead to smooth muscle cell infiltration and cystic destruction of the lung resulting in progressive dyspnea on exertion, recurrent pneumothoraces, abdominal and thoracic lymphadenopathy, and abdominal tumors, including angiomyolipomas and lymphangiomyomas.

LAM occurs in about 30% of women with tuberous sclerosis complex (TSC) and also in women who do not have TSC (ie, sporadic LAM [S-LAM]). Both S-LAM and TSC-LAM are associated with mutations in tuberous sclerosis genes. In patients with TSC or TSC-LAM, germline mutations in TSC genes are present in all cells of the body and neoplasms and dysplasias occur when somatic TSC mutations result in a loss of heterozygosity for the normal allele. In patients with S-LAM, somatic TSC mutations are confined to lesions in the lung, kidney, and lymph nodes although respiratory involvement predominates.

There are no proven therapies for LAM although bronchodilator therapy is useful for some patients.

Idiopathic Pulmonary Fibrosis

Idiopathic pulmonary fibrosis (IPF) is a chronic, progressives fibrotic disorder of the lower respiratory tract that typically affects adults beyond the age of 40. IPF is thought to occur as a result of initial injury to the lung by environmental factors such as cigarette smoke leading to recruitment of neutrophils, lymphocytes and macrophages to the lung alveoli. Release of fibrogenic cytokines, such as TGF-β☐ by alveolar epithelial cells results in fibroblast proliferation, migration, and fibrosis. These fibroblasts not only fill the respiratory space but also secrete collagen and matrix proteins in response to many cytokines leading to parenchymal remodeling (Shimizu et al., Am J Respir Crit Care Med 163: 210-217 (2001)). This differentiation of fibroblasts is likely key to the chronic nature of IPF. These events lead to cough and progressive shortness of breath. IPF patients have compromised lung function and have shown restrictive lung volumes and capacities. Although corticosteroids, immunosupressive agents, neutrophil elastase inhibitor, hepatocyte growth factor, and interferon gamma-1b have been proposed as treatment agents for IPF, no treatment other than lung transplantation is known to prolong survival and IPF remains a fatal disorder with a 3 to 6 yr median range of survival (Khalil et al. CMAJ 171:153-160 (2004)). Thus, the first line of treatment of IPF has not yet been established.

Acute Respiratory Distress Syndrome (ARDS) and Ventilator Induced Lung Injury (VILI)

Acute respiratory distress syndrome is a critical illness characterized by acute lung injury leading to permeability pulmonary edema and respiratory failure. ARDS respiratory failure can be caused by various acute pulmonary injuries and is characterized by noncardiogenic pulmonary edema, respiratory distress, and hypoxemia. Despite significant advances in critical care management, overall mortality from ARDS ranges from 25 to 58% (Berstan A D et al. Am J Respir Crit Care Med, 165:443, 2002).

More than 60 causes of ARDS have been identified. A few common causes include sepsis, aspiration of gastric contents, primary bacterial or viral pneumonias, direct chest trauma, ventilator-induced lung injury, prolonged or profound shock, burns, fat embolism, near drowning, massive blood transfusion, transfusion-related lung injury (TRALI), cardiopulmonary bypass, pneumonectomy, acute pancreatitis, inhalation of smoke or other toxic gas, and ingestion of certain drugs (Pepe P et al. Am J Surg, 144:124, 1982; Hudson L D, J Respir Grit Care Med, 151:293, 1995; Zaccardelli D S and Pattishall E N, Grit Care Med, 24:247, 1996; Fowler A et al. Ann Intern Med, 98:593, 1983).

ARDS is described as a "syndrome of acute and persistent inflammation with increased vascular permeability associated with a constellation of clinical, radiological and physiological abnormalities" (Bernard G et al. Am J Respir Grit Care Med, 149:818, 1994; Artigas A et al. Am J Respir Grit Care Med, 157:1332, 1998). The hallmark of ARDS is deterioration in blood oxygenation and respiratory system compliance as a consequence of permeability edema. Whereas a variety of different insults may lead to ARDS, a common pathway probably results in the lung damage and/or failure, leukocyte activation within the lung, along with the release of oxygen free radicals, arachidonic acid metabolites, and inflammatory mediators, resulting in an increase in alveolocapillary membrane permeability. With the loss of this macromolecular barrier, alveoli are flooded with serum proteins, which impair the function of pulmonary surfactant (Said et al. J. Clin. Invest. 44: 458-464; Holm et al. J. Appl. Physio. 63: 1434-1442, 1987). This creates hydrostatic forces that further exacerbate the condition (Jefferies et al., J. Appl. Physio. 64: 5620-5628, 1988), leading to alveolar edema and a concomitant deterioration in gas exchange and lung compliance.

Mechanical ventilation is a common and generally effective means of treating a failing lung. Unfortunately, positive-pressure mechanical support can create or contribute to lung injury (ventilator-induced lung injury, VILI). Mechanical ventilators applying high volumes and pressures can lead to an influx of fluid into the lung. In addition to edema, the injured or ruptured cells trigger a cascade of cellular and biochemical events leading to the inflammation in the lung. Pulmonary sheer stress can develop due to the increased volume as well as due to atelectasis. VILI is also believed to provoke distal airway and alveolar cell inflammation by increasing the production of proinflammatory cytokines. In light of the fact that more than 280,000 Americans are at risk for VILI each year, and mechanical ventilation support and associated intensive care expenditures are estimated in the billions of dollars, VILI is a major public health concern (WO/2007/109582).

Rho kinase signaling pathways are implicated in an array of cellular phenomena many of which play roles in the pathophysiology of ARDS and VILI. These include cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. Several mechanisms such as increased endothelial permeability, inflammatory cell recruitment, and inflammation have been implicated in the pathogenesis of ARDS. Endothelial cells form a major part of the capillary permeability barrier in the lungs and changes are associated with increased capillary permeability (due to endothelial cell contraction and barrier dysfunction; Tinsley J H et al. *Am J Physiol Cell Physiol*, 279:C1285-1289, 2000). Inflammatory reactions may lead to endothelial paracellular gaps and extravasation of fluid and macromolecules. Airway epithelium can also contribute to inflammation by releasing inflammatory mediators, an event governed in part by Rho signaling (Cummings R J et al. J Biol Chem, 277:30227-30235, 2002).

Cystic Fibrosis (CF)

CF is the most common, life threatening, recessively inherited disease of Caucasian populations, with a carrier rate of 1 in 25 and an incidence of 1 in 2,500 live births. CF is a multisystem disease affecting the digestive system, sweat glands, and the reproductive tract, but progressive lung disease continues to be the major cause of morbidity and mortality (Ratjen, F and Doring, G. *Lancet* 361:681, 2003). CF patients have abnormal transport of chloride and sodium across the respiratory epithelium, resulting in thickened, viscous airway secretions (Rowe S M et al. *N Engl J Med;* 352:1992, 2005). Patients develop chronic infection of the respiratory tract with a characteristic array of bacterial flora (Gibson, R L et al. *Am J Respir Crit Care Med* 168:918, 2003), leading to progressive respiratory insufficiency and eventual respiratory failure. CF is caused by mutations in a single large gene on chromosome 7 that encodes the cystic fibrosis transmembrane conductance regulator (CFTR) protein (Rommens J M et al. *Science;* 245:1059, 1989; Collins F S. *Science;* 256:774, 1992; Drumm, M L et al. *Mol Genet Med;* 3:33, 1993). CFTR has been shown to function as a regulated chloride channel, which in turn may regulate the activity of other chloride and sodium channels at the cell surface (Boucher R C. *Am J Respir Crit Care Med.* 150:271-281, 1994). Defective CFTR results in abnormal ion transport and airway surface liquid volume with alterations in the rheology of airway secretions, which become thick and difficult to clear (Wine J J. *J Clin Invest;* 103:309, 1999). These changes result in reduced mucociliary clearance and a propensity for chronic infection of the respiratory tract with resulting inflammation, progressive airway damage, bronchiectasis, progressive respiratory failure, and death (Mickle J E and Cutting G R. *Clinics in Chest Med.* 19(3):443-458, 1998).

Respiratory symptoms of CF usually begin early in life (Ratjen, F. and Doring, G. *Lancet* 361:681, 2003). Respiratory manifestations include recurrent, progressively more persistent cough becoming productive, chronic infection (particularly *Pseudomonas aeruginosa*), and inflammation leading to progressive tissue damage in the airways. Once infection is established, neutrophils are unable to control the bacteria, even though there is massive infiltration of these inflammatory cells into the lung tissue. Recruited neutrophils subsequently release inflammatory cytokines, reactive oxygen species, and elastase, the latter of which overwhelms the antiproteases of the lung and contributes to progressive destruction of the airway walls. In addition, large amounts of DNA and cytosol matrix proteins are released by degranulating neutrophils, contributing to the increased viscosity of the airway mucus (Davis, P B. Pathophysiology of the lung disease in cystic fibrosis. In: Cystic Fibrosis, Davis, P B (Ed), Marcel Dekker, New York 1993. p. 193). Toxic metabolites released by *P. aeruginosa* increase the rate of neutrophil apoptosis and decreased removal of apoptotic cells by pulmonary macrophages (Bianchi S M et al. *Am J Respir Crit Care Med* 177:35-43, 2008), contributing to the accumulation of DNA, protein, and cellular debris in the airway and exacerbating inflammation. Lung damage ultimately advances to the stage of irreversible bronchiectasis (dilated, collapsible airways), leading to progressive air and mucus trapping and ultimate respiratory failure. Other late complications include spontaneous pneumothorax (collapsed lung) and hemoptysis (coughing up blood), which may be massive (Flume P A et al. *Chest;* 128:720, 2005; Flume P A et al. *Chest* 128:729, 2005). Terminal findings often include severely congested parenchyma, with grossly purulent secretions in dilated airways. The airway epithelium is hyperplastic, often with areas of erosion and squamous metaplasia. Plugs of mucoid material and inflammatory cells are often present in the airway lumen. Submucosal gland hypertrophy and hyperplasia of airway smooth muscle may also be present (Hays S R et al. *Thorax* 60:226, 2005.)

Airway hyperreactivity is a common finding in CF patients (Hiatt P et al. *Am Rev Respir Dis* 137:119, 1988). Many CF patients continue to demonstrate bronchial hyperresponsiveness into adolescence and adulthood, with positive correlations between the degree of airway reactivity and the overall severity of lung disease. The response to bronchodilators does not always persist with increasing age, and some patients demonstrate worsening of expiratory airflow in response to treatment with beta-adrenergic reagents (Gibson, R L et al. *Am J Respir Crit Care Med* 168:918, 2003). This phenomenon may occur when progressive airway damage leads to a loss of cartilaginous support, resulting in an increased reliance on muscle tone for maintenance of airway patency. Muscle relaxation in this setting can cause collapse of such "floppy" airways, leading to increased airflow obstruction.

The chest radiography may appear normal for an extended period in patients with mild lung disease. As the disease progresses, hyperinflation becomes persistent, and interstitial markings become more prominent. Increasing hyperinflation leads to progressive flattening of the diaphragms, a prominent retrosternal space, and kyphosis (curvature of upper spine) in late stages of disease. Thin-walled cysts may appear to extend to the lung surface, and pneumothorax is observed with increasing frequency in older patients. Computed tomography (CT) of the chest may be helpful in defining the extent of bronchiectasis in some patients (de Jong, P A et al. *Radiology* 231:434, 2004.]. This is of particular interest in patients who have focal areas of advanced disease, which may sometimes be amenable to surgical resection.

Changes in pulmonary function may be identifiable from a very early age, even before clinical signs of disease are apparent (Long F R et al. *J Pediatr* 144:154, 2004; Castile R G et al. *Pediatr Pulmonol* 37:461, 2004). Over time, the majority of CF patients develop an obstructive pattern on pulmonary function testing (PFT). Increases in the ratio of residual volume to total lung capacity (RV/TLC) and decreases in the forced expiratory flow at 25 to 75 percent of lung volume ($FEF_{25-75}$) provide the most sensitive measures of early airway obstruction. As disease progresses, the forced expiratory volume in one second ($FEV_1$) and the ratio of $FEV_1$ to forced vital capacity ($FEV_1$/FVC) decline (Davis, P B. Pathophysiology of the lung disease in cystic fibrosis. In: Cystic Fibrosis, Davis, P B (Ed), Marcel Dekker, New York 1993. p. 193). The $FEV_1$ is correlated with subsequent survival in CF patients. An $FEV_1$ persistently lower than 30 percent of predicted may be a useful indicator of the need for transplant evaluation in patients who are considered appropriate candidates for that procedure (Kerem E et al. *N Engl J Med;* 326:1187, 1992). Lung volumes demonstrate increases in total lung capacity (TLC) and residual volume (RV) as hyperinflation progresses. Despite aggressive therapy, baseline pulmonary function gradually decreases as patients get older.

As bronchiectasis and airway obstruction become pronounced, ventilation-perfusion mismatch leads to hypoxemia. This may initially occur only during sleep or exercise, but patients with advanced disease often require continuous oxygen supplementation. Hypercapnia occurs relatively late in the course of CF lung disease. Chronic hypoxemia and hypercapnia may lead to muscular hypertrophy of the pulmonary vasculature, pulmonary hypertension, right ventricular hypertrophy, and eventually cor pulmonale with right heart failure (Eckles M and Anderson P. *Semin Respir Crit Care Med* 24:323-30, 2003).

Therapeutic intervention for cystic fibrosis includes inhaled and oral antibiotics (tobramycin, azithromycin), bronchodilators (β-adrenergic agonists), DNase I (dornase alpha), hypertonic saline, chest physiotherapy, anti-inflammatory agents (azithromycin, ibuprofen, glucocorticoids), and lung transplantation. Although improved treatment of lung disease has increased survival, the median age for survival is still only 35 years (Cystic Fibrosis Foundation Patient Registry Annual Data Report, 2004), and patients continue to have significant morbidity, including hospitalizations (Ramsey B W. *N Engl J Med.* 335(3):179-188, 1996).

Bronchiectasis

Bronchiectasis is currently defined as the irreversible and sometimes progressive dilatation and destruction of the bronchial wall caused by a vicious pathogenic cycle of impaired local defense mechanisms, infection, and airway inflammation (Garcia, Arch Bronconeumol, 41(8):407-9, 2005). Bronchiectasis is a syndrome of chronic cough and daily viscid sputum production associated with airway dilatation and bronchial wall thickening. Hemoptysis can also occur. Multiple conditions are associated with the development of bronchiectasis, but all require an infectious insult plus impairment of drainage, airway obstruction, and/or a defect in host defense (Barker, A. F. Clinical manifestations and diagnosis of bronchiectasis. In: UpToDate, King T E (Ed) UpToDate, Wellesley, Mass., 2008).

All types of bronchiectasis are characterized by predominately neutrophilic and mononuclear inflammation with scores of cellular mediators that modulate both acute and chronic inflammatory response and perpetuate the bronchial lesion (Garcia, Arch Bronconeumol, 41(8):407-9, 2005) The ensuing host response, immune effector cells, neutrophilic proteases, reactive oxygen intermediates (eg, hydrogen peroxide [$H_2O_2$]), and inflammatory cytokines, causes transmural inflammation, mucosal edema, cratering, ulceration, and neovascularization in the airways. The result is permanent abnormal dilatation and destruction of the major bronchi and bronchiole walls. Recurrent infection is common, which can lead to further scarring, obstruction, and distortion of the airways, as well as temporary or permanent damage to the lung parenchyma (Barker, A. F. Clinical manifestations and diagnosis of bronchiectasis. In: UpToDate, King T E (Ed), UpToDate, Wellesley, Mass., 2008). The characteristic clinical picture is chronic purulent sputum, functional impairment in the form of air flow obstruction, multiple exacerbations of an infectious type that occasionally involve atypical microorganisms, and dyspnea in advanced stages of the disease-all of which cause progressive deterioration of the patient's quality of life (Garcia, Arch Bronconeumol, 41(8):407-9, 2005). Mortality is difficult to estimate given the difficulty in identifying prevalence and the lack of definitive studies. One study from Finland identified 842 patients aged 35-74 years with bronchiectasis and followed them for 8-13 years. These patients were also compared with asthma and COPD controls. The mortality was not found to be significantly different among the 3 groups (bronchiectasis, asthma, COPD) with mortality rates of 28%, 20%, and 38% respectively. Currently, mortality is more often related to progressive respiratory failure and cor pulmonale than to uncontrolled infection. Life-threatening hemoptysis may also occur but is uncommon (Emmons Bronchiectasis. In: WebMD Hollingsworth, H M (Ed) 2008). Bronchiectasis is the prototypical disease for which secretion loosening or thinning combined with enhanced removal techniques should be salutary, although large population and long-term studies of efficacy are lacking. This is particularly important as tenacious secretions and mucous plugs are frequently present. Potential approaches include hydration, nebulization with saline solutions and mucolytic agents, mechanical techniques, bronchodilators, and anti-inflammatory therapy. (Barker, A. F. Treatment of bronchiectasis. In: UpToDate, King T E (Ed), UpToDate, Wellesley, Mass., 2008.) Treatment of bronchiectasis is aimed at controlling infection and improving bronchial hygiene. Since infection plays a major role in causing and perpetuating bronchiectasis, reducing the microbial load and attendant mediators is a cornerstone of therapy (Barker, A. F. Treatment of bronchiectasis. In: UpToDate, King T E (Ed), UpToDate, Wellesley, Mass., 2008).

Treatment strategies including daily oral antibiotic treatment, daily or three times weekly use of a macrolide antibiotic treatment, aerosolization of an antibiotic, and intermittent intravenous antibiotics have not been established in long-term studies (Barker, A. F,). Several antibiotic treatment strategies are expensive and require extra equipment and personnel and only target part of the pathophysiology of the disease. Other treatments include physiotherapy, hydration with oral liquids and nebulization with hyperosmolar or mucolytic agents, bronchodilators, anti-inflammatory medications such as corticosteroids, and surgery. (Barker, A. F.) Thus, the treatments for bronchiectasis are limited in their ability to affect key pathophysiologies of the disease.

Alpha-1-Antitrypsin Deficiency (AATD)

AATD is a common inherited genetic disorder which severely affects up to 100,000 people in the US alone. (Campos, M A et al. *Chest,* 128:1179, 2005). An important physiological role for alpha-1-antitrypsin (AAT) is to protect lung elastin from degradation by serine proteases such as neutrophil elastase, which is repeatedly produced by lung tissues as a normal immune response to inhaled airborne pathogens. Low levels of AAT and/or secretion of defective AAT can lead to an imbalance between antiproteases and their target serine proteases, leading to tissue damage by these potent degrading enzymes (Koehlein, T et al. *Am J Med.,* 121:3-9, 2008).

A further aspect of the secretion of defective protein is the loss of the anti-inflammatory properties exerted by the normal protein. AAT is mainly produced in the hepatocytes, with the most common inherited AAT defect giving rise to an accumulation of abnormal protein in these cells, often resulting in cell damage (Lomas, D A, et al. *Nature,* 357:605, 1992). In the lung, the alveoli show low levels of functional AAT, often leading to an imbalance between antiprotease and protease, and consequential tissue destruction. While the correlation between the severity of the protein deficiency and resultant disease is somewhat variable (Silverman, E K et al. *Ann Intern Med,* 111:982, 1989), AATD is associated with increased risk for COPD, emphysema, asthma, chronic bronchitis, and brochiectasis in the lung, as well as cirrhosis, hepatitis, hepatocarcinoma or liver failure.

A major risk factor for COPD and emphysema in AATD patients is smoking, thus a smoking cessation program is a critical first-line defense against the progression of disease. Current available therapies for COPD and emphysema include use of long acting beta-agonists and anticholinergics to promote bronchorelaxation, treatment with steroids to reduce inflammation, or supplementation of AAT levels with AAT isolated from the pooled blood of human donors. (Koehlein, T et al. *Am J Med.*, 121:3-9, 2008). A recombinant form of AAT is not yet available for clinical use (Trexler, M M, et al. *Biotechnol Prog*, 18:501, 2002). However, as none of these therapies are particularly effective, there is an unmet medical need for improved drugs for the treatment of AATD induced lung disease.

Rhinitis

Rhinitis is irritation and inflammation of the mucosal lining of the nose, which may be caused by allergies or other factors such as cigarette smoke, changes in temperatures, and exercise and stress. The resulting irritation and inflammation generate excessive amounts of mucus producing a runny nose, nasal congestion, and post-nasal drip. Rhinitis is a global health concern and is often combined with asthma in determining morbidity due to respiratory diseases. It is a complex disease affecting approximately 20% of the population. Rhinitis occurs in different types: allergic or atopic rhinitis including seasonal and perennial forms. The mechanism of perennial rhinitis with non-allergic triggers is not well understood. It is an allergy-like condition but not triggered by allergens. (Braunstahl et al. Current Opinion in Pulmonary Medicine 2003, 9:46-51). Idiopathic non-allergic rhinitis or vasomotor rhinitis is characterize by nasal congestion and post nasal drip in responses to temperature and humidity changes, smoke, odors, and emotional upsets. In general rhinitis is characterized by a symptoms complex that consists of any combination of the following: sneezing, nasal congestion, nasal itching and irritation, sneezing and watery rhinorrhea, frequently accompanied by nasal congestion. Perennial allergic rhinitis clinical symptoms are similar, except that nasal blockage may be more pronounced. Each type of allergic rhinitis may cause additional symptoms such as itching of the throat and/or eyes, excessive tearing, and edema around the eyes. These symptoms may vary in intensity from the nuisance level to debilitating. Other types of rhinitis present the same symptoms (Kim et al. Current Opinions in Otolaryngology & Head and Neck Surgery 2007, 15: 268-273).

Rho-kinase (RHO KINASE) regulates endothelial permeability by reorganization of the actin-based cytoskeleton and contraction of endothelial cells, resulting in the formation of an intercellular gap. (Walsh et. al. Gastroenterology 2001. 121(3): 566-579). Rho-kinase (RHO KINASE) regulates also regulates epithelial permeability by reorganization of the actin-based cytoskeleton and contraction of epithelial cells (Sawafuji et al. Am J Physiol Lung Cell Mol Physiol 289: L946-L953).

Rhinosinusitis

Rhinosinusitis, an inflammation of the sinus cavity, is the most commonly diagnosed chronic illness in the United States. The name of the disease "rhinosinusitis" is preferred over sinusitis as the inflammation of the sinuses rarely occurs without inflammation of the nasal mucosal at the same time. The disease affects over thirty million people in the United States alone. The treatments for rhinosinusitis are costly, exceeding $200 million per year. This illness is detrimental to both the overall quality of life and economic welfare of sufferers. Currently there is no universally accepted treatment for rhinosinusitis; therefore a need to identify new molecular pathways targeting the disease exists.

Sinusitis is the inflammation of the mucus membranes involving the paranasal sinuses, nasal cavity, and underlying bone. A leading theory suggests that exposure to allergens induces inflammation in the small channels of the ostiomeatal complex (OMC), which results in mucosal edema and ultimately impaired mucociliary clearance of the sinus ostia leading to blockage. As a result the trapped mucus becomes a breeding ground for bacteria and other microorganisms which can lead to infection. Common symptoms include pain varying from forehead to teeth, cheeks, ears, and neck, nasal drainage or postnasal drip and decreased sense of smell (Metson, R. et al. Chronic rhinosinusitis, In: UpToDate, Calderwood, S B (Ed), UpToDate, Wellesley, Mass., 2008).

Depending upon the durations of symptoms, rhinosinusitis may be classified as acute, sub acute, or chronic. Chronic sinusitis has long-term effects that could last over twelve weeks and accounts for >90% of all cases of rhinosinusitis The effects of chronic rhinosinusitis are debilitating even when compared to other chronic illnesses such as heart failure or pulmonary disease because it has potential to cause physical and physiological impairment (Metson, R. et al. Chronic rhinosinusitis, In: UpToDate, Calderwood, S B (Ed), UpToDate, Wellesley, Mass., 2008).

Other Respiratory Diseases Characterized by Airway Inflammation, Lung Tissue Edema, Bronchoconstriction and/or Airway Hyperreactivity Primary ciliary diskinesia (PCD), pneumonia, and bronchiolitis caused by agents other than RSV are respiratory disorders with medical need unmet by existing treatments and at least one of the following pathophysiologies accompanying these diseases: increased airway inflammation, lung tissue edema and/or bronchoconstriction or airway hyperreactivity. Pneumonia is a cause of significant morbidity and/or mortality in developed and developing world with World Health Organization estimates of 150.7 million cases worldwide every year. There is a variety of etiologic agents with large portion being viral and bacterial (i.e. *M. pneumoniae* or Influenza A and B). Pneumonia is accompanied by lung inflammation and lung tissue edema. PCD is a rare genetic mutation leading to defect in cilia. The main consequence is decreased ciliary clearance and increased airway inflammation due to recurrent respiratory infections and mucus accumulation in the airway. Bronchiolitis is a common cause of illness and hospitalization in infants and children younger than two years. Bronchiolitis is broadly defined as an illness characterized by wheezing and airways obstruction that is caused by infection with a viral or, less commonly, a bacterial pathogen resulting in inflammation of the small airways/bronchioles. Although respiratory syncytial virus (RSV) is the most common cause, parainfluenza virus, human metapneumovirus, influenza virus, adenovirus, rhinovirus, coronavirus, and human bocavirus are other infectious agents know to cause bronchiolitis.

OB/BOOP Due to Lung Transplantation and HSCT

Obliterative bronchiolitis (OB) is characterised by the onset of new air flow obstruction due to functional obstruction of the bronchioles. OB is a common late noninfectious pulmonary complication following both lung transplantation and allogeneic haematopoietic stem cell transplantation (HSCT) with an incidence of 50-60% in patients who survive for 5 years after lung transplantation and 0-48% following HSCT. OB accounts for more than 30% of all deaths occurring after the third postoperative year for lung transplant patients. The mortality rate in patients with OB following HSCT varies from 14-100%, with a median of 65%. Graft versus host disease is an established risk factor for OB after lung transplantation and HSCT. The histopathologic features of OB suggest that injury and inflammation of epithelial cells and subepithelial structures of small airways lead to excessive fibroproliferation, seemingly due to ineffective epithelial regeneration and aberrant tissue repair. The respiratory symptoms of OB include dry cough, dyspnea, and wheezing. Lung biopsies show small airway involvement with fibrinous obliteration of the lumen. BAL shows neutrophilic and/or lymphocytic inflammation. Despite treatment with corticosteroids and immunosuppression, improvement in lung function is noted in only 8% to 20% of patients with OB. Most patients with OB progress to respiratory failure, and some patients develop bronchiectasis with frequent bacterial exacerbations (Afessa B, Bone Marrow Transplantation 28: 524-434, 2001; Nicod L P, *Proc Am Thorac Soc* 3: 444-449, 2006; Estenne M, Am J Respir Crit Care Med 166: 440-444, 2002).

Bronchiolitis obliterans organizing pneumonia (BOOP) is a complication of both lung transplantation and HSCT and is defined by the patchy distribution of plugs of granulation tissue that fill the lumens of the distal airways, extending into the alveolar ducts and alveolar sacs in association with chronic interstitial inflammation. Organizing pneumonia results from alveolar epithelial injury with subsequent intra-alveolar fibrosis, angiogenesis and inflammation. Clinically, patients present with fever, cough, dyspnea, and crackles on physical examination with onset between 1 and 13 months following HSCT. The clinical spectrum of BOOP ranges from a mild illness to respiratory failure and death. BOOP usually responds well to corticosteroid treatment, however, frequent relapse occurs and new therapeutic options are needed to treat BOOP. (Cordier et al, *Eur Resp J,* 28:422-446, 2006; Freudenberger T D et al. *Blood,* 102:3822-3828, 2003; Travis W D et al. *Am J Respir Grit Care Med* 165: 277-304, 2002).

The therapeutic options for BO/BOOP include corticosteroids and immunosuppressive agents. However, these treatments are often of limited efficacy and new treatment options are needed to address BO/BOOP following lung transplantation and HSCT.

Non-IPF Idiopathic Interstitial Pneumonia

The idiopathic interstitial pneumonias (IIPs) are a group of interstial lung diseases (ILD, also know as diffuse parenchymal lung disease or DPLD) that result from damage to the lung parenchyma by varying patterns of inflammation and fibrosis. The interstitium includes the space between the epithelial and endothelial basement membranes and it is the primary site of injury in the IIPs. However, these disorders frequently affect not only the interstitium, but also the airspaces, peripheral airways, and vessels along with their respective epithelial and endothelial linings. The IIPs described comprise a number of clinicopathologic entities, which are sufficiently different from one another to be designated as separate disease entities. The idiopathic interstitial pneumonias include the entities of idiopathic pulmonary fibrosis (IPF), nonspecific interstitial pneumonia (NSIP), cryptogenic organizing pneumonia (COP), acute interstitial pneumonia (AIP), respiratory bronchiolitis-associated interstitial lung disease (RB-ILD), desquamative interstitial pneumonia (DIP), and lymphocytic interstitial pneumonia (LIP). Several clinical findings common to the IIPs are exertional dyspnea or cough, bilateral diffuse interstitial infiltrates on chest radiographs, physiological and gas exchange abnormalities including a decreased carbon monoxide diffusion capacity (DLCO) and an abnormal alveolar-arteriolar $PO_2$ difference, and histopathologic abnormalities of the pulmonary parenchyma that are characterized by varying marked inflammation, fibrosis and remodeling (Raghu G et al. *Clin Chest Med* 25:409-419, 2004; Travis W D et al. *Am J Respir Crit Care Med* 165: 277-304, 2002). The clinical prognosis of these diseases ranges from mild illness to respiratory failure and death. Therapies for the IIPs include corticosteroids and immunosuppressive agents but current treatments are variably effective and new treatment options are needed to treat these diseases.

ILD Other than IPF, Non-IPF IIP, and OB/BOOP

Interstitial Lung Disease (ILD), also known as diffuse parenchymal lung disease (DPLD), represent a variety of disorders that lead to diffuse remodeling, architectural damage to normal lung tissue and inflammation that lead to progressive loss of lung function. In addition to the inflammation and fibrosis that is often seen in the lung parenchyma in ILD, the airways and the vasculature may also be prominently affected. The ILDs can be classified into 7 main groups: iatrogenic or drug-induced; occupational or environmental; granulomatous diseases including pulmonary sarcoidosis collagen-vascular disease; unique entities such as alveolar proteinosis, Langerhans cell granulomatosis, and lymphangioleiomyomatosis; idiopathic interstitial pneumonias including interstitial pulmonary fibrosis (IPF); and inherited disorders such as tuberous sclerosis, neurofibromatosis, metabolic storage disorders and Hermansky-Pudlak syndrome. The most prominent forms of ILD are IPF and pulmonary sarcoidosis. Several clinical findings are common to the ILDs: exertional dyspnea or cough; bilateral diffuse interstitial infiltrates on chest radiographs; physiological and gas exchange abnormalities including a decreased carbon monoxide diffusion capacity (DLCO) and an abnormal alveolar-arteriolar $PO_2$ difference; and histopathologic abnormalities of the pulmonary parenchyma that are characterized by varying degrees of inflammation, fibrosis and remodeling. The incidence of ILD is estimated to be 31.5 per 100,000/yr in males and 26.1 per 100,000/yr in females and the clinical prognosis of these diseases range from mild illness to respiratory failure and death (Raghu G et al. *Clin Chest Med* 25:409-419, 2004). The standard therapies for ILD include corticosteroids and immunosuppressive agents but current treatments are variably effective depending on the specific disease entity being treated and new treatment options that suppress inflammation and prevent fibroblast and myofibrobalst proliferation are needed to treat these diseases (Kim et al. *Ther Adv Respir Dis* 2:319-338, 2008).

There is a need for an effective or improved method for treating ophthalmic diseases such as allergic conjunctivitis, corneal hyposensitivity and kerotopathy, dry eye disease, proliferative vitreal retinopathy, macular edema and degeneration, blepharitis and disorders in which intraocular pressure is elevated, such as primary open-angle glaucoma. There is a need for an effective or improved method for treating pulmonary diseases such as asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP.

SUMMARY OF THE INVENTION

The present invention is directed to synthetic bridged bicyclic compounds of Formula I, which are inhibitors of Rho kinases. The present invention is also directed to pharmaceutical compositions comprising such compounds and a pharmaceutically acceptable carrier.

The present invention is also directed to a method of preventing or treating diseases or conditions associated with cellular relaxation and/or changes in cell-substratum adhesions. The invention provides a method of reducing intraocular pressure, including treating glaucoma such as primary open-angle glaucoma; a method of treating constriction of the visual field; a method of inhibiting wound healing after trabeculectomy; a method of treating posterior capsule opacification following extracapsular cataract extraction and intraocular lens implantation; a method of inhibiting angiogenesis; a method of modulating fluid transport on the ocular surface; a method of controlling vasospasm; a method of increasing tissue perfusion; a method of neuroprotection; and a method of vasoprotection to atherogenic agents.

The present invention is directed to methods of preventing or treating ocular diseases associated with excessive inflammation, proliferation, remodeling, neurite retraction, corneal neurodegeneration, vaso-permeability and edema. Particularly, this invention relates to methods treating ocular diseases such as allergic conjunctivitis, corneal hyposensitivity and kerotopathy, dry eye disease, proliferative vitreal retinopathy, macular edema and degeneration, and blepharitis, using novel Rho kinase inhibitor compounds.

The present invention is directed to methods of preventing or treating diseases or conditions of the lung associated with excessive cell proliferation, remodeling, inflammation, vasoconstriction, bronchoconstriction, airway hyperreactivity and edema. Particularly, this invention is directed to methods of treating pulmonary diseases such as asthma, chronic obstructive pulmonary disease, respiratory tract illness caused by respiratory syncytial virus, pulmonary arterial hypertension, lymphangioleiomyomatosis, idiopathic pulmonary fibrosis, acute respiratory distress syndrome and ventilator induced lung injury, cystic fibrosis, bronchiectasis, alpha-1-antitrypsin deficiency, rhinitis, rhinosinusitis, primary ciliary dyskinesia, pneumonia, bronchiolitis caused by agents other than respiratory syncytial virus, OB/BOOP due to lung transplantation or HSCT, non-IPF IIP and ILD other than IPF, non-IPF IIPs and OB/BOOP.

The methods comprise the steps of identifying a subject in need of treatment, and administering to the subject a compound of Formula I, in an amount effective to treat the disease.

The active compound is delivered to a subject either by systemic administration or local administration to the eye or lung.

DETAILED DESCRIPTION OF THE INVENTION

The inventors of the present invention have discovered compounds that are cytoskeletal active agents, which modify cell contractility, cell-cell and cell-substrate interactions, for example, by inhibiting actomyosin interactions. These compounds contain structural features that render them suitable for use as therapeutic agents for use in the treatment of ophthalmic and pulmonary disorders. The structures described herein provide new compounds with therapeutic utility.

DEFINITIONS

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 2 to 6 carbon atoms in the alkenyl moiety and from 6 to 10 carbon atoms inclusively in the aryl moiety.

"Arylalkynyl" refers to aryl-alkynyl-groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl-groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl-groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl-groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl-groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

"Heterocycle-alkyl" refers to heterocycle-alkyl-groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl-groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl-groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound of Formula I is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I encompass all possible hydrates and solvates, in any proportion, which possess the stated activity.

The term "edema" refers to an abnormal accumulation of extra-vascular fluid. Of particular relevance here is "pulmonary edema" which refers specifically to fluid accumulation within the lung interstitium or the lumen of the lung. Pulmonary edema is associated with a variety of systemic or lung diseases including respiratory syncytial virus infection (RSV), human metapneumovirus, pneumonia, influenza, ventilator induced lung injury (VILI), acute respiratory distress syndrome (ARDS), acute lung injury (ALI), and chronic obstructive pulmonary disease (COPD) such as chronic bronchitis and emphysema.

"Inflammation" generally refers to a localized reaction of tissue, characterized by the influx of immune cells, which occurs in reaction to injury or infection. Specifically, "pulmonary inflammation" is characterized by migration of inflammatory cells into the interstitium and the lumen of the lung, release of pro-inflammatory cytokines and chemokines, lung tissue remodeling and lung tissue apoptosis or necrosis. Pulmonary inflammation accompanies a variety of systemic or lung diseases including those noted in the aforementioned pulmonary edema definition.

"An effective amount" is the amount effective to treat a disease by ameliorating the pathological condition or reducing the symptoms of the disease. "An effective amount" is the amount effective to improve at least one of the parameters relevant to measurement of the disease.

Rho Kinase Inhibitor Compounds

The Rho kinase inhibitor compounds useful for this invention include compounds of general Formula I, and/or tautomers thereof, and/or pharmaceutically-acceptable salts, and/or solvates, and/or hydrates thereof.

A compound according to Formula I can exist in several diastereomeric forms. The general structures of Formula I include all diastereomeric forms of such materials, when not specified otherwise. Formula I also includes mixtures of compounds of this Formula, including mixtures of enantiomers, diastereomers and/or other isomers in any proportion.

Formula I

Compounds of Formula I are as follows:

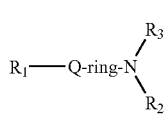

Formula I

Wherein:
$R_1$ is substituted aryl or substituted heteroaryl;
Q is $(CR_4R_5)_vC(=O)$, $(CR_4R_5)_vSO_2$, or $(CR_4R_5)_v$, in which $C(=O)$ and $SO_2$ are connected to ring;
v is 0, 1, 2, or 3;

$R_2$ is selected from the following heteroaryl systems, optionally substituted:

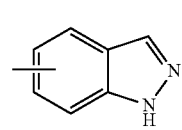

Indazole

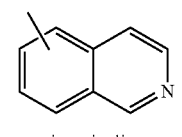

isoquinoline

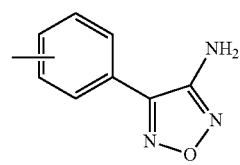

and $R_3$-$R_5$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, optionally substituted.

In Formula I, the subunit labeled "ring" is selected from the following bridged bicyclic systems:

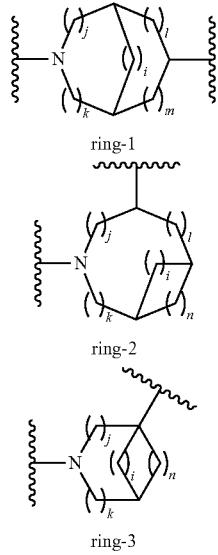

in which the points of connection of "ring" to Q and to $NR_2R_3$ are indicated by the broken lines, where N of ring is connected to Q, and other broken line is connected to $NR_2R_3$;
i and n are independently 1, 2, or 3;
j, k, l, and m are independently 0, 1, or 2;
the ring is optionally substituted by alkyl, cycloalkyl, aryl, heteroaryl, heterocycle, halo, oxo, $OR_6$, $NR_6R_7$, or $SR_6$;
and $R_6$ and $R_7$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, optionally substituted.

In these bridged rings, if the indicated ring is ring-1, then $1 \le j+k+l+m \le 6$, if the indicated ring is ring-2, then $1 \le j+k+l+n \le 6$, and if the indicated ring is ring-3, then $2 \le j+k+n \le 6$.

In Formula I, the preferred $R_1$ is substituted aryl, the more preferred $R_1$ is substituted phenyl, the preferred number of $R_1$ substituents is from 1-3, the preferred Q is $(CR_4R_5)_i$, the more preferred Q is $CH_2$, the preferred i and n are 1 or 2, the preferred j, k, l, and m are 0 or 1, and the preferred $R_3$-$R_7$ are H.

A preferred embodiment of Formula I is one in which one or more of the $R_1$ substituents are heteroatom-containing substituents.

An additional preferred embodiment of Formula I is one in which one or more of the $R_1$ substituents are in the form Y—Z, in which Z is attached to Q and Y is a substituent on Z.

In the substituent Y—Z, each instance of Y is chosen independently from H, alkyl, halogen, or the heteroatom-containing substituents, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Each instance of Z is chosen independently from alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, or is absent, with the proviso that if Z is absent, Y cannot be H;

$R_8$-$R_{10}$ are H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to halogen, $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, or $NR_{11}C(=O)NR_{12}R_{13}$;

$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

In Formula I, the preferred Y is H, alkyl, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$; the more preferred Y is alkyl, halogen, $OR_8$, or $NR_8SO_2R_9$; preferred Z is alkyl, alkenyl, alkynyl, cycloalkyl, cycloalkenyl, cycloalkylalkyl, or is absent; the more preferred Z is alkyl, alkenyl, alkynyl, cycloalkyl, or is absent; the preferred $R_8$ is H, alkyl, arylalkyl, cycloalkyl, cycloalkylalkyl, or heterocycle, the preferred $R_8$ substituents are halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and the preferred $R_9$-$R_{13}$ are H or alkyl.

The present compounds are useful for ophthalmic use, particularly in reducing intraocular pressure or treating glaucoma. To be therapeutically effective in ophthalmic use, the compounds must have both adequate potency and proper pharmacokinetic properties such as good permeability across the ocular surface. In general, compounds bearing polar functionality have preferred absorption properties and are particularly suitable for topical optical use. In general, compounds bearing small lipophilic functional groups have good Rho kinase inhibitory potency.

The inventors have discovered that the $R_1$ substitution in Formula I is an important factor for pharmacokinetic properties and Rho kinase inhibitory potency. The inventors have optimized and selected compounds that have improved ocular permeability and Rho kinase inhibitory potency. Specifically, compounds bearing polar functionality are particularly suitable for topical optical use with adequate Rho kinase inhibiting activity. Compounds bearing small lipophilic functional groups display Rho kinase inhibition with adequate ocular permeability.

In order to be useful as a pharmaceutical substance, an agent must be sufficiently potent and selective to achieve its intended effect. Potency and selectivity in drug substances can be enhanced in certain cases by incorporating rigid structural elements into the compound structure, so long as the proper active three dimensional conformation of the drug substance is maintained. The inventors have discovered that compounds of this invention incorporating rigid bridged bicyclic ring systems maintain an active conformation and are useful as potent Rho kinase inhibitors.

Specific Compounds illustrative of Formula I are shown in Table I. The example compounds have been numbered in the form "x.y.z" for ease of reference. In this numbering, "x" is a number given to the bicyclic ring used in the example ("ring" in Formula I), as shown in the listing below, "y" is 1, 2, or 3, and corresponds to the $R_2$ group $R_2$-1, $R_2$-2, or $R_2$-3 used in the example, and "z" is a sequential number given to each example compound having a given bicyclic ring and $R_2$ group. In the structures in Table I, hydrogens are omitted from the drawings for the sake of clarity and simplicity. Tautomers drawn represent all tautomers possible. Structures are drawn to indicate the preferred stereochemistry; where stereoisomers may be generated in these compounds, structures are taken to mean any of the possible stereoisomers alone or a mixture of stereoisomers in any ratio. The example compounds shown in Table I and the example bicyclic rings listed below are shown for the purpose of better illustrating the invention, and are not to be construed as limiting the invention in scope to the specific structures and rings described in them.

Listing of the Bicyclic Ring Numbering

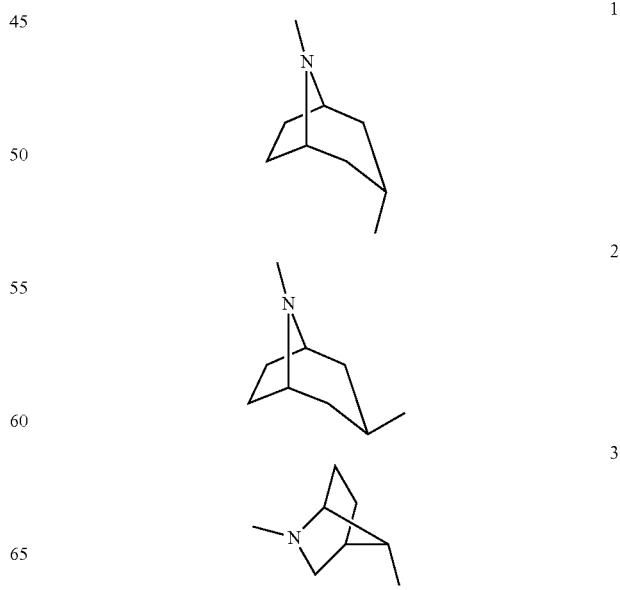

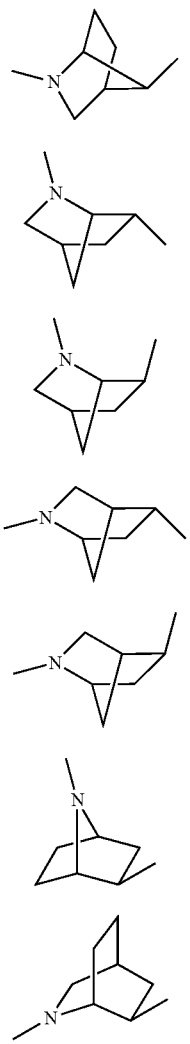

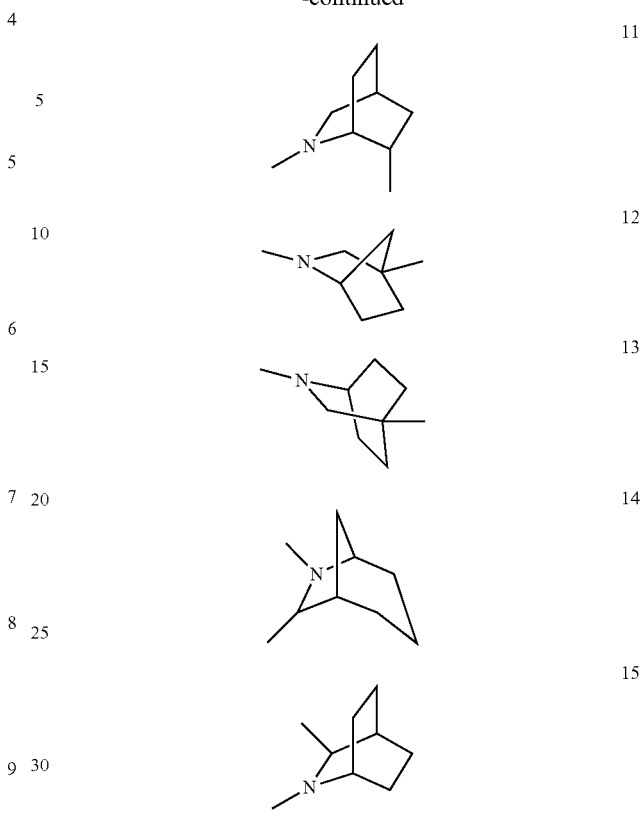

Preferred bicyclic rings are numbers 1-4; 1 and 4 are particularly preferred. In preferred Rings 1 and 2, j=k=0, i=2, l=1, and m=1. In preferred Rings 3 and 4, j=0, k=1, i=2, and l=m=0.

Rings 1-11 and 14-15 illustrate ring-1 of Formula I. Rings 12 and 13 illustrate ring-3 of Formula I. Rings 14 and 15 illustrate ring-2 of Formula I.

TABLE I

Example Compounds.

| Compound | Structure |
|---|---|
| 1.1.01 | N-((1RS,3rs,5SR)-8-benzyl-8-azabicyclo[3.2.1]octan-3-yl)-1H-indazol-5-amine |

TABLE I-continued
Example Compounds.
| Compound | Structure |
|---|---|
| 1.1.02 | 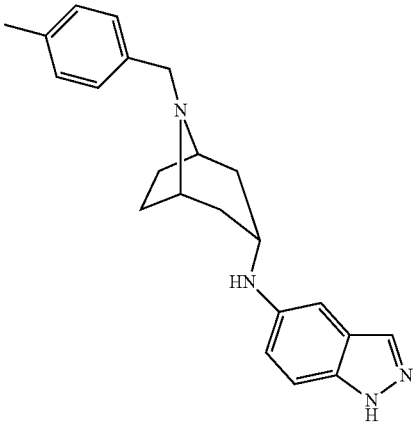<br>N-((1RS,3rs,5SR)-8-(4-methylbenzyl)-8-azabicyclo[3.2.1]octan-3-yl)-1H-indazol-5-amine |
| 1.1.03 | 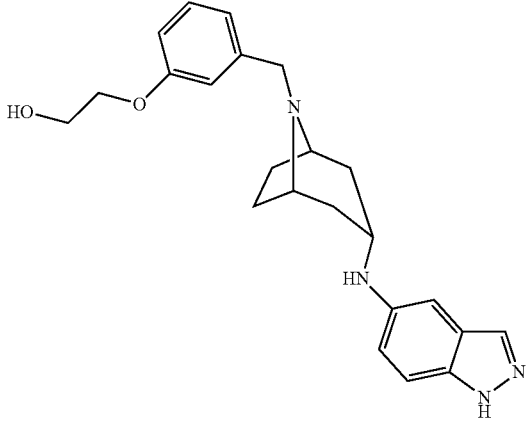<br>2-(3-((((1RS,3rs,5SR)-3-((1H-indazol-5-yl)amino)-8-azabicyclo[3.2.1]octan-8-yl)methyl)phenoxy)ethanol |
| 1.1.04 | 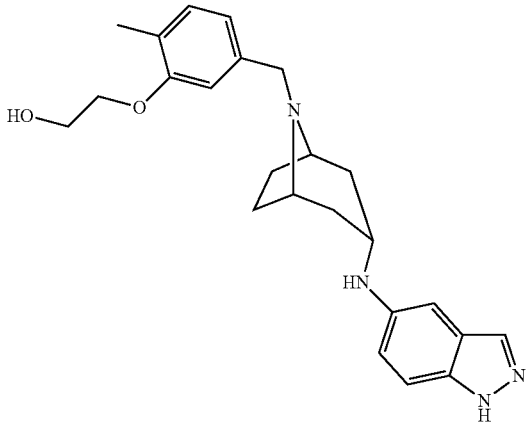<br>2-(5((((1RS,3rs,5SR)-3-((1H-indazol-5-yl)amino)-8-azabicyclo[3.2.1]octan-8-yl)methyl)-2-methylphenoxy)ethanol |

TABLE I-continued
Example Compounds.
| Compound | Structure |
| --- | --- |
| 1.2.01 | 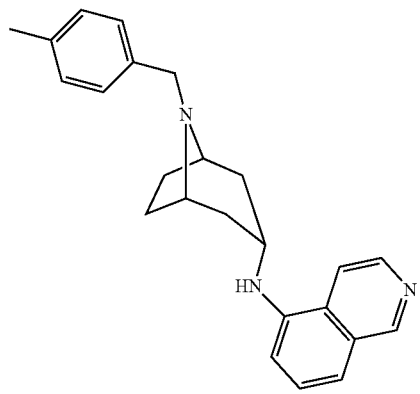<br>N-((1RS,3rs,5SR)-8-(4-methylbenzyl)-8-azabicyclo[3.2.1]octan-3-yl)isoquinolin-5-amine |
| 1.2.02 | 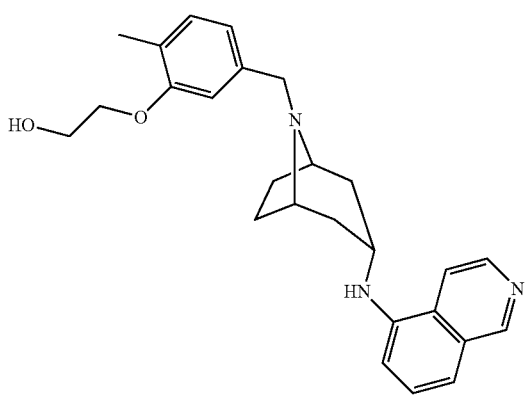<br>2-(5-(((1RS,3rs,5SR)-3-(isoquinolin-5-ylamino)-8-azabicyclo[3.2.1]octan-8-yl)methyl)-2-methylphenoxy)ethanol |
| 1.3.01 | 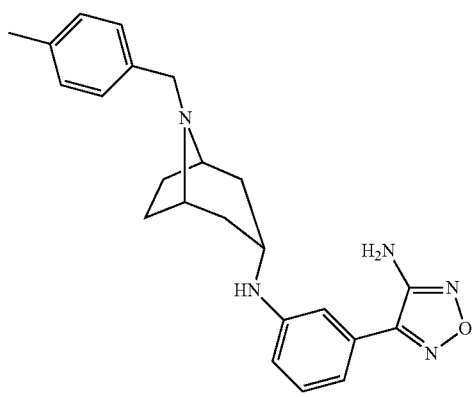<br>4-(3-(((1RS,3rs,5SR)-8-(4-methylbenzyl)-8-azabicyclo[3.2.1]octan-3-yl)amino)phenyl)-1,2,5-oxadiazol-3-amine |

TABLE I-continued
Example Compounds.
| Compound | Structure |
| --- | --- |
| 2.1.01 | 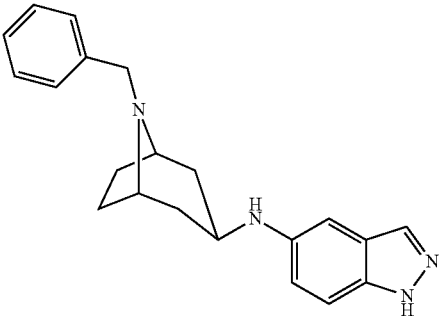<br>N-((1RS,3sr,5SR)-8-benzyl-8-azabicyclo[3.2.1]octan-3-yl)-1H-indazol-5-amine |
| 2.1.02 | 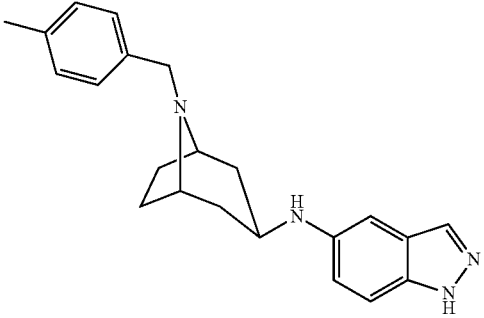<br>N-((1RS,3sr,5SR)-8-(4-methylbenzyl)-8-azabicyclo[3.2.1]octan-3-yl)-1H-indazol-5-amine |
| 2.1.03 | 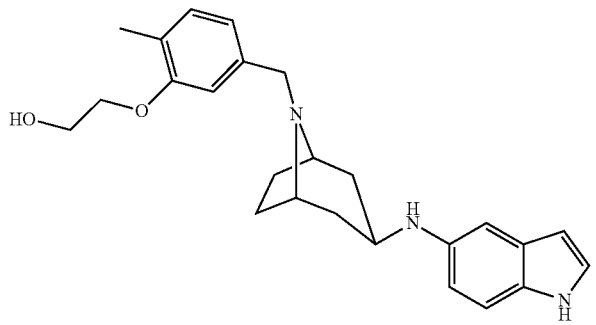<br>2-(5-(((1RS,3sr,5SR)-3-((1H-indazol-5-yl)amino)-8-azabicyclo[3.2.1]octan-8-yl)methyl)-2-methylphenoxy)ethanol |

TABLE I-continued
Example Compounds.
| Compound | Structure |
|---|---|
| 2.1.04 | 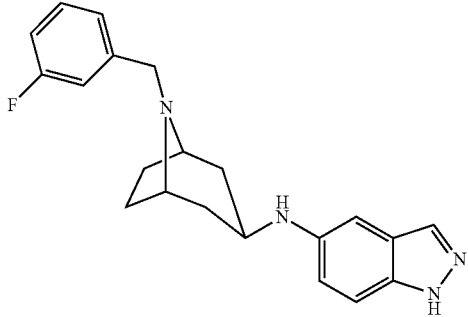<br>N-((1RS,3sr,5SR)-8-(3-fluorobenzyl)-8-azabicyclo[3.2.1]octan-3-yl)-1H-indazol-5-amine |
| 2.2.01 | 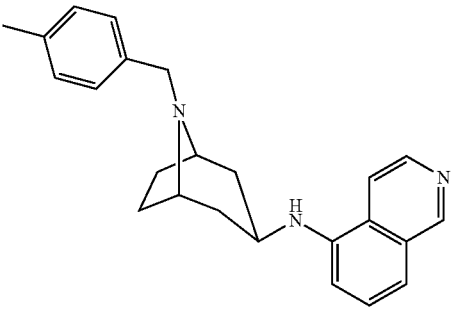<br>N-((1RS,3sr,5SR)-8-(4-methylbenzyl)-8-azabicyclo[3.2.1]octan-3-yl)isoquinolin-5-amine |
| 2.2.02 | 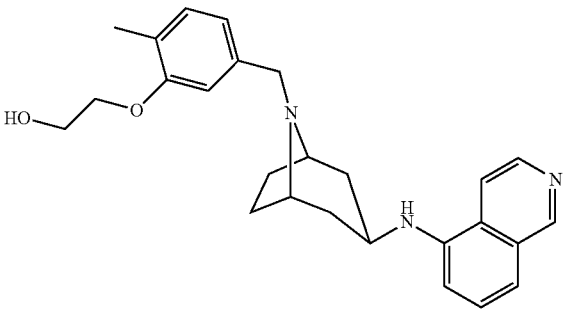<br>2-(5-(((1RS,3sr,5SR)-3-(isoquinolin-5-ylamino)-8-azabicyclo[3.2.1]octan-8-yl)methyl)-2-methylphenoxy)ethanol |
| 3.1.01 | 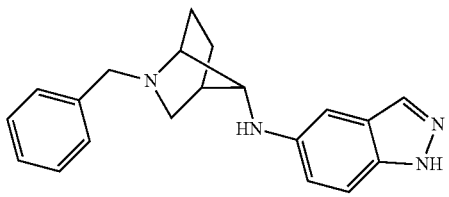<br>N-((1SR,4SR,7RS)-2-benzyl-2-azabicyclo[2.2.1]heptan-7-yl)-1H-indazol-5-amine |

TABLE I-continued

Example Compounds.

| Compound | Structure |
|---|---|
| 3.1.02 | 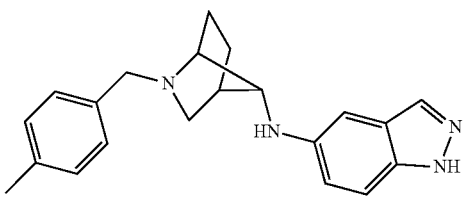<br>N-((1SR,4SR,7RS)-2-(4-methylbenzyl)-2-azabicyclo[2.2.1]heptan-7-yl)-1H-indazol-5-amine |
| 3.1.03 | 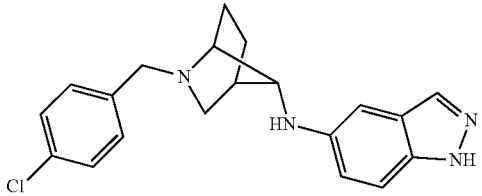<br>N-((1SR,4SR,7RS)-2-(4-chlorobenzyl)-2-azabicyclo[2.2.1]heptan-7-yl)-1H-indazol-5-amine |
| 3.1.04 | 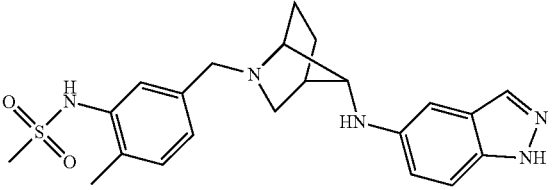<br>N-(5-((((1SR,4SR,7RS)-7-((1H-indazol-5-yl)amino)-2-azabicyclo[2.2.1]heptan-2-yl)methyl)-2-methylphenyl)methanesulfonamide |
| 3.2.01 | 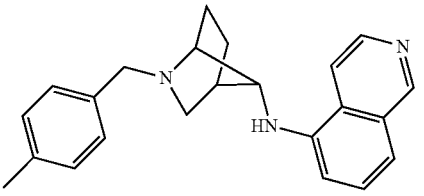<br>N-((1SR,4SR,7RS)-2-(4-methylbenzyl)-2-azabicyclo[2.2.1]heptan-7-yl)isoquinolin-5-amine |
| 3.2.02 | 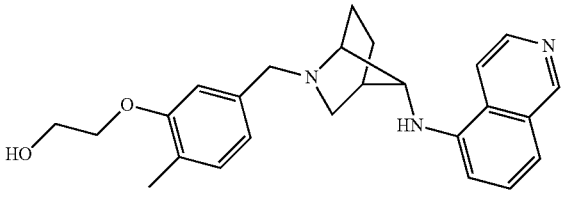<br>2-(5-((((1SR,4SR,7RS)-7-(isoquinolin-5-ylamino)-2-azabicyclo[2.2.1]heptan-2-yl)methyl)-2-methylphenoxy)ethanol |

TABLE I-continued

Example Compounds.

| Compound | Structure |
|---|---|
| 3.3.01 | 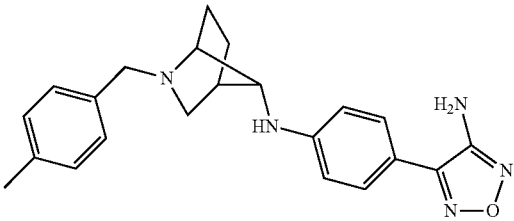<br>4-(4-(((1SR,4SR,7RS)-2-(4-methylbenzyl)-2-azabicyclo[2.2.1]heptan-7-yl)amino)phenyl)-1,2,5-oxadiazol-3-amine |
| 4.1.01 | 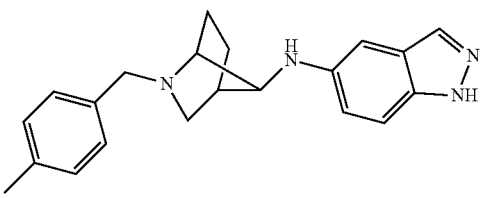<br>N-((1SR,4SR,7SR)-2-(4-methylbenzyl)-2-azabicyclo[2.2.1]heptan-7-yl)-1H-indazol-5-amine |
| 4.1.02 | 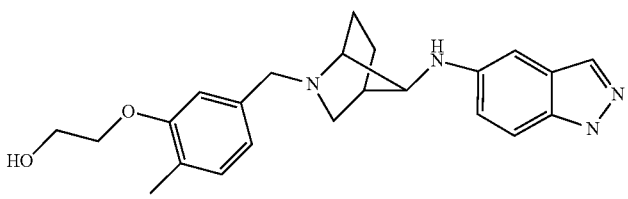<br>2-(5-(((1SR,4SR,7SR)-7-((1H-indazol-5-yl)amino)-2-azabicyclo[2.2.1]heptan-2-yl)methyl)-2-methylphenoxy)ethanol |
| 4.2.01 | 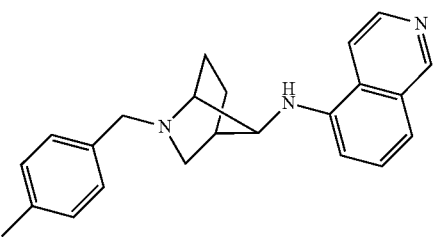<br>N-((1SR,4SR,7SR)-2-(4-methylbenzyl)-2-azabicyclo[2.2.1]heptan-7-yl)isoquinolin-5-amine |
| 4.2.02 | 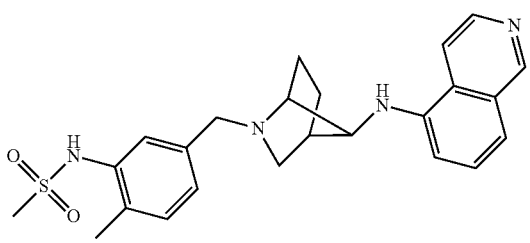<br>N-(5-(((1SR,4SR,7SR)-7-(isoquinolin-5-ylamino)-2-azabicyclo[2.2.1]heptan-2-yl)methyl)-2-methylphenyl)methanesulfonamide |

TABLE I-continued

Example Compounds.

| Compound | Structure |
|---|---|
| 4.2.03 | 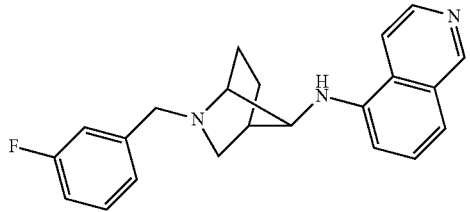<br>N-((1SR,4SR,7SR)-2-(3-fluorobenzyl)-2-azabicyclo[2.2.1]heptan-7-yl)isoquinolin-5-amine |
| 5.1.01 | 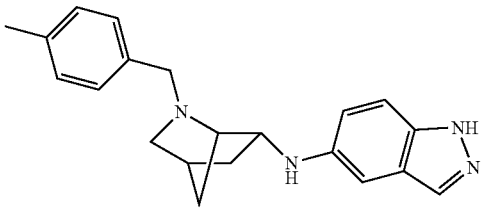<br>N-((1SR,4SR,6SR)-2-(4-methylbenzyl)-2-azabicyclo[2.2.1]heptan-6-yl)-1H-indazol-5-amine |
| 5.1.02 | 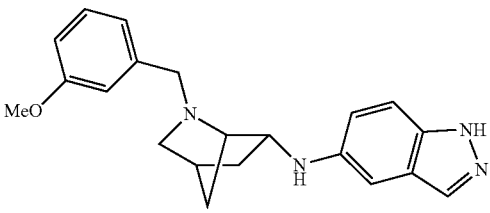<br>N-((1SR,4SR,6SR)-2-(3-methoxybenzyl)-2-azabicyclo[2.2.1]heptan-6-yl)-1H-indazol-5-amine |
| 5.1.03 | 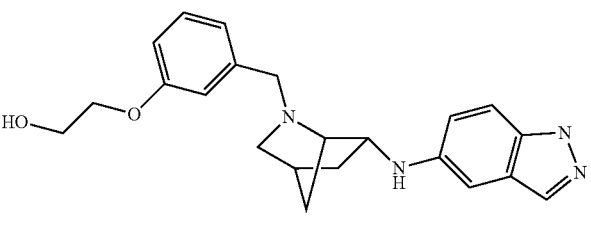<br>2-(3-(((1SR,4SR,6SR)-6-((1H-indazol-5-yl)amino)-2-azabicyclo[2.2.1]heptan-2-yl)methyl)phenoxy)ethanol |
| 5.2.01 | 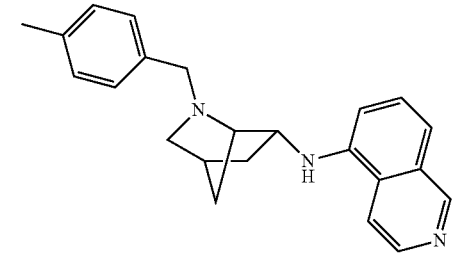<br>N-((1SR,4SR,6SR)-2-(4-methylbenzyl)-2-azabicyclo[2.2.1]heptan-6-yl)isoquinolin-5-amine |

TABLE I-continued

Example Compounds.

| Compound | Structure |
|---|---|
| 5.2.02 | 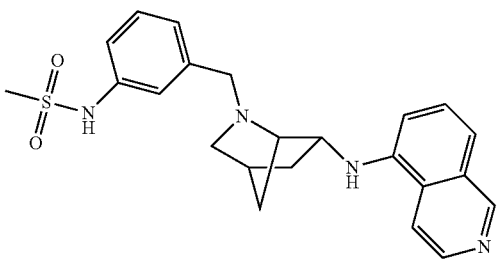<br>N-(3-((((1SR,4SR,6SR)-6-(isoquinolin-5-ylamino)-2-azabicyclo[2.2.1]heptan-2-yl)methyl)phenyl)methanesulfonamide |
| 5.3.01 | 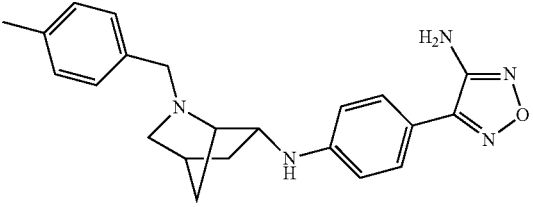<br>4-(4-(((1SR,4SR,6SR)-2-(4-methylbenzyl)-2-azabicyclo[2.2.1]heptan-6-yl)amino)phenyl)-1,2,5-oxadiazol-3-amine |
| 6.1.01 | 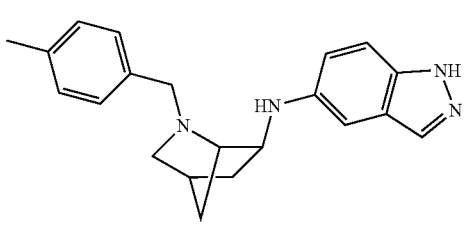<br>N-((1SR,4SR,6RS)-2-(4-methylbenzyl)-2-azabicyclo[2.2.1]heptan-6-yl)-1H-indazol-5-amine |
| 6.1.02 | 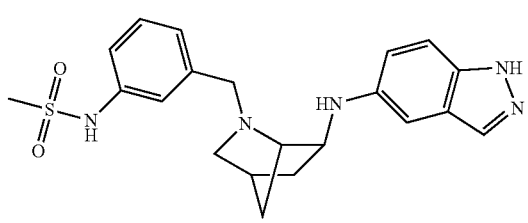<br>N-(3-((((1SR,4SR,6RS)-6-((1H-indazol-5-yl)amino)-2-azabicyclo[2.2.1]heptan-2-yl)methyl)phenyl)methanesulfonamide |
| 6.2.01 | 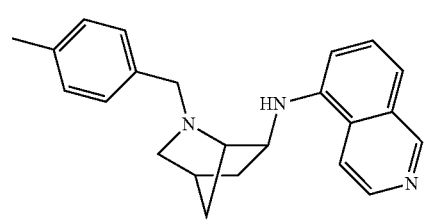<br>N-((1SR,4SR,6RS)-2-(4-methylbenzyl)-2-azabicyclo[2.2.1]heptan-6-yl)isoquinolin-5-amine |

TABLE I-continued

Example Compounds.

| Compound | Structure |
|---|---|
| 6.2.02 | 2-(3-(((1SR,4SR,6RS)-6-(isoquinolin-5-ylamino)-2-azabicyclo[2.2.1]heptan-2-yl)methyl)phenoxy)ethanol |
| 6.2.03 | N-((1SR,4SR,6RS)-2-(4-methoxybenzyl)-2-azabicyclo[2.2.1]heptan-6-yl)isoquinolin-5 amine |
| 6.3.01 | 4-(4-(((1SR,4SR,6RS)-2-(4-methylbenzyl)-2-azabicyclo[2.2.1]heptan-6-yl)amino)phenyl)-1,2,5-oxadiazol-3-amine |
| 7.1.01 | N-((1RS,4RS,5SR)-2-(4-methylbenzyl)-2-azabicyclo[2.2.1]heptan-5-yl)-1H-indazol-5-amine |
| 7.1.02 | 2-(5-(((1RS,4RS,5SR)-5-((1H-indazol-5-yl)amino)-2-azabicyclo[2.2.1]heptan-2-yl)methyl)-2-methylphenoxy)ethanol |

TABLE I-continued

Example Compounds.

| Compound | Structure |
|---|---|
| 7.1.03 | 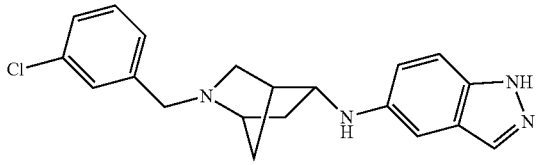
N-((1RS,4RS,5SR)-2-(3-chlorobenzyl)-2-azabicyclo[2.2.1]heptan-5-yl)-1H-indazol-5-amine |
| 7.2.01 | 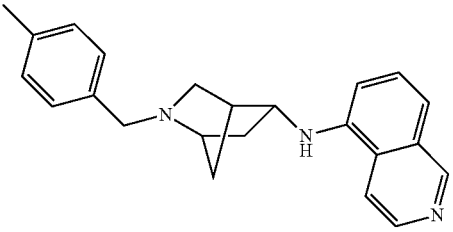
N-((1RS,4RS,5SR)-2-(4-methylbenzyl)-2-azabicyclo[2.2.1]heptan-5-yl)isoquinolin-5-amine |
| 7.2.02 | 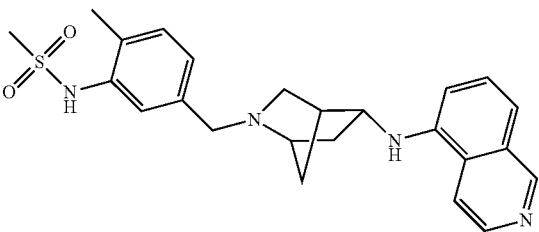
N-(5-(((1RS,4RS,5SR)-5-(isoquinolin-5-ylamino)-2-azabicyclo[2.2.1]heptan-2-yl)methyl)-2-methylphenyl)methanesulfonamide |
| 8.1.01 | 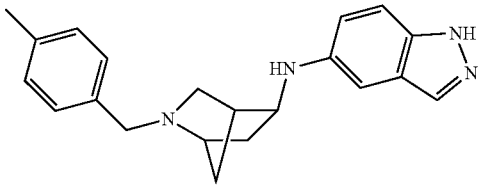
N-((1RS,4RS,5RS)-2-(4-methylbenzyl)-2-azabicyclo[2.2.1]heptan-5-yl)-1H-indazol-5-amine |
| 8.1.02 | 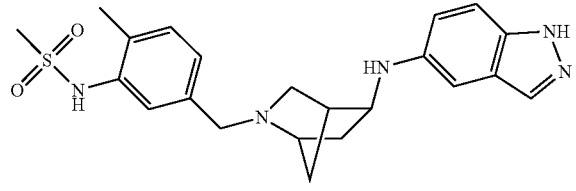
N-(5-(((1RS,4RS,5RS)-5-((1H-indazol-5-yl)amino)-2-azabicyclo[2.2.1]heptan-2-yl)methyl)-2-methylphenyl)methanesulfonamide |

TABLE I-continued
Example Compounds.
| Compound | Structure |
|---|---|
| 8.2.01 | 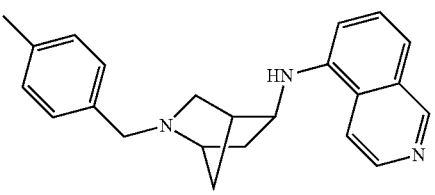<br>N-((1RS,4RS,5RS)-2-(4-methylbenzyl)-2-azabicyclo[2.2.1]heptan-5-yl)isoquinolin-5-amine |
| 8.2.02 | 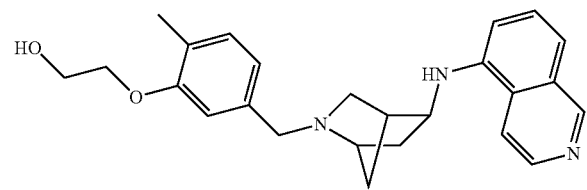<br>2-(5-((((1RS,4RS,5RS)-5-(isoquinolin-5-ylamino)-2-azabicyclo[2.2.1]heptan-2-yl)methyl)-2-methylphenoxy)ethanol |
| 8.2.03 | 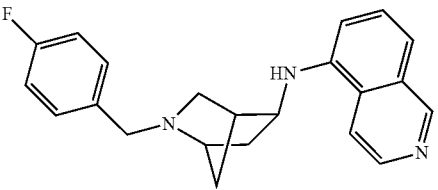<br>N-((1RS,4RS,5RS)-2-(4-fluorobenzyl)-2-azabicyclo[2.2.1]heptan-5-yl)isoquinolin-5-amine |
| 9.1.01 | 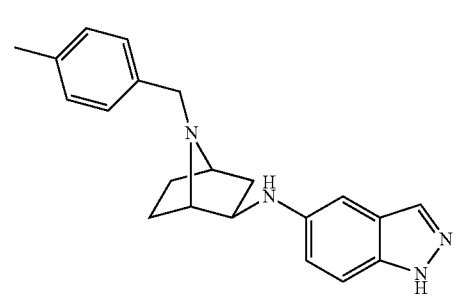<br>N-((1SR,2RS,4RS)-7-(4-methylbenzyl)-7-azabicyclo[2.2.1]heptan-2-yl)-1H-indazol-5-amine |

TABLE I-continued

Example Compounds.

| Compound | Structure |
|---|---|
| 9.1.02 | 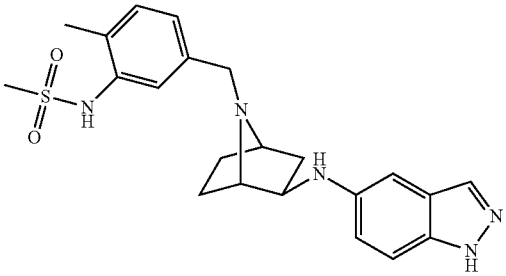<br>N-(5-((((1SR,2RS,4RS)-2-((1H-indazol-5-yl)amino)-7-azabicyclo[2.2.1]heptan-7-yl)methyl)-2-methylphenyl)methanesulfonamide |
| 9.1.03 | 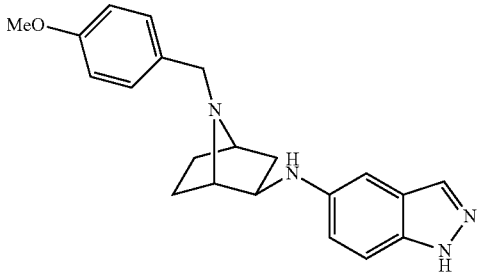<br>N-((1SR,2RS,4RS)-7-(4-methoxybenzyl)-7-azabicyclo[2.2.1]heptan-2-yl)-1H-indazol-5-amine |
| 9.2.01 | 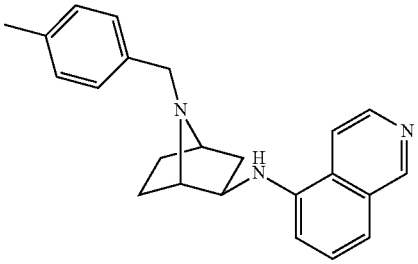<br>N-((1SR,2RS,4RS)-7-(4-methylbenzyl)-7-azabicyclo[2.2.1]heptan-2-yl)isoquinolin-5-amine |
| 9.2.02 | 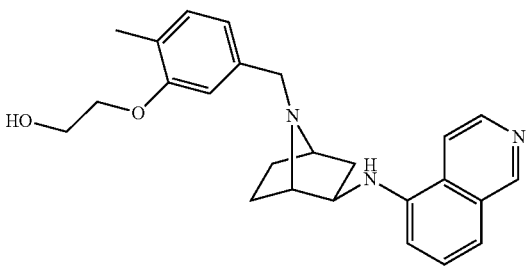<br>2-(5-((((1SR,2RS,4RS)-2-(isoquinolin-5-ylamino)-7-azabicyclo[2.2.1]heptan-7-yl)methyl)-2-methylphenoxy)ethanol |

TABLE I-continued

Example Compounds.

| Compound | Structure |
|---|---|
| 10.1.01 | 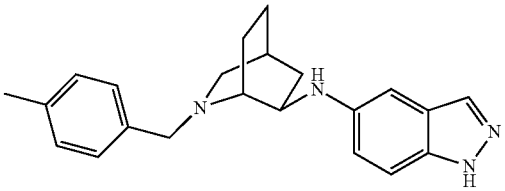<br>(1RS,4SR,6RS)-N-(1H-indazol-5-yl)-2-(4-methylbenzyl)-2-azabicyclo[2.2.2]octan-6-amine |
| 10.1.02 | 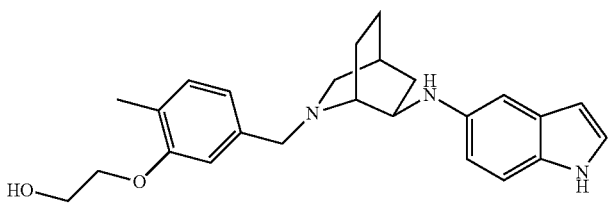<br>2-(5-(((1RS,4SR,6RS)-6-((1H-indazol-5-yl)amino)-2-azabicyclo[2.2.2]octan-2-yl)methyl)-2-methylphenoxy)ethanol |
| 10.2.01 | 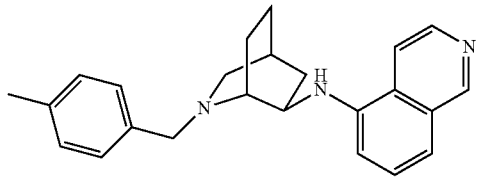<br>(1RS,4SR,6RS)-N-(isoquinolin-5-yl)-2-(4-methylbenzyl)-2-azabicyclo[2.2.2]octan-6-amine |
| 10.2.02 | 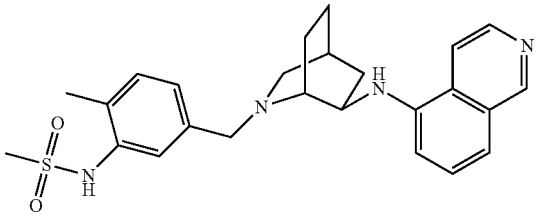<br>N-(5-(((1RS,4SR,6RS)-6-(isoquinolin-5-ylamino)-2-azabicyclo[2.2.2]octan-2-yl)methyl)-2-methylphenyl)methanesulfonamide |
| 10.2.03 | 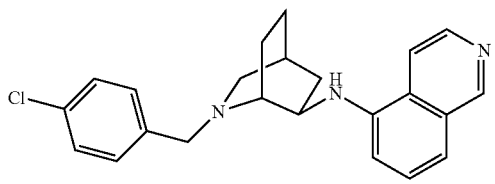<br>(1RS,4SR,6RS)-2-(4-chlorobenzyl)-N-(isoquinolin-5-yl)-2-azabicyclo[2.2.2]octan-6-amine |

TABLE I-continued
Example Compounds.
| Compound | Structure |
|---|---|
| 11.1.01 | 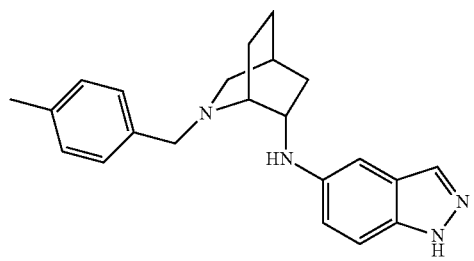<br>(1RS,4SR,6SR)-N-(1H-indazol-5-yl)-2-(4-methylbenzyl)-2-azabicyclo[2.2.2]octan-6-amine |
| 11.1.02 | 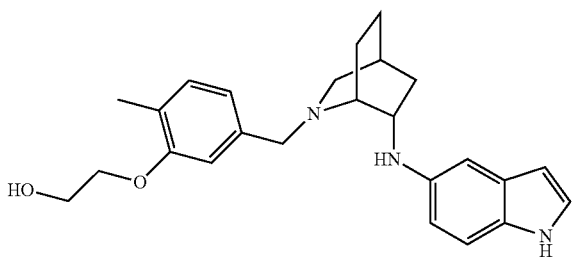<br>2-(5-(((1RS,4SR,6SR)-6-((1H-imdazol-5-yl)amino)-2-azabicyclo[2.2.2]octan-2-yl)methyl)-2-methylphenoxy)ethanol |
| 11.1.03 | 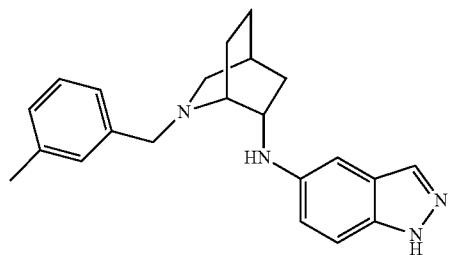<br>(1RS,4SR,6SR)-N-(1H-indazol-5-yl)-2-(3-methylbenzyl)-2-azabicyclo[2.2.2]octan-6-amine |
| 11.2.01 | 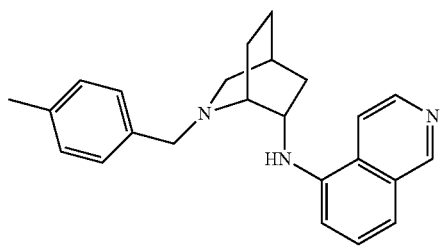<br>(1RS,4SR,6SR)-N-(isoquinolin-5-yl)-2-(4-methylbenzyl)-2-azabicyclo[2.2.2]octan-6-amine |

TABLE I-continued

Example Compounds.

| Compound | Structure |
| --- | --- |
| 11.2.02 | 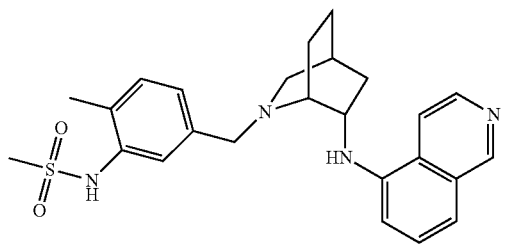
N-(5-((((1RS,4SR,6SR)-6-(isoquinolin-5-ylamino)-2-azabicyclo[2.2.2]octan-2-yl)methyl)-2-methylphenyl)methanesulfonamide |
| 12.1.01 | 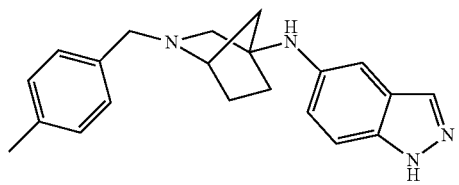
N-(2-(4-methylbenzyl)-2-azabicyclo[2.2.1]heptan-4-yl)-1H-indazol-5-amine |
| 12.1.02 | 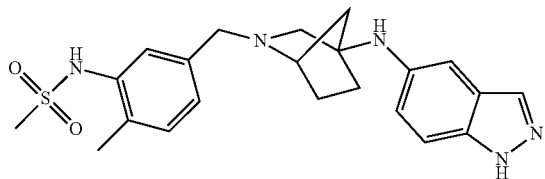
N-(5-((-4-((1H-indazol-5-yl)amino)-2-azabicyclo[2.2.1]heptan-2-yl)methyl)-2-methylphenyl)methanesulfonamide |
| 12.2.01 | 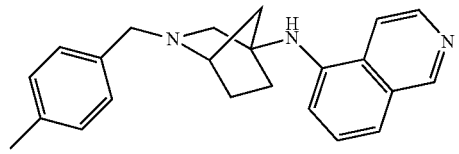
N-(2-(4-methylbenzyl)-2-azabicyclo[2.2.1]heptan-4-yl)isoquinolin-5-amine |
| 12.2.02 | 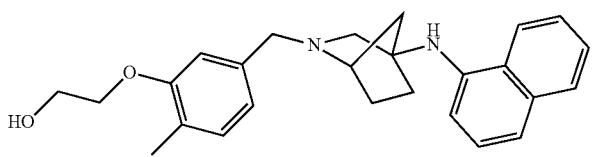
2-(5-((4-(isoquinolin-5-ylamino)-2-azabicyclo[2.2.1]heptan-2-yl)methyl)-2-methylphenoxy)ethanol |

TABLE I-continued

Example Compounds.

| Compound | Structure |
|---|---|
| 12.2.03 | 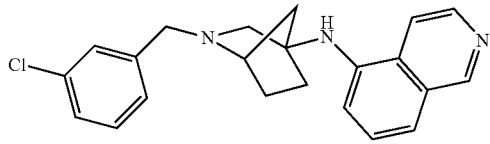<br>N-(2-(3-chlorobenzyl)-2-azabicyclo[2.2.1]heptan-4-yl)isoquinolin-5 amine |
| 13.1.01 | 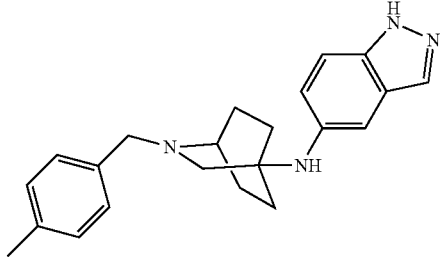<br>N-(1H-indazol-5-yl)-2-(4-methylbenzyl)-2-azabicyclo[2.2.2]octan-4-amine |
| 13.1.02 | 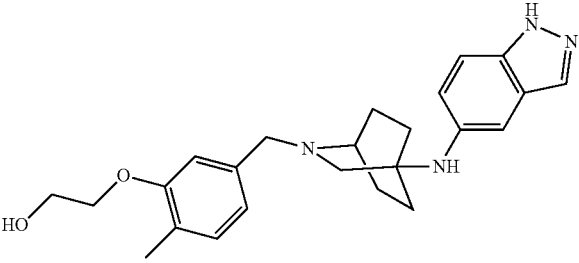<br>2-(5-((4-((1H-indazol-5-yl)amino)-2-azabicyclo[2.2.2]octan-2-yl)methyl)-2-methylphenoxy)ethanol |
| 13.1.03 | 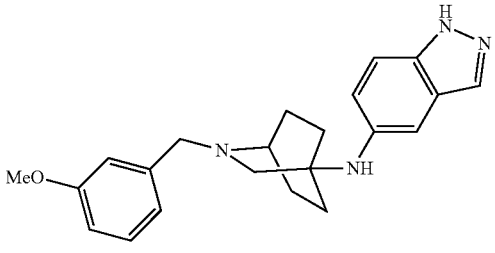<br>N-(1H-indazol-5-yl)-2-(3-methoxybenzyl)-2-azabicyclo[2.2.2]octan-4-amine |
| 13.2.01 | 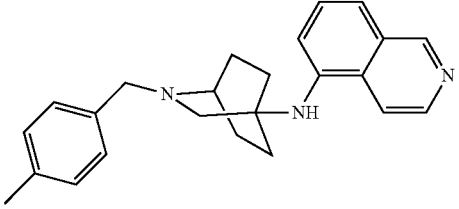<br>N-(isoquinolin-5-yl)-2-(4-methylbenzyl)-2-azabicyclo[2.2.2]octan-4-amine |

TABLE I-continued

Example Compounds.

| Compound | Structure |
|---|---|
| 13.2.02 | 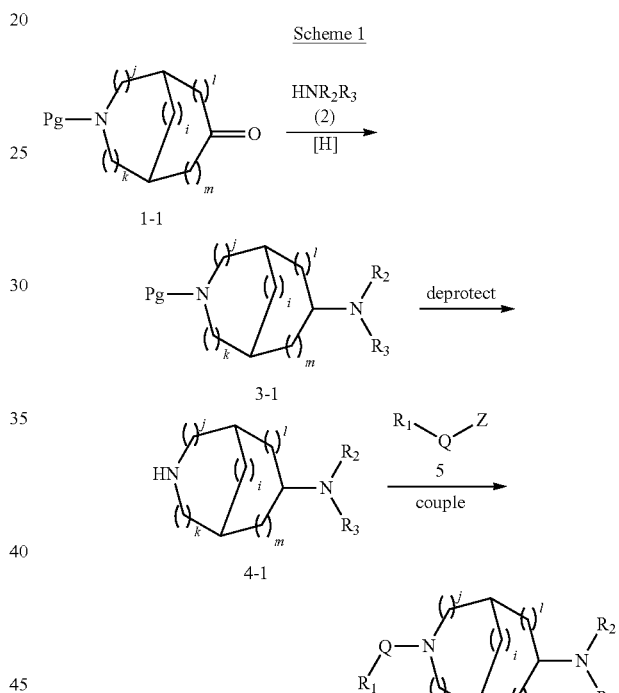<br>N-(5-((4-(isoquinolin-5-ylamino)-2-azabicyclo[2.2.2]octan-2-yl)methyl)-2-methylphenyl)methanesulfonamide |

Preparation of Compounds of Formula I

The present invention is additionally directed to procedures for preparing compounds of Formula I. General approaches for preparations of the compounds of the Formula are described in Scheme 1 and Scheme 2. Those having skill in the art will recognize that the starting materials can be varied and additional steps can be employed to produce compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

Those skilled in the art will recognize various synthetic methodologies that can be employed to prepare non-toxic pharmaceutically acceptable prodrugs, for example acylated prodrugs, of the compounds of this invention.

Compounds of Formula I in which the bicyclic ring subunit is ring-1 or ring-2 can be prepared starting from protected heterocyclic ketones 1-1 and 1-2, respectively. The preparation is described in Scheme 1, using 1-1 as the example; an equivalent preparation can be carried out starting with compound 1-2.

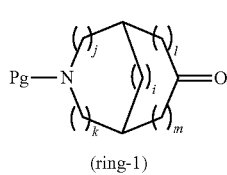
(ring-1)

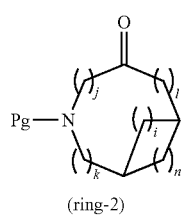
(ring-2)

In Scheme 1, the protected heterocyclic ketone 1-1 is treated with an amine 2 under reductive amination conditions, typically using a borohydride reducing agent such as sodium cyanoborohydride or sodium triacetoxyborohydride. The resulting protected diamine 3-1 is deprotected using conditions appropriate to the choice of protecting group, for example, acid conditions for a BOC protecting group or reductive conditions for a CBZ group. The deprotected product 4-1 is then coupled with a coupling partner 5 with functionality Q-Z that is suitable for introducing the substituent $R_1$-Q. Typical example coupling reactions with 5 include reductive amination with an aldehyde, alkylation with an alkyl halide, and acylation with an acyl halide or sulfonyl halide. This coupling reaction provides compound 6-1, an example of the substances described by Formula 1.

Compounds of Formula I can also be prepared starting from protected diamines 7-1, 7-2, and 7-3, to provide compounds in which the bicyclic ring subunit ring-1, ring-2, and ring-3, respectively. The preparation is described in Scheme 2, using 7-1 as the example; equivalent preparations can be carried out starting with compounds 7-2 and 7-3.

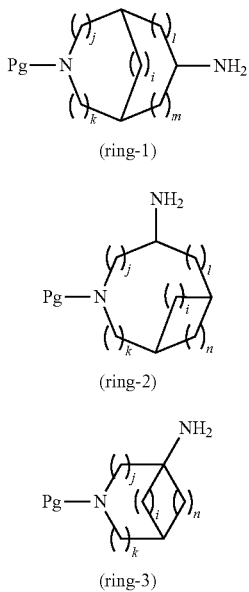

Scheme 2

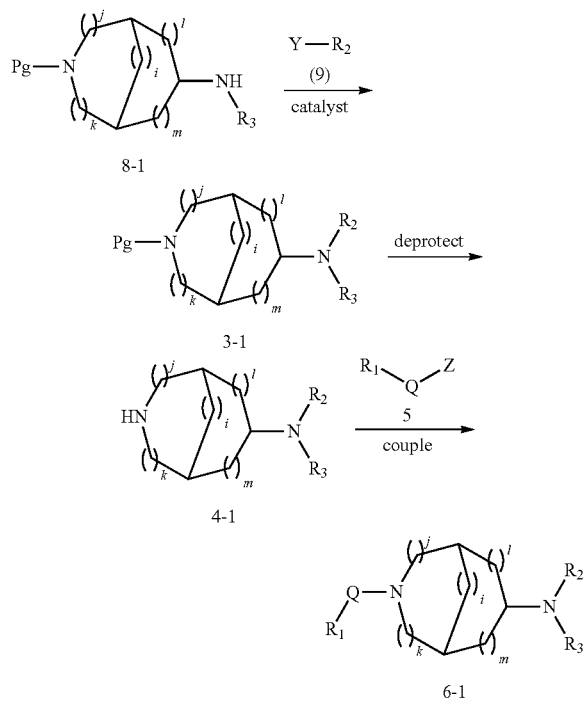

In Scheme 2, the protected diamine 8-1, can be made from amine 7-1 using methods well known in the literature, such as reductive amination with an aldehyde or a ketone, and alkylation with an alkyl halide. The protected diamine 8-1 is allowed to react with a suitably activated form of the substituent $R_2$, 9, optionally in the presence of a catalyst. Example activating groups Y include halides and triflates, and palladium catalysts are typically used. This coupling reaction produces the protected diamine product 3-1, which is analogous to protected diamine 3-1 in Scheme 1, and which is elaborated in the same sequence of transformations to yield 6-1, an example of the substances described by the Formulae.

As protected diamines 7-1, 7-2, and 7-3 have the stereocenter at the point of connection for $NR_2R_3$ well defined, Scheme 2 methods provide a better control of the stereocenter, thus provide a better control of the stereochemistry of the end product. It will be seen that modifications of the above two synthetic schemes using well-known procedures will allow the preparation of other members in the scope of the Formula.

Appropriate protection of interfering function groups can be important for obtaining satisfactory reaction of protected diamines 8 with the activated $R_2$ subunit 9. In particular, when $R_2$ is indazolyl, protection of any unsubstituted indazole nitrogen is critical to the success of the reaction. Preferred protecting groups in this situation are p-methoxybenzyl (PMB) and 2-tetrahydropyranyl (THP), with THP being most preferred. Use of the THP protecting group provides high yields in the protection, coupling, and deprotection steps, and allows the protecting group to be removed without the need for scavenger reagents, which are otherwise needed for clean deprotection.

The starting materials required for the preparations described in Schemes 1 and 2 can be obtained commercially or can be prepared by methods well known in the chemical literature. In particular, compounds of the general form given in ketones 1-1 and 1-2, and amines 7-1, 7-2, and 7-3 can be prepared from naturally occurring substances containing the desired ring systems or closely related systems. These compounds can also be prepared using a wide variety of well-known ring forming reactions, for example the Diels-Alder, ring-closing metathesis, Dieckmann, and intramolecular alkylation, acylation, Mannich, and aldol reactions. Many of these materials have been reported in the literature, for example in A. Gayet and P. G. Andersson, *Adv. Synth. Catal.* 2005, 347, 1242-1246, J. Malpass and C. Cox, *Tetrahedron Lett.,* 1999, 40, 1419-1422, I. Iriepa et al., *Bioorg. Med. Chem. Lett.* 2002, 12, 189-192, M. P. Cava et al., *J. Org. Chem.* 1965, 30, 3772-3775, U.S. Pat. No. 5,147,873, WO07110782, WO03022856, U.S. Pat. No. 5,852,037, WO04013137, WO04074292, and WO04052348.

Those skilled in the art of chemical synthesis will understand that the example preparations listed above can be extended to provide other compounds of the general form shown in compounds 1-1, 1-2, 7-1, 7-2, and 7-3, for example, by using in the preparations starting materials which are similar to those described in the example preparations but which have larger or smaller rings and/or chains than the specific starting materials used in the examples. Additionally, it will be understood that the example starting materials can be converted into other closely related useful starting materials by applying well-known transformations to the materials, for example ring expansion and ring contraction transformations.

It will be further understood that starting materials of the form given in general compounds 1-1, 1-2, 7-1, 7-2, and 7-3 can be prepared from related compounds of the form 10-1, 10-2, and 10-3, shown below, in which FG indicates a functional group such as $CO_2H$, CN, $NO_2$, OH, or halogen, or related compounds containing an olefin in the bicyclic ring system, which can be converted into a carbonyl or an amine.

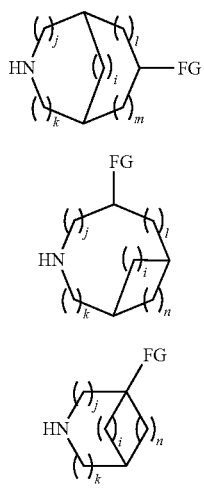

Pharmaceutical Composition and Use

The present invention provides a pharmaceutical formulation comprising compounds of Formula I and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation useful for the present invention in general is an aqueous solution comprising water, suitable ionic or non-ionic tonicity modifiers, suitable buffering agents, and a compound of Formula I. In one embodiment, the compound is at 0.005 to 3% w/v, and the aqueous solution has a tonicity of 200-400 mOsm/kG and a pH of 4-9.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 4-5% w/v.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to systemic administration.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or acetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions can also contain sweetening and flavoring agents.

Pharmaceutical compositions of the invention can be in the form of an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

The pharmaceutical formulation for systemic administration such as injection and infusion is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diluent or solvent. Among the acceptable vehicles and solvents that can be employed are sterile water, saline solution, or Ringer's solution.

The pharmaceutical compositions for oral administration contain active compounds in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

The pharmaceutical compositions can be in the form of suppositories, which are prepared by mixing the active ingredient with a suitable non-irritating excipient that is solid at ordinary temperatures but liquid at the rectal temperature and will thus melt in the rectum to release the active ingredient.

In one embodiment of the invention, the compositions are formulated as topical ophthalmic preparations, with a pH of about 3-9, preferably 4 to 8. The compounds of the invention are generally contained in these formulations in an amount of at least 0.001% by weight, for example, 0.001% to 5% by weight, preferably about 0.003% to about 2% by weight, with an amount of about 0.02% to about 1% by weight being most preferred. For topical administration, one to two drops of these formulations are delivered to the surface of the eye one to four times per day according to the routine discretion of a skilled clinician.

The delivery of such ophthalmic preparations may be done using a single unit dose vial wherein the inclusion of a preservative may be precluded. Alternatively, the ophthalmic preparation may be contained in an ophthalmic dropper container intended for multi-use. In such an instance, the multi-use product container may or may not contain a preservative, especially in the event the formulation is self-preserving. Furthermore, the dropper container is designed to deliver a certain fixed volume of product preparation in each drop. The typical drop volume of such an ophthalmic preparation will range from 20-60 microliters, preferably 25-55 microliters, more preferably 30-50 microliters, with 35-50 microliters being most preferred.

The inventors of the present invention have discovered that compounds of Formula I are useful in preventing or treating diseases or conditions associated with cellular relaxation and/or changes in cell-substratum adhesions by altering cellular integrity or by rearrangement of the cytoskeleton, including but not exclusive of actomyosin interactions, tight junctional and focal adhesion complexes.

By resolving one or more of the above-described pathophysiologies, the present invention provides a method of treating ocular diseases such as glaucoma, modulation of wound healing after trabeculectomy, posterior capsule opacification (PCO), angiogenesis-associated ophthalmic diseases, modulating fluid transport on the ocular surface and retinal vasospasm.

Glaucoma

Glaucoma is an ophthalmic disease that leads to irreversible visual impairment. Primary open-angle glaucoma is characterized by abnormally high resistance to fluid (aqueous humor) drainage from the eye. Cellular contractility and changes in cell-cell and cell-trabeculae adhesion in the trabecular meshwork are major determinants of the resistance to flow. The compounds of the present invention cause a transient, pharmacological perturbation of both cell contractility and cell adhesions, mainly via disruption of the actomyosin-associated cytoskeletal structures and/or the modulation of their interactions with the membrane. Altering the contractility of trabecular meshwork cells leads to drainage-surface expansion. Loss of cell-cell, cell-trabeculae adhesion may influence paracellular fluid flow across Schlemm's canal or alter the fluid flow pathway through the juxtacanalicular tissue of the trabecular meshwork. Both mechanisms likely reduce the resistance of the trabecular meshwork to fluid flow and thereby reduce intraocular pressure in a therapeutically useful manner.

Modulation of Wound Healing after Trabeculectomy, Posterior Capsule Opacification (PCO), Angiogenesis-Associated Ophthalmic Diseases, Modulating Fluid Transport on the Ocular Surface and Retinal Vasospasm The compounds of the present invention are useful for modulation of wound healing after trabeculectomy. The compounds in general are less toxic to both corneal epithelial and endothelial cells than the antimetabolites such as 5-fluorouracil or mitomycin C. The compounds inhibit actomyosin-driven contractility, leading to deterioration of the actin microfilament system and perturbation of its membrane anchorage, which weakens the cell-extracellular matrix adhesions. These properties inhibit wound healing and thereby reduce bleb failure following the surgery.

A frequent complication of extracapsular cataract extraction and intraocular lens (IOL) implantation is posterior capsule opacification (PCO); a type of secondary cataract caused by residual epithelial cells following lens removal. Perturbation of the actin cytoskeleton and focal adhesions through Rho kinase inhibition may facilitate surgical removal of all cells from the capsular bag and thereby reduce PCO.

Angiogenesis is characterized by the development of new vasculature from pre-existing vessels and plays a central role in physiological processes such as embryogenesis, wound healing and female reproductive function, as well as pathophysiologic events including cancer, rheumatoid arthritis and diabetic retinopathy. The growth and metastasis of tumors is critically dependent upon angiogenesis. Angiogenesis is a multistep process involving the endothelial cell (EC) cytoskeleton in migration, proliferation, and barrier stabilization. Angiogenesis is also involved in several ocular diseases such as age-related macular degeneration, diabetic retinopathy, retinopathy of prematurity, corneal angiogenesis, choroidial neovascularization, neovascular, glaucoma, ocular tumorigenesis. Applicants believe that interactions between the cytoskeleton and apoptosis are involved in the intracellular pathways by which angiogenic tube formation occurs. The compounds of the present invention are useful in inhibiting angiogenesis and treating tumors and angiogenesis-associated ophthalmic diseases.

Regulation of the actin cytoskeleton is important in the modulation of fluid transport. Antimitotic drugs markedly interfere with antidiuretic response, strongly implying that cytoskeleton integrity is essential to this function. This role of the cytoskeleton in controlling the epithelial transport is a necessary step in the translocation of the water channel containing particle aggregates and in their delivery to the apical membrane. Osmolality-dependent reorganization of the cytoskeleton and expression of specific stress proteins are important components of the regulatory systems involved in the adaptation of medullary cells to osmotic stress. The compounds of the present invention are useful in directing epithelial function and modulating fluid transport, particularly modulating fluid transport on the ocular surface.

Rho-associated protein kinase inhibitors, due to their regulation of smooth muscle contractility, are useful in the treatment of vasospasm, specifically retinal vasospasm. Relaxation of retinal vasculature increases perfusion rates thereby providing a neuroprotective mechanism (decreased apoptosis and necrosis) in retinal diseases and retinopathies such as glaucoma, ocular hypertension, age-related macular degeneration or retinitis pigmentosa. Additionally, these kinase inhibitors regulate vascular endothelial permeability and as such can play a vasoprotective role to various atherogenic agents.

The present invention provides a method of reducing intraocular pressure, including treating glaucoma such as primary open-angle glaucoma; a method of treating constriction of the visual field; a method of inhibiting wound healing after trabeculectomy; a method of treating posterior capsule opacification following extracapsular cataract extraction and intraocular lens implantation; a method of inhibiting angiogenesis; a method of modulating fluid transport on the ocular surface; a method of controlling vasospasm; a method of increasing tissue perfusion; a method of neuroprotection; and a method of vasoprotection to atherogenic agents. The method comprises the steps of identifying a subject in need of treatment, and administering to the subject a compound of Formula I, in an amount effective to alter the actin cytoskeleton, such as by inhibiting actomyosin interactions.

The inventors of the present invention have also discovered that compounds of Formula I are effective Rho kinase inhibitors and are therefore effective in reducing cell proliferation, decreasing remodeling that is defined by cell migration and/or proliferation, reducing inflammation via the inhibition of leukocytes chemotaxis and the inhibition of cytokine and chemokine secretion, lowering or preventing tissue or organ edema via the increase of endothelial cell junction integrity, and reducing neurite retraction and promoting neuro-regeneration via the disruption of acto-myosin-based cytoskeleton within sensory neurons. By having the above properties, compounds of Formula I are useful in a method of preventing or treating diseases or conditions associated with excessive cell proliferation, remodeling, inflammation, vasoconstriction, bronchoconstriction, neural densitization/degeneration and vascular edema.

By resolving one or more of the above-described pathophysiologies, the present invention provides a method of treating ocular diseases, particularly allergic conjunctivitis, corneal neuritogenesis, dry eye, proliferative vitreal retinopathy, macular edema and degeneration, and blepharitis.

Allergic Conjunctivitis

The inventors have discovered that compounds of Formula I are inhibitors of Rho kinase and are therefore useful in treating the defects in inflammation seen in allergic conjunctivitis.

The present invention is directed to a method of treating allergic conjunctivitis. The method comprises the steps of first identifying a subject suffering from allergic conjunctivitis, then administering to the subject an effective amount of a compound of Formula I to treat allergic conjunctivitis.

Indicia of efficacy for allergic conjunctivitis include demonstrable improvement in measurable signs, symptoms and other variables clinically relevant to this condition. Specifically, an improving effect on the signs and symptoms of allergic conjunctivitis include itching, tearing, conjunctival edema, hyperemia, watery discharge, burning, and photophobia and eyelid edema. Restoration of normal blink frequency, improved tear film stability, improvement in corneal staining, improvement in tear volume as determined by Schirmer scores, improvement in ocular surface discomfort, increased visual acuity, restoration of normal corneal function (corneal fluid transport and corneal thickness), increased success in maintaining refractive index of cornea following refractive procedure, decreased conjunctival hyperemia, decreased reliance on ocular palliative treatments (artificial tears), decreases need for topical/systemic analgesics, decreased incidence of dry eye disease, decreased ocular surface inflammation (cytokines and pro-inflammatory mediators) and decreased doctor visits are expected.

Corneal Hyposensitivity and Keratopathy

The inventors have discovered that compounds of Formula I are inhibitors of Rho kinase and are therefore useful in treating neurite retraction and neurodegeneration seen in corneal hyposensitivity following PRK and LASIK procedures and neuroparalytic keratopathy, corneal ulcer, and diabetic keratopathy.

The present invention is directed to a method of treating corneal hyposensitivity and keratopathy. The method comprises the steps of first identifying a subject suffering from corneal hyposensitivity and keratopathy, then administering to the subject an effective amount of a compound of Formula I to treat corneal hyposensitivity and keratopathy.

Indicia of efficacy for corneal hyposensitivity and keratopathy include demonstrable improvement in measurable signs, symptoms and other variables clinically relevant to corneal hyposensitivity. Since the pharmaceutical agent of the present invention has a corneal neuritogenesis promoting effect, it is useful for improvement of hypofunction of corneal sensitivity due to damaged corneal nerve and the like, as well as improvement of dry eye associated with hypofunction of corneal sensitivity. Improvements include increased corneal sensitivity, increased corneal epithelial wound healing rate, restoration of normal blink frequency, improved tear film stability, improvement in corneal staining, improvement in tear volume as determined by Schirmer scores, improvement in ocular surface discomfort, improved quality of life, increased visual acuity, restoration of normal corneal function (corneal fluid transport and corneal thickness), increased success in maintaining refractive index of cornea following refractive procedure, decreased conjunctival hyperemia, decreased reliance on ocular palliative treatments (artificial tears), decreases need for topical/systemic analgesics, decreased incidence of dry eye disease, decreased ocular surface inflammation (cytokines and proinflammatory mediators) and decreased doctor visits.

Dry Eye

The inventors have discovered that compounds of Formula I inhibit Rho kinase and therefore are useful for the regulation of chemotaxis, cytokinesis, cytokine and chemokine secretion and inflammation seen in dry eye disease.

The present invention is directed to a method of treating dry eye. The method comprises the steps of first identifying a subject suffering from dry eye, then administering to the subject an effective amount of a compound of Formula I to treat dry eye.

A method for treating dry eye is based on the properties of the Formula I compounds to reduce inflammation that accompany this disorder.

Indicia of efficacy for treating dry eye by the present method include demonstrable improvement in measurable signs, symptoms and other variables clinically relevant to dry eye. Such improvements include reducing the evaporation rate of normal or artificial tears, minimizing the loss of tears, maximizing the preservation of tears, increasing tear film stability, decreasing tear film osmolarity, increasing tear volume, increasing tear secretion, decreasing tear break-up time, decreasing immune-mediated inflammation, increasing gland function, decreasing irritation and itching, decreasing grittiness, decreasing foreign body sensation, increasing aqueous component of tears, decreasing photophobia, decreasing accumulation of mucus filaments, decreasing punctate conjunctival and corneal damage, inducing contraction of the bulbar conjunctival vessels, decreasing dullness of the conjunctiva and cornea, decreasing corneal punctate fluorescein staining, reducing symptoms of blurred vision, increasing secretion of natural anti-inflammatory factors and decreasing production of pro-inflammatory cytokines and proteolytic enzymes. Ophthalmic formulations containing compounds of Formula I, that inhibit RHO KINASE-mediated regulation of certain secreted pro-inflammatory factors and thus improve tear production and tear break up time by reducing immune-mediated inflammation, would clinically lead to decreased irritation and itching, decreased grittiness and foreign body sensation, decreased photophobia, a measurable decrease in corneal damage, contraction of the bulbar conjunctival vessels, decrease in corneal punctate fluorescein staining and reduced symptoms of blurred vision. Inspire's Rho kinase inhibitor compounds have the potential to provide a novel mechanism for the treatment of Dry Eye.

Macular Edema and Degeneration

The inventors have discovered that compounds of Formula I inhibit Rho kinase and therefore are useful in the treating the dysregulation of chemotaxis, cytokinesis, cytokine and chemokine secretion, proliferation, cell motility, endothelial integrity, inflammation, excessive cell proliferation, remodeling, tissue edema, angiogenesis, vascular permeability, endothelial cell invasion and remodeling seen in macular edema and degeneration.

The present invention is directed to a method of treating macular edema and degeneration. The method comprises the steps of first identifying a subject suffering from macular edema and degeneration, then administering to the subject an effective amount of a compound of Formula I to treat macular edema and degeneration.

A method for treating macular edema and degeneration is based on the properties of the Formula I compounds to reduce at least one of the following processes contributing to pathophysiologies that accompany this disorder: inflammation, excessive cell proliferation, remodeling, tissue edema, angiogenesis, vascular permeability, endothelial cell invasion and remodeling.

Indicia of efficacy for treating macular edema and degeneration by the present method include demonstrable improvement in measurable signs, symptoms and other variables clinically relevant to macular edema and degeneration. Indicia of efficacy for macular edema and degeneration include increased or maintained central vision, reduction of blurred vision, enhanced visual acuity, decreased metamorphopsia, reduced or absent central scotomas, reduced sensitivity to glare, increased contrast sensitivity, increased color vision, decreased macular inflammation, decreased fluid retention in the macula, decreased macular swelling, decreased onset or prevention of retinal neovasculature, decreased macular drusen formation, maintenance or decrease in Bruch's membrane thickness.

Proliferative Vitreal Retinopathy

The inventors have discovered that compounds of Formula I inhibit Rho kinase and therefore useful in treating the Rho kinase-mediated regulation of focal adhesions, remodeling, proliferation, and contractility, excessive cell proliferation, adhesion and cellular contractility seen in PVR.

The present invention is directed to a method of treating PVR. The method comprises the steps of first identifying a subject suffering from PVR, then administering to the subject an effective amount of a compound of Formula I to treat PVR.

A method for treating PVR is based on the properties of the Formula I compounds to reduce at least one of the following processes contributing to pathophysiologies that accompany this disorder: excessive cell proliferation, remodeling, adhesion and contractility. Indicia of efficacy of proliferative vitreoretinopathy include: reduction in the frequency of failed surgical outcomes to repair rhegmatogenous retinal detachment; reduction in vitreous flare and pigment clumps in vitreous; ability to correct PVR through pharmacological, non-surgical intervention; improvement in vision central and peripheral vision following RRD surgery; reduction in ocular hypotony; and reduction in macular pucker following retinal detachment surgery.

Blepharitis

The inventors have discovered that compounds of Formula I inhibit Rho kinase and are therefore useful in treating the Rho kinase-mediated regulation of chemotaxis, cytokinesis, cytokine and chemokine secretion, proliferation, cell motility and endothelial integrity, inflammation, excessive cell proliferation, remodeling and tissue edema seen in blepharitis.

The present invention is directed to a method of treating blepharitis. The method comprises the steps of first identifying a subject suffering from blepharitis, then administering to the subject an effective amount of a compound of Formula I to treat blepharitis.

A method for treating blepharitis is based on the properties of the Formula I compounds to reduce at least one of the following processes contributing to pathophysiologies that accompany this disorder: inflammation, excessive cell proliferation, remodeling and tissue edema.

Indicia of efficacy for treating blepharitis by the present method include demonstrable improvement in measurable signs, symptoms and other variables clinically relevant to blepharitis. Such improvements include elimination of redness, swelling, burning, watering, and itching of the eyelids; decrease in flaking and debris accumulation on the eyelashes; decrease in a foreign body sensation; crusting and closure of eyelids upon waking; attenuation of abnormal growth or loss of lashes; decrease in pain sensation and sensitivity to light; a decrease in the incidence of associated complications such as styes, chalzions, dry eye, meibomitis, keratitis, and recurrent conjunctivitis; and heightened sense of well being and self-confidence along with an enhanced ability to carry out daily life activities.

An effective amount of a Formula I compound is administered to a patient in need of treatment for allergic conjunctivitis, corneal neuritogenesis, dry eye, proliferative vitreal retinopathy, macular edema and degeneration, or blepharitis. The patient either already has the symptoms of at least one above-mentioned disease, or is identified as being at risk of at least one above-mentioned disease. The compound is administered at a frequency that achieves desired efficacy. What constitutes desired efficacy is determined by a physician or other health-care professional. Whether or not sufficient efficacy has been reached is determined by indicia of efficacy for the specific disease. After an initial dose, additional doses are optionally administered if judged to be necessary by a health-care professional.

The inventors of the present invention have discovered that compounds of Formula I are effective Rho kinase inhibitors and are therefore effective in treating lung diseases in that they are effective in reducing cell proliferation, decreasing remodeling that is defined by cell migration and/or proliferation, reducing inflammation via the inhibition of leukocytes chemotaxis and the inhibition of cytokine and chemokine secretion, lowering or preventing tissue or organ edema via the increase of endothelial cell junction integrity, reducing vasoconstriction, bronchoconstriction and airway hyperreactivity via the disruption of acto-myosin-based cytoskeleton within smooth muscle cells, thereby reducing smooth muscle tone and contractibility, and preventing airway hyperreactivity by reducing the inflammatory response. By having the above properties, compounds of Formula I are useful in a method of preventing or treating diseases or conditions of the lung associated with excessive cell proliferation, remodeling, inflammation, vasoconstriction, bronchoconstriction, airway hyperreactivity and edema.

The invention provides a method of reducing excessive cell proliferation, a method of decreasing remodeling that is defined by cell migration and/or proliferation, a method of reducing inflammation via inhibition of leukocytes chemotaxis and via decreasing cytokine and chemokine secretion, a method of lowering or preventing tissue or organ edema via increasing endothelial and epithelial cell junction integrity, a method of reducing vasoconstriction, bronchoconstriction and airway hyperreactivity via disruption of acto-myosin-based cytoskeleton within smooth muscle cells and thus reducing smooth muscle tone and contractibility, and a method of preventing airway hyperreactivity by reducing the inflammatory response. By resolving one or more of the above-described pathophysiologies, the present invention provides a method of treating pulmonary diseases, particularly asthma, COPD, respiratory tract illness caused by respiratory syncytial virus infection such as RSV-induced wheezing and hyperreactivity or bronchiolitis, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP.

Asthma

The inventors have discovered that Compounds of Formula I are effective Rho kinase inhibitors and therefore inhibit the Rho kinase-mediated regulation of chemotaxis, cytokinesis, cytokine and chemokine secretion, proliferation, cell motility, endothelial integrity and/or smooth muscle contraction. Furthermore, the inventors have discovered that Compounds of Formula I are useful in treating the defects in inflammation, pulmonary neutrophilia and eosinophilia, excessive cell proliferation, remodeling, airway and/or lung tissue edema, airway hyperreactivity or bronchoconstriction as well as preventing the development of airway hyperreactivity seen in asthma The present invention is directed to a method of treating asthma. The method comprises the steps of first identifying a subject suffering from asthma, then administering to the subject an effective amount of a compound of Formula I to treat asthma.

A method for treating asthma is based on the properties of the Formula I compounds to reduce at least one of the following processes contributing to pathophysiologies that accompany this disorder: inflammation, excessive cell proliferation, remodeling, airway and/or lung tissue edema, airway hyperreactivity or bronchoconstriction.

Indicia of efficacy for treating asthma by the present method include demonstrable improvement in measurable signs, symptoms and other variables clinically relevant to asthma. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance and/or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

COPD

The inventors have discovered that Compounds of Formula I inhibit Rho kinase and are therefore useful in treating the defects in inflammation, pulmonary neutrophilia and eosinophilia, excessive cell proliferation, remodeling, airway and/or lung tissue edema, airway hyperreactivity or bronchoconstriction as well as preventing the development of airway hyperreactivity seen in COPD.

The present invention is directed to a method of treating COPD. The method comprises the steps of first identifying a subject suffering from COPD, then administering to the subject an effective amount of a compound of Formula I to treat COPD.

A method for treating COPD is based on the properties of the Formula I compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating COPD by the present method include demonstrable improvement in measurable signs, symptoms and other variables clinically relevant to COPD. Such improvements include decreased frequency of exacerbations, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

RSV Infection

The inventors have discovered that Compounds of Formula I inhibit Rho kinase and therefore inhibit the Rho kinase-mediated regulation of chemotaxis, cytokinesis, cytokine and chemokine secretion, endothelial cell integrity and smooth muscle contraction. Further, the inventors have discovered that Compounds of Formula I are useful in treating the inflammation, pulmonary neutrophilia, airway and/or lung tissue edema, remodeling, airway hyperreactivity or bronchoconstriction as well as preventing the development of airway hyperreactivity seen during RSV infection.

The present invention is directed to a method of treating respiratory illness caused by RSV infection. The method comprises the steps of first identifying a subject suffering from respiratory illness caused by RSV infection, then administering to the subject an effective amount of a compound of Formula I to treat said respiratory illness.

A method for treating respiratory problems stemming from RSV infection is based on the properties of the Formula I compounds to reduce at least one of the following processes contributing to pathophysiologies that accompany this disorder: inflammation, pulmonary neutrophilia, airway and/or lung tissue edema, remodeling, airway hyperreactivity or bronchoconstriction.

Indicia of efficacy for treating respiratory illness caused by RSV infection by the present method include demonstrable improvement in measurable signs, symptoms and other variables clinically relevant to RSV infection. Such improvements include decreased viral load in the lung tissue, sputum or bronchoalveolar lavage fluid, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

PAH

The inventors have discovered that Compounds of Formula I inhibit Rho kinase and are therefore useful in treating vascular growth, smooth muscle cell proliferation, remodeling, vasoreactivity, vasoconstriction or inflammation seen in PAH.

The present invention is directed to a method of treating PAH. The method comprises the steps of first identifying a subject suffering from PAH, and then administering to the subject an effective amount of a compound of Formula I to treat PAH.

A method of treating PAH is based on the properties of the Formula I compounds to reduce at least one of the following processes contributing to pathophysiologies that accompany this disorder: vascular growth, smooth muscle cell proliferation, remodeling, vasoreactivity, vasoconstriction or inflammation.

Indicia of efficacy for treating pulmonary arterial hypertension by the present method include demonstrable improvement in measurable signs, symptoms and other variables clinically relevant to PAH. Such improvements include reversing, stopping or slowing down of the pathological remodeling of the pulmonary vasculature, reversing, stopping or slowing down the hypertrophy of the right ventricle, decreasing the pulmonary arterial pressure, increasing cardiac output, improvement in cardiac patient class status, increased blood oxygen saturation, decreased hypoxia and hypercapnia, decreased need for supplemental oxygen, improved distance walked during the 6 minute walk test, decreased need for mechanical ventilation, lower amount of inflammatory cells infiltrating the lung, lower levels of proinflammatory cytokines and chemokines, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, patient-reported or physician-observed signs such as ease of breathing, or severity of coughing and/or wheezing.

LAM

The inventors have discovered that Compounds of Formula I inhibit Rho kinase and are therefore useful in treating excessive smooth muscle cell proliferation, smooth muscle cell migration, remodeling, lung tissue edema or bronchoconstriction seen in LAM.

The present invention is directed to a method of treating LAM. The method comprises the steps of first identifying a subject suffering from LAM, and then administering to the subject an effective amount of a compound of Formula I to treat LAM.

A method for treating LAM is based on the properties of the Formula I compounds to reduce at least one of the following processes contributing to pathophysiologies that accompany this disorder: excessive smooth muscle cell proliferation, smooth muscle cell migration, remodeling, lung tissue edema or bronchoconstriction.

Indicia of efficacy for treating LAM by the present method include demonstrable improvement in measurable signs, symptoms and other variables clinically relevant to LAM. Such improvements include decreased frequency of pneumothorax, decrease frequency of pulmonary bleeding, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, angiomyolipoma volume reduction or severity of coughing and/or wheezing.

IPF

The inventors have discovered that Compounds of Formula I are Rho kinase inhibitors and are therefore useful in treating inflammation, pulmonary neutrophilia, fibrosis, excessive cell proliferation, remodeling, lung tissue edema, airway hyperreactivity, bronchoconstriction or decline in lung function as well as preventing the development of airway hyperreactivity seen in IPF.

The present invention is directed to a method of treating IPF. The method comprises the steps of first identifying a subject suffering from IPF, and then administering to the subject an effective amount of a compound of Formula I to treat IPF.

A method for treating IPF is based on the properties of the Formula I compounds to reduce at least one of the following processes contributing to pathophysiologies that accompany this disorder: inflammation, pulmonary neutrophilia, fibrosis, excessive cell proliferation, remodeling, lung tissue edema, airway hyperreactivity or bronchoconstriction.

Indicia of efficacy for treating IPF by the present method include demonstrable improvement in measurable signs, symptoms and other variables clinically relevant to IPF. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method, amount of epithelial lining fluid, wet to dry lung weight, alveolar fluid clearance, radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

ARDS and VILI

The inventors have discovered that Compounds of Formula I inhibit Rho kinase and are therefore useful in inhibiting the Rho kinase-mediated regulation of chemotaxis, cytokinesis, cytokine and chemokine secretion, endothelial integrity and/or smooth muscle contraction. Furthermore, the inventors have discovered that Compounds of Formula I are useful in treating the defects in inflammation, remodeling, airway and/or lung tissue edema, airway hyperreactivity or bronchoconstriction as well as preventing the development of airway hyperreactivity seen in ARDS and/or VILI.

The present invention is directed to a method of treating ARDS and/or VILI. The method comprises the steps of first identifying a subject suffering from ARDS and/or VILI, then administering to the subject an effective amount of a compound of Formula I to treat ARDS and/or VILI.

A method for treating ARDS and/or VILI is based on the properties of the Formula I compounds to reduce at least one of the following processes contributing to pathophysiologies that accompany this disorder: inflammation, remodeling, airway and/or lung tissue edema, airway hyperreactivity or bronchoconstriction.

Indicia of efficacy for treating ARDS and/or VILI by the present method include demonstrable improvement in measurable signs, symptoms and other variables clinically relevant to ARDS and/or VILI. Such improvements include demonstrable improvement in measurable signs of edema and/or inflammation. Such signs of improvement include increased blood oxygen saturation or decreased frequency of coughing and/or wheezing, decreased hypoxia and hypercapnia, improved forced expiratory volume ($FEV_1$) forced vital capacity (FVC) or other physiologically relevant parameter of respiratory function, improved APACHE III score in the ICU, decreased need for mechanical ventilation, improved alveolar fluid clearance rate, decreased pulmonary edema as determined by any radiographic or other detection method such as the amount of epithelial lining fluid or radiographic visualization methods, bronchoscopy, brain natriuretic peptide levels, level of oxygenation/hypoxia, lower levels of inflammatory cells in the lung or outside of the lung in other anatomical compartments or spaces including systemic circulation, lower amounts of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing, and feelings of well-being.

CF

The inventors have discovered that Rho kinase inhibitors such as Compounds of Formula I the Rho kinase-mediated regulation of chemotaxis, cytokinesis, cytokine and chemokine secretion, proliferation, cell motility, endothelial integrity and/or smooth muscle contraction. Furthermore, the inventors have discovered that Rho kinase inhibitors such as Compounds of Formula I are useful in treating the defects in inflammation, pulmonary neutrophilia, excessive cell proliferation, remodeling, airway and/or lung tissue edema, airway hyperreactivity or bronchoconstriction or vasoconstriction as well as preventing the development of airway hyperreactivity seen in CF.

The present invention is directed to a method of treating CF. The method comprises the steps of first identifying a subject suffering from CF, then administering to the subject an effective amount of a Rho kinase inhibitor to treat CF.

A method for treating CF is based on the properties of Rho kinase inhibitors such as Formula I compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction or vasoconstriction.

Indicia of efficacy for treating CF by the present method include demonstrable improvement in measurable signs, symptoms and other variables clinically relevant to CF. Such improvements include decreases in the recurrence and progression of cough, chronic infection, pulmonary inflammation and airway damage, decreased chemotaxis and pulmonary infiltration of neutrophils and other inflammatory cells, decreased release of destructive enzymes and inflammatory cytokines from inflammatory cells, decreased rate of neutrophil apoptosis and increased removal of apoptotic cells, reduced amounts of DNA and cytosolic matrix proteins in the airway lumen, decreased viscosity of the airway mucus, decreased incidence and severity of bronchiectasis, irreversible lung damage, and respiratory failure, reduced incidence of spontaneous pneumothorax and hemoptysis, decreased parenchymal congestion, reduction in purulent secretions in dilated airways, reduction in cyst formation, decreased respiratory epithelial hyperplasia, erosion and squamous metaplasia, reduced mucoid plugging and inflammatory cells in the airway lumen, decreased submucosal gland hypertorphy and airway smooth muscle hyperplasia, decreased airway hyperreactivity, decreased lung hyperinflation, reduced need for surgical resection of damaged tissue, decreased ratio of residual volume to total lung capacity (RV/TLC) and increased $FEF_{25-75}$, increased forced expiratory volume in one second ($FEV_1$) and $FEV_1$/FVC, prevention of increases in TLC and RV, decreased incidence of acute pulmonary exacerbations, improved ventilation-perfusion, decreased hypoxemia, reduced requirement for oxygen supplementation, decreased hypercapnia, reduced vascular smooth muscle hypertrophy and pulmonary hypertension, decreased incidence of right ventricular hypertrophy, cor pulmonale and right heart failure, decreased need for lung transplant, and decreased mortality.

Bronchiectasis

The inventors have discovered that Compounds of Formula I inhibit Rho kinase and are therefore useful in inhibiting the Rho kinase-mediated regulation of chemotaxis, cytokinesis, cytokine and chemokine secretion, proliferation, cell motility, endothelial integrity and/or smooth muscle contraction, inflammation, pulmonary neutrophilia, excessive cell proliferation, remodeling, airway and/or lung tissue edema, airway hyperreactivity or bronchoconstriction and development of airway hyperreactivity seen in bronchiectasis.

The present invention is directed to a method of treating bronchiectasis. The method comprises the steps of first identifying a subject suffering from bronchiectasis, then administering to the subject an effective amount of a compound of Formula I to treat bronchiectasis.

A method for treating bronchiectasis is based on the properties of the Formula I compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating bronchiectasis by the present method include demonstrable improvement in measurable signs, symptoms and other variables clinically relevant to bronchiectasis. Such improvements include: increased blood oxygen saturation, decreased hypoxia and hypercapnia, decreased need for supplemental oxygen, decreased dyspnea, decreased frequency of coughing and/or wheezing, improved forced expiratory volume ($FEV_1$), forced vital capacity (FVC), reduced mean $H_2O_2$ concentration in exhaled breath condensate, improved chest radiograph or high-resolution CT scan or other physiologically relevant parameter of respiratory function, decreased ER and/or office visits, decreased hospitalizations, decrease in missed school or work days, decreased mortality or morbidity, decreased length of hospital stay, decreased need for mechanical ventilation, decreases bronchial wall thickening, decreased luminal dilation, lower amount of inflammatory cells infiltrating the lung, lower levels of pro-inflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, decreases in sputum expectoration, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing, increased distance walked during a walk test and endurance capacity, feelings of well-being or other measurable variables related to quality of life.

AATD

The inventors have discovered that Compounds of Formula I inhibit Rho kinase and therefore inhibit the Rho kinase-mediated regulation of chemotaxis, cytokinesis, cytokine and chemokine secretion, proliferation, cell motility, endothelial integrity, smooth muscle contraction, inflammation, pulmonary neutrophilia, excessive cell proliferation, remodeling, airway and/or lung tissue edema, airway hyperreactivity or bronchoconstriction and development of airway hyperreactivity seen in AATD.

The present invention is directed to a method of treating AATD. The method comprises the steps of first identifying a subject suffering from AATD, then administering to the subject an effective amount of a compound of Formula I to treat AATD.

A method for treating AATD is based on the properties of the Formula I compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating AATD by the present method include demonstrable improvement in measurable signs, symptoms and other variables clinically relevant to AATD. Such improvements include: improvement in $FEV_1$, forced vital capacity (FVC) or other physiologically relevant parameter of respiratory function, reduction of cough, phlegm production, and wheezing, either chronically or with upper respiratory tract infections, reduction of dyspnea, increase in bronchodilator responsiveness, function, decreased ER and/or office visits, decreased hospitalizations, decrease in missed school or work days, decreased mortality or morbidity, decreased length of hospital stay, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing.

Rhinitis

The inventors have discovered that Compounds of Formula I inhibit Rho kinase and therefore inhibit the Rho kinase-mediated regulation of chemotaxis, cytokinesis, cytokine and chemokine secretion, proliferation, cell motility, endothelial integrity, smooth muscle contraction, inflammation, excessive cell proliferation, remodeling, airway and/or lung tissue edema or airway hyperreactivity seen in rhinitis.

The present invention is directed to a method of treating rhinitis. The method comprises the steps of first identifying a subject suffering from rhinitis, then administering to the subject an effective amount of a compound of Formula I to treat rhinitis.

A method for treating rhinitis is based on the properties of the Formula I compounds to reduce at least one of the following processes contributing to pathophysiologies that accompany this disorder: inflammation, excessive cell proliferation, remodeling, airway and/or lung tissue edema or airway hyperreactivity.

Indicia of efficacy for treating rhinitis by the present method include demonstrable improvement in measurable signs, symptoms and other variables clinically relevant to rhinitis. Such improvements include measureable reduction in the inflammation of the nasal passages including eliminating irritants and mucus secretions from the nasal passages, blockage of the constricting agents released from the inflammatory cells, and eliminating exposure to environmental allergens. Clinical indices of efficacy include improvements (relative to placebo) and the relief of signs and symptoms of rhinitis, including four nasal symptoms (nasal stuffiness/blockage, runny nose, itchy nose and sneezing) and three ocular symptoms (itching/burning, tearing/watering, and redness). Derived total nasal and ocular symptoms scores (such as daily and instantaneous) can also serve as indicia of efficacy. Nasal and ocular symptoms scores acceptable for demonstrating clinical efficacy are defined as follows:

Total Nasal Symptom Score Modified (TNSSm) defined as TNSS with the nasal stuffiness/blockage removed from the scoring; sum of 3 nasal symptoms only, including runny nose, itchy nose, and sneezing, 0-9 possible score Total Nasal Symptom Score (TNSS); sum of 4 nasal symptoms including runny nose, nasal itching, sneezing, and nasal stuffiness/blockage, 0-12 possible score Total Ocular Symptom Score (TOSS); sum of 3 ocular symptoms including itching/burning eyes, tearing/watering eyes, and ocular redness, 0-9 possible score Rhinosinusitis The inventors have discovered that Compounds of Formula I inhibit Rho kinase and therefore inhibit the Rho kinase-mediated regulation of chemotaxis, cytokinesis, cytokine and chemokine secretion, proliferation, cell motility, endothelial integrity and/or smooth muscle contraction, inflammation, excessive cell proliferation, remodeling, edema or airway hyperreactivity seen in rhinosinusitis.

The present invention is directed to a method of treating rhinosinusitis. The method comprises the steps of first identifying a subject suffering from rhinosinusitis, then administering to the subject an effective amount of a compound of Formula I to treat rhinosinusitis.

A method for treating rhinosinusitis is based on the properties of the Formula I compounds to reduce at least one of the following processes contributing to pathophysiologies that accompany this disorder: inflammation, excessive cell proliferation, remodeling, edema or airway constriction.

Indicia of efficacy for treating rhinosinusitis by the present method include demonstrable improvement in measurable signs, symptoms and other variables clinically relevant to rhinosinusitis. Such improvements include clearing of the sinus cavity, decreased congestion, alleviation of pain, restoration of normal mucus viscosity, decrease in inflammation, decrease in edema, relaxation of smooth muscle, attenuated pro-inflammatory cells and molecules including cytokines, increased ease of breathing, decreased incidence of facial pain, pressure and fullness, alleviation of nasal obstruction and congestion, attenuation of post nasal drip, increased sense of smell, decreased incidences of headache, lessening of fatigue, improved readings from sinus computed tomographic (CT) imaging, improvement as measured by physical or radiological examination, reduced duration of signs and symptoms, reduced incidence of infection, reduced need for antibiotics, steroids or other related treatments, and reduced flora in specimens from endoscopy.

PCD, Pneumonia, and Bronchiolitis Caused by Agents Other than RSV

The inventors have discovered that Compounds of Formula I inhibit Rho kinase and therefore inhibit the Rho kinase-mediated regulation of chemotaxis, cytokinesis, cytokine and chemokine secretion, cell motility, endothelial integrity, smooth muscle contraction, inflammation, lung tissue edema, airway hyperreactivity or bronchoconstriction and development of airway hyperreactivity seen in PCD, pneumonia, and bronchiolitis caused by agents other than RSV.

The present invention is directed to a method of treating PCD, pneumonia, and bronchiolitis caused by agents other than RSV. The method comprises the steps of first identifying a subject suffering from PCD, pneumonia or bronchiolitis caused by agents other than RSV, then administering to the subject an effective amount of a compound of Formula I to treat PCD, pneumonia or bronchiolitis caused by agents other than RSV.

A method for treating PCD, pneumonia or bronchiolitis caused by agents other than RSV is based on the properties of the Formula I compounds to reduce at least one of the following processes contributing to pathophysiologies that accompany this disorder: inflammation, lung tissue edema, airway hyperreactivity or bronchoconstriction.

Indicia of efficacy for treating PCD, pneumonia, and bronchiolitis caused by agents other than RSV by the present method include demonstrable improvement in measurable signs, symptoms and other variables clinically relevant to PCD, pneumonia, and bronchiolitis caused by agents other than RSV. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

OB/BOOP Due to Lung Transplantation or HSCT

The inventors have discovered that Compounds of Formula I inhibit Rho kinase and are therefore useful in treating inflammation, fibrosis, excessive cell proliferation, remodeling, airway hyperreactivity, bronchoconstriction or decline in lung function as well as preventing the development of airway hyperreactivity seen in OB/BOOP due to lung transplantation or HSCT.

The present invention is directed to a method of treating OB/BOOP due to lung transplantation or HSCT. The method comprises the steps of first identifying a subject suffering from OB/BOOP due to lung transplantation or HSCT, and then administering to the subject an effective amount of a compound of Formula I to treat OB/BOOP due to lung transplantation or HSCT.

A method for treating OB/BOOP due to lung transplantation or HSCT is based on the properties of the Formula I compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating OB/BOOP due to lung transplantation or HSCT by the present method include demonstrable improvement in measurable signs, symptoms and other variables clinically relevant to OB/BOOP due to lung transplantation or HSCT. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstial infiltrates as determined by any radiographic or other detection method, improvement in histopathological changes of the pulmonary parenchyma, increase in general quality of life, improvement in gas exchange abnormalities including carbon monoxide diffusing capacity (DLCO).

Non-IPF IIP

The inventors have discovered that Compounds of Formula I inhibit Rho kinase and are therefore useful in treating inflammation, fibrosis, excessive cell proliferation, remodeling, airway hyperreactivity, bronchoconstriction or decline in lung function as well as preventing the development of airway hyperreactivity seen in non-IPF IIP.

The present invention is directed to a method of treating non-IPF IIP. The method comprises the steps of first identifying a subject suffering from non-IPF IIP, and then administering to the subject an effective amount of a compound of Formula I to treat non-IPF IIP.

A method for treating non-IPF IIP is based on the properties of the Formula I compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating non-IPF IIP by the present method include demonstrable improvement in measurable signs, symptoms and other variables clinically relevant non-IPF IIP. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstial infiltrates as determined by any radiographic or other detection method, improvement in histopathological changes of the pulmonary parenchyma, increase in general quality of life, improvement in gas exchange abnormalities including carbon monoxide diffusing capacity (DLCO).

ILD Other than IPF, Non-IPF IIPs and OB/BOOP

The inventors have discovered that Compounds of Formula I inhibit Rho kinase and are therefore useful in treating inflammation, fibrosis, excessive cell proliferation, remodeling, airway hyperreactivity, bronchoconstriction or decline in lung function as well as preventing the development of airway hyperreactivity seen in ILD other than IPF, non-IPF IIPs and OB/BOOP.

The present invention is directed to a method of treating ILD other than IPF, non-IPF IIPs and OB/BOOP. The method comprises the steps of first identifying a subject suffering from ILD other than IPF, non-IPF IIPs and OB/BOOP, and then administering to the subject an effective amount of a compound of Formula I to treat ILD other than IPF, non-IPF Ill's and OB/BOOP.

A method for treating ILD other than IPF, non-IPF IIPs and OB/BOOP is based on the properties of the Formula I compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating ILD other than IPF, non-IPF IIPs and OB/BOOP by the present method include demonstrable improvement in measurable signs, symptoms and other variables clinically relevant to ILD other than IPF, non-IPF IIPs and OB/BOOP. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstial infiltrates as determined by any radiographic or other detection method, improvement in histopathological changes of the pulmonary parenchyma, increase in general quality of life, improvement in gas exchange abnormalities including carbon monoxide diffusing capacity (DLCO), improvements in arthralgia, myalgia, hemoptysis, rash or pneumothorax.

An effective amount of a Formula I compound is administered to a patient in need of treatment for asthma, COPD, respiratory tract illness caused by respiratory syncytial virus infection such as RSV-induced wheezing and hyperreactivity or bronchiolitis, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF HP and ILD other than IPF, non-IPF IIPs and OB/BOOP. The patient either already has the symptoms of at least one above-mentioned disease, or is identified as being at risk of at least one above-mentioned disease. The compound is administered at a frequency that achieves desired efficacy. What constitutes desired efficacy is determined by a physician or other health-care professional. Whether or not sufficient efficacy has been reached is determined by indicia of efficacy for the specific disease. After an initial dose, additional doses are optionally administered if judged to be necessary by a health-care professional.

Methods of Administration

The present invention provides a method of reducing intraocular pressure, including treating glaucoma such as primary open-angle glaucoma; a method of treating constriction of the visual field; a method of inhibiting wound healing after trabeculectomy; a method of treating posterior capsule opacification following extracapsular cataract extraction and intraocular lens implantation; a method of inhibiting angiogenesis; a method of modulating fluid transport on the ocular surface; a method of controlling vasospasm; a method of increasing tissue perfusion; a method of neuroprotection; and a method of vasoprotection to atherogenic agents, and a method of treating allergic conjunctivitis, corneal hyposensitivity and kerotopathy, dry eye disease, proliferative vitreal retinopathy, macular edema and degeneration, and blepharitis. Any method of delivering the compound to the relevant tissues of the eye, including local administration and systemic administration, is suitable for the present invention.

The present invention is particularly effective in treating pulmonary disease such as asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, and bronchiolitis caused by agents other than RSV, OB/BOOP due to lung transplantation or HSCT, non-IPF IIP and ILD other than IPF, non-IPF IIPs and OB/BOOP. Any method of delivering the compound to the relevant tissues of the lung, including local administration and systemic administration, is suitable for the present invention.

In one embodiment, the active compound is delivered by systemic administration; the compound first reaches plasma and then distributes into the lung or ocular tissues. Examples of systemic administration include oral ingestion, intravenous, subcutaneous, intraperitoneal, intrathecal or intramuscular administration.

Additional method of systemic administration of the active compound involves administering a suppository form of the active compound, such that a therapeutically effective amount of the compound reaches the target sites via systemic absorption and circulation.

Another method of systemically administering the active compounds involves administering a liquid/liquid suspension in the form of nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

The active compounds can also be systemically administered through absorption by the skin using transdermal patches or pads. The active compounds are absorbed into the bloodstream through the skin. Plasma concentration of the active compounds can be controlled by using patches containing different concentrations of active compounds.

For systemic administration, plasma concentrations of active compounds delivered can vary according to compounds; but are generally $1\times10^{-10}$-$1\times10^{-4}$ moles/liter, and preferably $1\times10^{-8}$-$1\times10^{-5}$ moles/liter. Dosage levels about 0.01-140 mg per kg of body weight per day are useful in the treatment or preventions of pulmonary diseases (about 0.5 mg to about 7 g per patient per day). Preferred dosage levels are about 0.05-100, 0.1-100, or 1-100 mg/kg body weight per day. The amount of active ingredient that can be combined with the carrier materials to produce a single dosage form will vary depending upon the host treated and the particular mode of administration. Dosage unit forms will generally contain between from about 1 mg to about 500 mg of an active ingredient. Injection dose levels range from about 0.1 mg/kg/hour to at least 10 mg/kg/hour, all from about 1 to about 120 hours and especially 24 to 96 hours. A preloading bolus from about 0.1 mg/kg to about 10 mg/kg or more can be administered to achieve adequate steady state levels. The maximum total dose in general does not exceed about 2 g/day for a 40 to 80 kg human patient.

Frequency of dosage can also vary depending on the compound used and the particular disease treated. However, for treatment of most disorders, a dosage regimen of p.r.n, 4 times daily, three times daily, or less is preferred, with a dosage regimen of once daily or 2 times daily being particularly preferred.

It is understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In a preferred embodiment, the pharmaceutical composition of the present invention is administered locally to the eye (e.g., topical, intracameral, intravitreal, subretinal, subconjunctival, retrobulbar or via an implant) in the form of ophthalmic formulations. The compounds of the invention can be combined with ophthalmologically acceptable preservatives, surfactants, viscosity enhancers, penetration enhancers, bioadhesives, antioxidants, buffers, sodium chloride, and water to form an aqueous or non-aqueous, sterile ophthalmic suspension, emulsion, microemulsion, gel, or solution to form the compositions of the invention.

The active compounds disclosed herein can be administered to the eyes of a patient by any suitable means, but are preferably administered by administering a liquid or gel suspension of the active compound in the form of drops, spray or gel. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lacrimal tissues or onto the eye surface.

In addition to the topical administration of the compounds to the eye, the compounds of the invention can be administered systematically by any methods known to a skilled person when used for the purposes described above.

In a preferred embodiment, the active compound is delivered by local administration to the lung. Local administration includes inhalation, topical application or targeted drug delivery. Methods of inhalation include liquid instillation, instillation as a pressurized fluid preparation via metered dose inhaler or equivalent, or inhalation of an aerosolized solution via nebulizer (preferred), inhalation of dry powder (more preferred), and directing soluble or dried material into the air stream during mechanical ventilation (also more preferred).

One local administration method is administering to a subject an aerosol suspension of respirable particles comprising the active compound by inhalation. The respirable particles can be liquid or solid, with a particle size sufficiently small to pass through the mouth and larynx upon inhalation; in general, particles ranging from about 1 to 10 microns, but more preferably 1-5 microns, in size are considered respirable. The surface concentrations of active compounds delivered via inhalation can vary according to compounds; but are generally $1\times10^{-10}$-$1\times10^{-4}$ moles/liter, and preferably $1\times10^{-8}$-$1\times10^{-5}$ moles/liter.

An example of targeted drug delivery is enclosure of the compound within a liposome, where the liposome is coated with a specific antibody whose antigen is expressed in the targeted lung tissue. It can be advantageous to construe a controlled delivery system of the compounds since such an inhaled product targets the site of action, presents the compound of interest in small regimented quantities and reduces/minimizes any unwanted side effects.

Another example of a delivery system includes microparticulate compositions of the compound. In such a case, the compound is formulated as a microparticulate wherein the carrier is loaded with the compound; such a preparation is then filtered through a fine porous membrane or suitable filtering medium or is exposed to solvent interchanges to produce nanoparticles. Such preparations can be freeze dried or held in suspension in an aqueous or physiologically compatible medium. The preparation so obtained can be inhaled by suitable means.

Another example of a suitable preparation includes a reconstitutable preparation. In this case, the compound is formulated in a preparation to contain the necessary adjuvant to make it physiologically compatible. Such a preparation can be reconstituted by addition of water for injection or suitable physiological fluids, admixed by simple agitation and inhaled using appropriate techniques described above.

The compounds described above can also be prepared into dry powder or equivalent inhalation powders using the well known art of super critical fluid technology. In such a case, the compound is admixed with appropriate excipients and milled into a homogenous mass using suitable solvents or adjuvants. Following this, this mass is subjected to mixing using super critical fluid technology and suitable particle size distribution achieved. The particles in the formulation need to be of a desired particle size range such that the particles can be directly inhaled into the lungs using a suitable inhalation technique or introduced into the lungs via a mechanical ventilator. Alternatively, a formulation can be designed such that the particles are large enough in size thereby offering sufficient surface area to dissolve completely in a suitable fluid when admixed together or to dissolve sufficiently enough prior to nebulization into the lungs.

To prevent particle size growth and minimize crystal growth of the compound, one embodiment is to include the use of spray-dried particles that have better aerodynamic properties than micronized material. This can be further extended to coat the surface of the hydrophilic molecule with one or more layers of hydrophobic material.

Preferred compounds of the invention will have favorable pharmacological properties. Such properties include, but are not limited to bioavailability, low toxicity, low serum protein binding and desirable in vitro and in vivo half-life.

Assays can be used to predict these desirable pharmacological properties. Assays used to predict bioavailability include transport across human intestinal cell monolayers, including Caco-2 cell monolayers. Toxicity to cultured hepatocyctes can be used to predict compound toxicity.

The invention is illustrated further by the following examples that are not to be construed as limiting the invention in scope to the specific procedures described in them.

EXAMPLES

Example 1

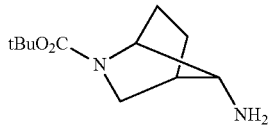 [SMILES: CC(C)(C)OC(=O)N1CC2CCC1C2N]

(1SR,4SR,7RS)-tert-butyl
7-amino-2-azabicyclo[2.2.1]heptane-2-carboxylate,
Intermediate 1

2-benzyl-2-azabicyclo[2.2.1]heptan-7-one is prepared as described in J. R. Malpass, S. Handa, and R. White, *Org. Lett.*, 2005, 7, 2759-2762. A solution of 2-benzyl-2-azabicyclo[2.2.1]heptan-7-one and benzylamine (1 mole equivalent) in 1,2-dichloroethane is purged with nitrogen and stirred at 20° C. for one hour. Sodium triacetoxyborohydride (1.3 mole equivalents) is added, and the reaction is monitored by analytical HPLC to completion. The reaction is diluted with saturated sodium bicarbonate. The organic phase is isolated, dried over MgSO$_4$, filtered and evaporated to dryness to afford the benzylamine adduct.

The benzylamine adduct is dissolved in ethanol, 2 equivalents of 4M HCl is added, and 10% Pd on carbon is added as a slurry in a small amount of water. The atmosphere of the vessel is exchanged for hydrogen, and the mixture is stirred under 1 atm of hydrogen and is monitored by analytical HPLC to completion. The mixture is then filtered to remove the catalyst and evaporated to a residue to afford the debenzylated diamine.

The debenzylated product is dissolved in methanol, 2 equivalents of 2M NaOH is added, and the mixture is treated with di-tert-butyl dicarbonate (1 mole equivalent). The reaction is monitored by analytical HPLC to completion. When complete, the mixture is evaporated and the residue is purified by reversed phase chromatography to afford the title compound.

Example 2

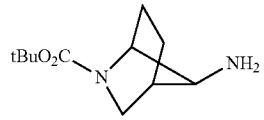 [SMILES: CC(C)(C)OC(=O)N1CC2CCC1C2N]

(1SR,4SR,7SR)-tert-butyl
7-amino-2-azabicyclo[2.2.1]heptane-2-carboxylate,
Intermediate 2

(1SR,4SR,7SR)-2-benzyl-2-azabicyclo[2.2.1]heptan-7-amine is prepared as described in WO07110782. (1SR,4SR,7SR)-2-benzyl-2-azabicyclo[2.2.1]heptan-7-amine is dissolved in ethanol, 2 equivalents of 4M HCl is added, and 10% Pd on carbon is added as a slurry in a small amount of water. The atmosphere of the vessel is exchanged for hydrogen, and the mixture is stirred under 1 atm of hydrogen and is monitored by analytical HPLC to completion. The mixture is then filtered to remove the catalyst and evaporated to a residue to afford the debenzylated diamine.

The debenzylated product is dissolved in methanol, 2 equivalents of 2M NaOH is added, and the mixture is treated with di-tert-butyl dicarbonate (1 mole equivalent). The reaction is monitored by analytical HPLC to completion. When complete, the mixture is evaporated and the residue is purified by reversed phase chromatography to afford the title compound.

Example 3

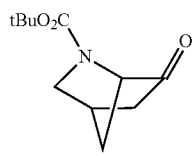 [SMILES: CC(C)(C)OC(=O)N1CC2CC(=O)C1C2]

tert-butyl
6-oxo-2-azabicyclo[2.2.1]heptane-2-carboxylate,
Intermediate 3

In a method analogous to J. Malpass and C. Cox, *Tetrahedron Lett.*, 1999, 40, 1419-1422, tert-butyl 2-azabicyclo[2.2.1]hept-5-ene-2-carboxylate is treated with diborane to afford a mixture of alcohols which is separated by chromatography. The desired alcohol tert-butyl 6-hydroxy-2-azabicyclo[2.2.1]heptane-2-carboxylate is then oxidized using the Swern procedure to afford the title compound.

Example 4

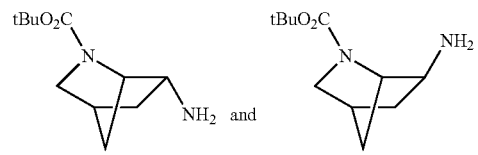 [SMILES: CC(C)(C)OC(=O)N1CC2CC(N)C1C2 ; "and" ; CC(C)(C)OC(=O)N1CC2CC(N)C1C2]

(1SR,4SR,6SR)-tert-butyl 6-amino-2-azabicyclo
[2.2.1]heptane-2-carboxylate, Intermediate 4, and
(1SR,4SR,6RS)-tert-butyl 6-amino-2-azabicyclo
[2.2.1]heptane-2-carboxylate, Intermediate 5

Using a procedure analogous to that shown in Example 1, Intermediate 3 is treated with benzylamine under reductive amination conditions to yield a mixture of diastereomeric benzylamine adducts, which is separated by chromatography. The two diastereomeric products are treated individually under hydrogenation conditions, also as described in Example 1, to yield the title compounds.

Example 5

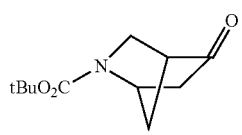 [SMILES: CC(C)(C)OC(=O)N1CC2CC1CC2=O]

tert-butyl
5-oxo-2-azabicyclo[2.2.1]heptane-2-carboxylate,
Intermediate 6

In a method analogous to J. Malpass and C. Cox, *Tetrahedron Lett.*, 1999, 40, 1419-1422, tert-butyl 2-azabicyclo[2.2.1]hept-5-ene-2-carboxylate is treated with diborane to afford a mixture of alcohols which is separated by chromatography. The desired alcohol tert-butyl 5-hydroxy-2-azabicyclo[2.2.1]heptane-2-carboxylate is then oxidized using the Swern procedure to afford the title compound.

Example 6

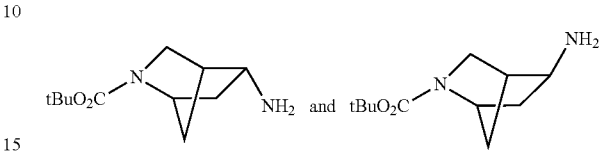

(1RS,4RS,5SR)-tert-butyl 5-amino-2-azabicyclo
[2.2.1]heptane-2-carboxylate, Intermediate 7, and
(1RS,4RS,5RS)-tert-butyl 5-amino-2-azabicyclo
[2.2.1]heptane-2-carboxylate, Intermediate 8

Using a procedure analogous to that shown in Example 1, Intermediate 6 is treated with benzylamine under reductive amination conditions to yield a mixture of diastereomeric benzylamine adducts, which is separated by chromatography. The two diastereomeric products are treated individually under hydrogenation conditions, also as described in Example 1, to yield the title compounds.

Example 7

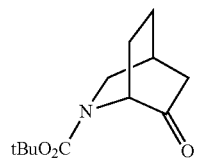

tert-butyl
6-oxo-2-azabicyclo[2.2.2]octane-2-carboxylate,
Intermediate 9

2-benzyl-2-azabicyclo[2.2.2]octan-6-ol is prepared using a method analogous to that described in U.S. Pat. No. 5,147,873. 2-benzyl-2-azabicyclo[2.2.2]octan-6-ol is debenzylated and subsequently protected as the tert-butyl carbamate using procedures analogous to those described in Example 1. Oxidation of the resulting intermediate alcohol using the Swern protocol affords the title product.

Example 8

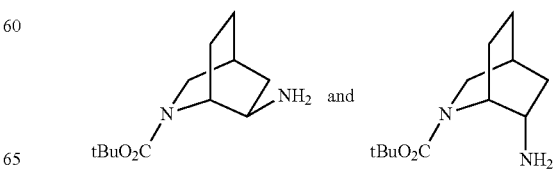

(1RS,4SR,6RS)-tert-butyl 6-amino-2-azabicyclo
[2.2.2]octane-2-carboxylate, Intermediate 10, and
(1RS,4SR,6SR)-tert-butyl 6-amino-2-azabicyclo
[2.2.2]octane-2-carboxylate, Intermediate 11

Using a procedure analogous to that shown in Example 1, Intermediate 9 is treated with benzylamine under reductive amination conditions to yield a mixture of diastereomeric benzylamine adducts, which is separated by chromatography. The two diastereomeric products are treated individually under hydrogenation conditions, also as described in Example 1, to yield the title compounds.

Example 9

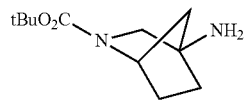 [SMILES: CC(C)(C)OC(=O)N1CC2(N)CCC1C2]

tert-butyl
4-amino-2-azabicyclo[2.2.1]heptane-2-carboxylate,
Intermediate 12

This material is prepared using a modification of the methods described in J. W. Huffman, T. Kamiya, and C. B. S. Rao, J. Org. Chem. 1967, 32, 700-703. A solution of ethyl 1-(((benzyloxy)carbonyl)amino)cyclopent-3-enecarboxylate (Aldrich) in methylene chloride is treated at 0° C. with MCPBA (1.1 equivalents), and the reaction is monitored by analytical HPLC to completion. The reaction is diluted with saturated sodium bicarbonate. The organic phase is isolated, dried over $MgSO_4$, filtered and evaporated to dryness to afford the epoxide product ethyl 3-(((benzyloxy)carbonyl)amino)-6-oxabicyclo[3.1.0]hexane-3-carboxylate, which is purified by chromatography.

The epoxide is treated with an excess of benzylamine in ethanol, and the reaction is heated at reflux and monitored by analytical HPLC to completion. The reaction mixture is treated as described by Huffman et al. to afford the product benzyl (2-benzyl-6-hydroxy-3-oxo-2-azabicyclo[2.2.1]heptan-4-yl)carbamate, which is purified by chromatography.

The above alcohol is treated with tosyl chloride in pyridine as described by Huffman et al. to afford after workup the product 2-benzyl-4-(((benzyloxy)carbonyl)amino)-3-oxo-2-azabicyclo[2.2.1]heptan-6-yl 4-methylbenzenesulfonate, which is purified by chromatography.

The resulting tosylated product dissolved in ethanol and 10% Pd on carbon is added as a slurry in a small amount of water. The atmosphere of the vessel is exchanged for hydrogen, and the mixture is stirred under 1 atm of hydrogen and is monitored by analytical HPLC to completion. The mixture is then filtered to remove the catalyst and evaporated to a residue to afford the compound in which the CBZ protecting group has been removed, 4-amino-2-benzyl-3-oxo-2-azabicyclo[2.2.1]heptan-6-yl-4-methylbenzenesulfonate.

Lithium aluminum hydride (3 equivalents) is dissolved in THF under an atmosphere of nitrogen, and a THF solution of the above deprotected tosylate is added to the solution with stirring. The resulting mixture is heated to reflux and the reaction is monitored by analytical HPLC to completion. The mixture is then treated successively with water, 15% aqueous NaOH, and an additional portion of water, and the mixture is stirred to provide a precipitate. The precipitate is removed by filtration, and the filtrate is evaporated to provide a residue. Purification of the residue by chromatography affords 2-benzyl-2-azabicyclo[2.2.1]heptan-4-amine.

The above benzylamine is treated under debenzylation conditions as described in Example 1 to afford 2-azabicyclo[2.2.1]heptan-4-amine. Treatment of this debenzylated material with di-tert-butyl dicarbonate, again as described in Example 1, affords the title compound after purification by chromatography.

Example 10

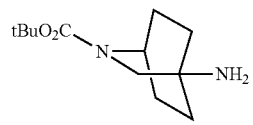 [SMILES: CC(C)(C)OC(=O)N1CC2(N)CCC1CC2]

tert-butyl
4-amino-2-azabicyclo[2.2.2]octane-2-carboxylate,
Intermediate 13

Ethyl 1-(((benzyloxy)carbonyl)amino)cyclohex-3-enecarboxylate is converted to the title compound using a procedure analogous to that described in Example 9.

Example 11

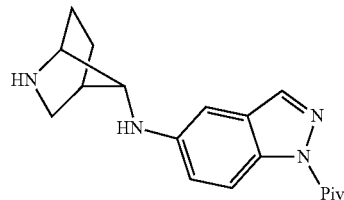

1-(5-(((1SR,4SR,7RS)-2-azabicyclo[2.2.1]heptan-7-ylamino)-1H-indazol-1-yl)-2,2-dimethylpropan-1-one, Intermediate 14

To a solution of 1-(5-amino-1H-indazol-1-yl)-2,2-dimethylpropan-1-one maleate salt (580 mg, 1.7 mmol, prepared as described in U.S. Ser. No. 08/021,4614) and 2-benzyl-2-azabicyclo[2.2.1]heptan-7-one (250 mg, 1.7 mmol) (J. R. Malpass, S. Handa, and R. White, Org. Lett., 2005, 7, 2759-2762) in THF (9 mL) was added sodium triacetoxyborohydride (740 mg, 3.5 mmol), and the mixture was stirred at ambient temperature for 24 h. The reaction mixture was partitioned between aqueous sodium bicarbonate and ethyl acetate, and the organic layer was washed with brine and dried over sodium sulfate. The solvent was evaporated and the residue was purified by normal phase chromatography followed by reversed phase HPLC to afford 175 mg (25%) of 1-(5-(((1SR,4SR,7RS)-2-benzyl-2-azabicyclo[2.2.1]heptan-7-ylamino)-1H-indazol-1-yl)-2,2-dimethylpropan-1-one.

The above intermediate benzyl compound is dissolved in ethyl acetate/ethanol, the atmosphere is purged with nitrogen, and 10% Pd on carbon is added, followed by excess ammonium formate dissolved in a minimum volume of formic acid. The reaction is stirred at ambient temperature, monitoring for completion by TLC. When complete, the reaction mixture is filtered, partitioned between ethyl acetate and brine, and the organic phase is dried over magnesium sulfate and concentrated to yield the title compound.

Examples 12-15

Reaction of 1-(5-amino-1H-indazol-1-yl)-2,2-dimethylpropan-1-one maleate salt with the indicated intermediate ketones using the method of Example 11 affords the Intermediates 15-21, shown in Examples 12-15:

Example 12

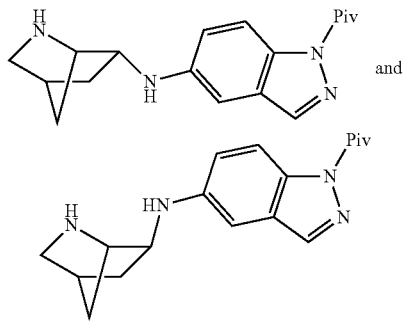

1-(5-(((1SR,4SR,6SR)-2-azabicyclo[2.2.1]heptan-6-ylamino)-1H-indazol-1-yl)-2,2-dimethylpropan-1-one, Intermediate 15, and 1-(5-(((1SR,4SR,6RS)-2-azabicyclo[2.2.1]heptan-6-ylamino)-1H-indazol-1-yl)-2,2-dimethylpropan-1-one, Intermediate 16

Reaction of 1-(5-amino-1H-indazol-1-yl)-2,2-dimethylpropan-1-one maleate salt with benzyl 6-oxo-2-azabicyclo[2.2.1]heptane-2-carboxylate (J. Malpass and C. Cox, *Tetrahedron Lett.*, 1999, 40, 1419-1422) affords a mixture of the two diastereomeric title compounds as the CBZ-protected amines. Separation of the diastereomers by chromatography followed by removal of the CBZ group from the individual isomers by hydrogenolysis affords the title amines.

Example 13

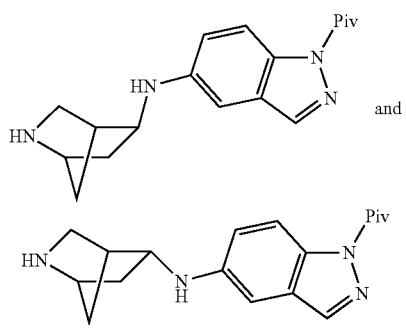

1-(5-(((1SR,4SR,6SR)-2-azabicyclo[2.2.1]heptan-6-ylamino)-1H-indazol-1-yl)-2,2-dimethylpropan-1-one, Intermediate 17, and 1-(5-(((1SR,4SR,6RS)-2-azabicyclo[2.2.1]heptan-6-ylamino)-1H-indazol-1-yl)-2,2-dimethylpropan-1-one, Intermediate 18

Reaction of 1-(5-amino-1H-indazol-1-yl)-2,2-dimethylpropan-1-one maleate salt with benzyl 5-oxo-2-azabicyclo[2.2.1]heptane-2-carboxylate (J. Malpass and C. Cox, *Tetrahedron Lett.*, 1999, 40, 1419-1422) affords a mixture of the two diastereomeric title compounds as the CBZ-protected amines. Separation of the diastereomers by chromatography followed by removal of the CBZ group from the individual isomers by hydrogenolysis affords the title amines.

Example 14

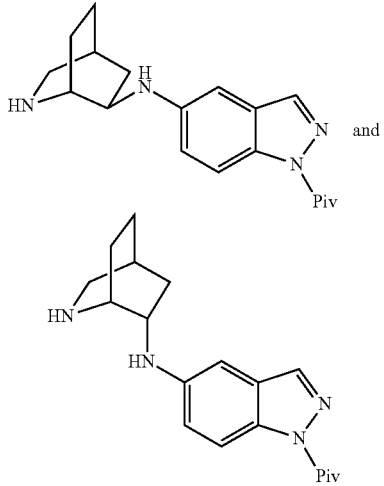

1-(5-(((1SR,4SR,6SR)-2-azabicyclo[2.2.1]heptan-6-ylamino)-1H-indazol-1-yl)-2,2-dimethylpropan-1-one, Intermediate 19, and 1-(5-(((1SR,4SR,6RS)-2-azabicyclo[2.2.1]heptan-6-ylamino)-1H-indazol-1-yl)-2,2-dimethylpropan-1-one, Intermediate 20

Reaction of 1-(5-amino-1H-indazol-1-yl)-2,2-dimethylpropan-1-one maleate salt with benzyl 6-oxo-2-azabicyclo[2.2.2]octane-2-carboxylate (U.S. Pat. No. 5,147,873) affords a mixture of the two diastereomeric title compounds as the CBZ-protected amines. Separation of the diastereomers by chromatography followed by removal of the CBZ group from the individual isomers by hydrogenolysis affords the title amines.

Example 15

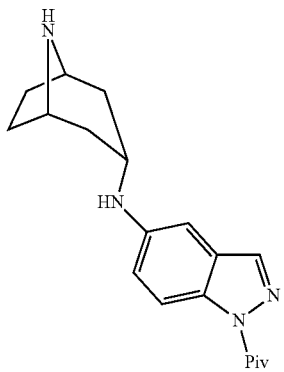

1-(5-((1RS,3rs,5SR)-8-azabicyclo[3.2.1]octan-3-ylamino)-1H-indazol-1-yl)-2,2-dimethylpropan-1-one, Intermediate 21

To a solution of 8-benzyl-8-azabicyclo[3.2.1]octan-3-one (500 mg, 2.32 mmol) and 1-(5-amino-1H-indazol-1-yl)-2,2-dimethylpropan-1-one maleate salt (735 mg, 2.21 mmol) in THF (5 mL) was added trifluoroacetic acid (0.60 mL, 7.7 mmol), and the mixture was stirred for 30 min. Sodium triacetoxyborohydride was added (935 mg, 4.41 mmol), and the mixture was allowed to stir for 24 h. The reaction mixture was partitioned between 1M NaOH and ethyl acetate, and the organic phase was dried over sodium sulfate and filtered through a silica plug. Evaporation of the solvent gave a residue which was purified by trituration with methanol to afford 1-(5-((1RS,3rs,5SR)-8-benzyl-8-azabicyclo[3.2.1]octan-3-ylamino)-1H-indazol-1-yl)-2,2-dimethylpropan-1-one (465 mg, 51%).

The above intermediate benzyl compound is dissolved in ethyl acetate/ethanol, the atmosphere is purged with nitrogen, and 10% Pd on carbon (100 mg) is added, followed by ammonium formate (700 mg) dissolved in a minimum volume of formic acid. The reaction is stirred at ambient temperature, monitoring for completion by TLC. After 3 h, the reaction mixture is filtered, partitioned between ethyl acetate and 1M NaOH, and the organic phase is dried over magnesium sulfate and concentrated to yield the title compound (320 mg, 86%, 44% overall).

Example 16

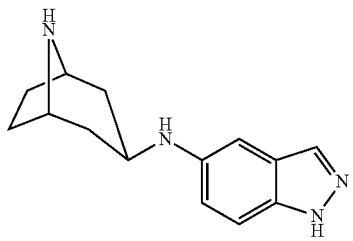 [SMILES: c1cc2[nH]ncc2cc1NC1CC2CCC(C1)N2]

N-((1RS,3sr,5SR)-8-azabicyclo[3.2.1]octan-3-yl)-1H-indazol-5-amine, Intermediate 22

A mixture of 5-bromo-1-(tetrahydro-2H-pyran-2-yl)-1H-indazole (Slade et al., J. Org. Chem., 74: 6331-6334, 2009, 621 mg, 2.21 mmol), (1RS,3sr,5SR)-tert-butyl 3-amino-8-azabicyclo[3.2.1]octane-8-carboxylate (500 mg, 2.21 mmol), tris(dibenzylideneacetone)dipalladium(0) (101 mg, 0.11 mmol), R-(+)-2,2'-bis(diphenylphosphino)-1,1'-binaphthyl (165 mg, 0.265 mmol), and sodium tert-butoxide (743 mg, 7.73 mmol) in a round-bottomed flask was purged with nitrogen three times, THF (5 mL) was added, and the mixture was stirred at 60° C. for 72 h, at which time the starting materials had been consumed as judged by analytical HPLC. The mixture was concentrated and the residue was chromatographed on silica gel to afford (1RS,3sr,5SR)-tert-butyl 3-((1-pivaloyl-1H-indazol-5-yl)amino)-8-azabicyclo[3.2.1]octane-8-carboxylate (440 mg, 44%).

The above fully protected material was dissolved in 8 mL of 0.63N HCl in isopropanol and the mixture was heated at 80° C. for 18 h. The mixture was concentrated, partitioned between 3M NaOH and ethyl acetate, and the organic phase was concentrated. Chromatography of the residue on silica gel afforded the title compound (170 mg, 68%, 30% overall).

Examples 17-20

Reaction of 5-bromo-1-(tetrahydro-2H-pyran-2-yl)-1H-indazole with the indicated intermediate amines using the method of Example 16 affords the Intermediates 23-26, shown in Examples 17-20:

Example 17

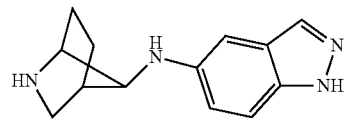

N-((1SR,4SR,7SR)-2-azabicyclo[2.2.1]heptan-7-yl)-1H-indazol-5-amine, Intermediate 23

Reaction of 5-bromo-1-(tetrahydro-2H-pyran-2-yl)-1H-indazole with Intermediate 2 affords the BOC- and THP-protected intermediate, which is purified by chromatography. Subsequent treatment with acid removes the protecting groups and affords the title amine.

Example 18

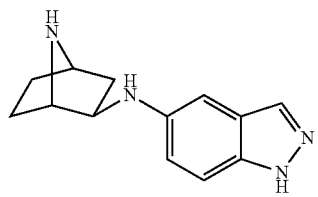 [SMILES: c1cc2[nH]ncc2cc1NC1CC2CCC1N2]

N-((1SR,2RS,4RS)-7-azabicyclo[2.2.1]heptan-2-yl)-1H-indazol-5-amine, Intermediate 24

Reaction of 5-bromo-1-(tetrahydro-2H-pyran-2-yl)-1H-indazole with (1SR,2RS,4RS)-tert-butyl 2-amino-7-azabicyclo[2.2.1]heptane-7-carboxylate (WO04073292) affords the BOC- and THP-protected intermediate, which is purified by chromatography. Subsequent treatment with acid removes the protecting groups and affords the title amine.

Example 19

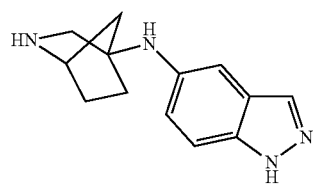 [SMILES: c1cc2[nH]ncc2cc1NC12CCC(C1)NC2]

N-(2-azabicyclo[2.2.1]heptan-4-yl)-1H-indazol-5-amine, Intermediate 25

Reaction of 5-bromo-1-(tetrahydro-2H-pyran-2-yl)-1H-indazole with Intermediate 12 affords the BOC- and THP-protected intermediate, which is purified by chromatography. Subsequent treatment with acid removes the protecting groups and affords the title amine.

Example 20

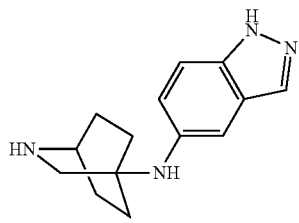 [SMILES: c1cc2[nH]ncc2cc1NC12CCC(CC1)NC2]

N-(1H-indazol-5-yl)-2-azabicyclo[2.2.2]octan-4-amine, Intermediate 26

Reaction of 5-bromo-1-(tetrahydro-2H-pyran-2-yl)-1H-indazole with Intermediate 13 affords the BOC- and THP-protected intermediate, which is purified by chromatography. Subsequent treatment with acid removes the protecting groups and affords the title amine.

Example 21

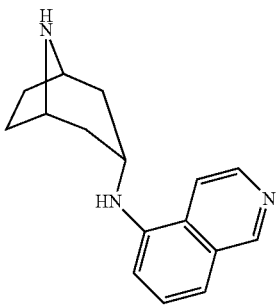 [SMILES: c1cc(NC2CC3CCC(C2)N3)c2ccncc2c1]

N-((1RS,3rs,5SR)-8-azabicyclo[3.2.1]octan-3-yl)isoquinolin-5-amine, Intermediate 27

A mixture of 5-bromoisoquinoline (1 mole equivalent), palladium acetate (0.15 mole equivalent), R-(+)-2,2'-bis(diphenylphosphino)-1,1'-binaphthyl (0.15 mole equivalent), and cesium carbonate (1.6 mole equivalent) in toluene (10 mL per gram of 5-bromoisoquinoline) is purged with nitrogen and stirred at 80° C. for 30 min. A solution of (1RS,3rs,5SR)-tert-butyl 3-amino-8-azabicyclo[3.2.1]octane-8-carboxylate (1.2 mole equivalent) in a minimum volume of toluene is added, and the mixture is stirred at 80° C. for 18 h. An additional quantity of palladium acetate and phosphine ligand (0.03 equivalents each) is added, and heating is continued for an additional 18 h. The reaction mixture is partitioned between ethyl acetate and water, and the organic phase is dried over magnesium sulfate and evaporated to a residue. Chromatography of the residue on silica gel affords the title compound as the BOC-protected material.

The BOC-protected intermediate is taken up in 2.5M aqueous HCl (2 mL per mmol intermediate) and the mixture is stirred for 18 h. The mixture is diluted with methylene chloride, the pH of the aqueous phase is adjusted to 11 with 5M NaOH, and the organic phase is separated, dried over magnesium sulfate, and evaporated to a residue. Chromatography of the residue affords the title compound.

Examples 22-33

Reaction of 5-bromoisoquinoline with the indicated intermediate amines using the method of Example 16 affords the Intermediates 28-39, shown in Examples 22-33:

Example 22

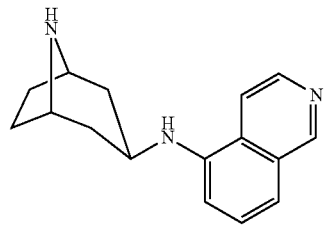 [SMILES: c1cc(NC2CC3CCC(C2)N3)c2ccncc2c1]

N-((1RS,3sr,5SR)-8-azabicyclo[3.2.1]octan-3-yl)isoquinolin-5-amine, Intermediate 28

Reaction of 5-bromoisoquinoline with (1RS,3sr,5SR)-tert-butyl 3-amino-8-azabicyclo[3.2.1]octane-8-carboxylate affords the BOC-protected coupling product, which is purified by chromatography. Subsequent treatment with acid removes the protecting group and affords the title amine.

Example 23

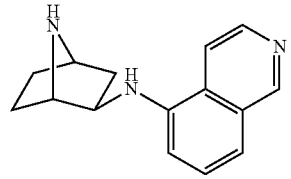 [SMILES: c1cc(NC2CC3CCC2N3)c2ccncc2c1]

N-((1SR,2RS,4RS)-7-azabicyclo[2.2.1]heptan-2-yl)isoquinolin-5-amine, Intermediate 29

Reaction of 5-bromoisoquinoline with (1SR,2RS,4RS)-tert-butyl 2-amino-7-azabicyclo[2.2.1]heptane-7-carboxylate (WO07110782) affords the BOC-protected coupling

Example 24

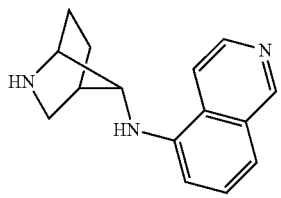 [SMILES: c1cc(NC2C3CCC2NC3)c2ccncc2c1]

N-((1SR,4SR,7RS)-2-azabicyclo[2.2.1]heptan-7-yl)
isoquinolin-5-amine, Intermediate 30

Reaction of 5-bromoisoquinoline with Intermediate 1 affords the BOC-protected coupling product, which is purified by chromatography. Subsequent treatment with acid removes the protecting group and affords the title amine.

Example 25

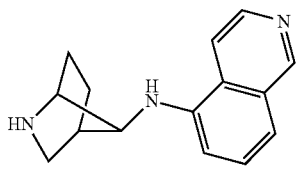 [SMILES: c1cc(NC2C3CCC2NC3)c2ccncc2c1]

N-((1SR,4SR,7SR)-2-azabicyclo[2.2.1]heptan-7-yl)
isoquinolin-5-amine, Intermediate 31

Reaction of 5-bromoisoquinoline with Intermediate 2 affords the BOC-protected coupling product, which is purified by chromatography. Subsequent treatment with acid removes the protecting group and affords the title amine.

Example 26

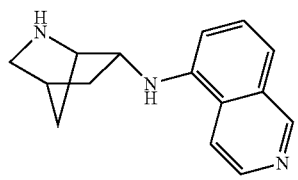 [SMILES: c1cc(NC2CC3CNC2C3)c2ccncc2c1]

N-((1SR,4SR,6SR)-2-azabicyclo[2.2.1]heptan-6-yl)
isoquinolin-5-amine, Intermediate 32

Reaction of 5-bromoisoquinoline with Intermediate 4 affords the BOC-protected coupling product, which is purified by chromatography. Subsequent treatment with acid removes the protecting group and affords the title amine.

Example 27

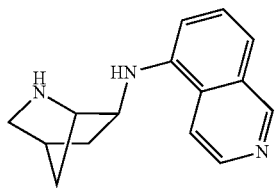 [SMILES: c1cc(NC2CC3CNC2C3)c2ccncc2c1]

N-((1SR,4SR,6RS)-2-azabicyclo[2.2.1]heptan-6-yl)
isoquinolin-5-amine, Intermediate 33

Reaction of 5-bromoisoquinoline with Intermediate 5 affords the BOC-protected coupling product, which is purified by chromatography. Subsequent treatment with acid removes the protecting group and affords the title amine.

Example 28

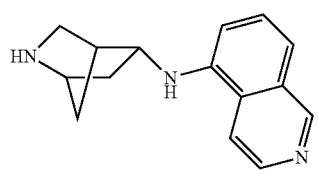 [SMILES: c1cc(NC2CC3CC2CN3)c2ccncc2c1]

N-((1RS,4RS,5SR)-2-azabicyclo[2.2.1]heptan-5-yl)
isoquinolin-5-amine, Intermediate 34

Reaction of 5-bromoisoquinoline with Intermediate 7 affords the BOC-protected coupling product, which is purified by chromatography. Subsequent treatment with acid removes the protecting group and affords the title amine.

Example 29

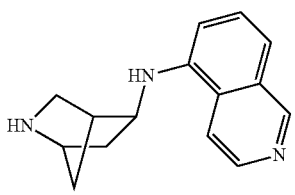 [SMILES: c1cc(NC2CC3CC2CN3)c2ccncc2c1]

N-((1RS,4RS,5RS)-2-azabicyclo[2.2.1]heptan-5-yl)
isoquinolin-5-amine, Intermediate 35

Reaction of 5-bromoisoquinoline with Intermediate 8 affords the BOC-protected coupling product, which is purified by chromatography. Subsequent treatment with acid removes the protecting group and affords the title amine.

Example 30

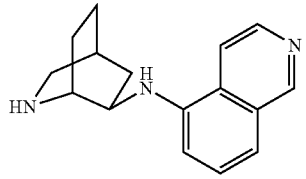 [SMILES: c1cc(NC2CC3CCC2NC3)c2ccncc2c1]

(1RS,4SR,6RS)—N-(isoquinolin-5-yl)-2-azabicyclo[2.2.2]octan-6-amine, Intermediate 36

Reaction of 5-bromoisoquinoline with Intermediate 10 affords the BOC-protected coupling product, which is purified by chromatography. Subsequent treatment with acid removes the protecting group and affords the title amine.

Example 31

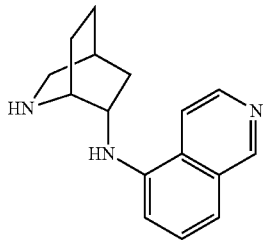 [SMILES: c1cc(NC2CC3CCC2NC3)c2ccncc2c1]

(1RS,4SR,6SR)—N-(isoquinolin-5-yl)-2-azabicyclo[2.2.2]octan-6-amine, Intermediate 37

Reaction of 5-bromoisoquinoline with Intermediate 11 affords the BOC-protected coupling product, which is purified by chromatography. Subsequent treatment with acid removes the protecting group and affords the title amine.

Example 32

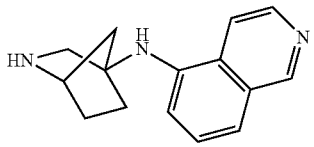 [SMILES: c1cc(NC23CCC(C2)NC3)c2ccncc2c1]

N-(2-azabicyclo[2.2.1]heptan-4-yl)isoquinolin-5-amine, Intermediate 38

Reaction of 5-bromoisoquinoline with Intermediate 12 affords the BOC-protected coupling product, which is purified by chromatography. Subsequent treatment with acid removes the protecting group and affords the title amine.

Example 33

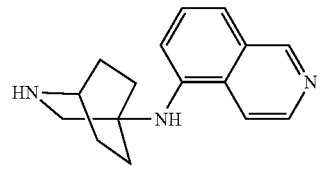 [SMILES: c1cc(NC23CCC(CC2)NC3)c2ccncc2c1]

N-(isoquinolin-5-yl)-2-azabicyclo[2.2.2]octan-4-amine, Intermediate 39

Reaction of 5-bromoisoquinoline with Intermediate 13 affords the BOC-protected coupling product, which is purified by chromatography. Subsequent treatment with acid removes the protecting group and affords the title amine.

Examples 34-36

Reaction of either 4-(4-aminophenyl)-1,2,5-oxadiazol-3-amine or 4-(3-aminophenyl)-1,2,5-oxadiazol-3-amine (prepared using the methods described in U.S. Ser. No. 08/021,4614) with the indicated intermediate ketones using the method of Example 11 affords the Intermediates 40-43, shown in Examples 34-36:

Example 34

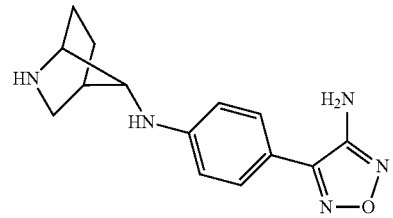 [SMILES: Nc1nonc1-c1ccc(NC2C3CCC2NC3)cc1]

4-(4-((1SR,4SR,7RS)-2-azabicyclo[2.2.1]heptan-7-ylamino)phenyl)-1,2,5-oxadiazol-3-amine, Intermediate 40

Reaction of 4-(4-aminophenyl)-1,2,5-oxadiazol-3-amine with 2-benzyl-2-azabicyclo[2.2.1]heptan-7-one (J. R. Malpass, S. Handa, and R. White, *Org. Lett.*, 2005, 7, 2759-2762) affords the title compound as the benzyl-protected amine. Purification by chromatography followed by removal of the benzyl group by hydrogenolysis affords the title amine.

Example 35

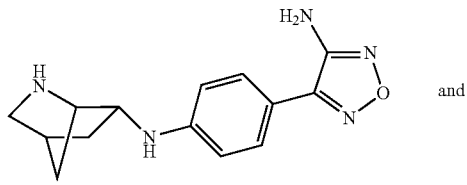

and

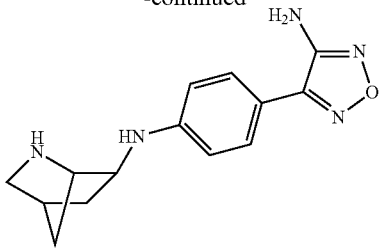

4-(4-((1SR,4SR,6SR)-2-azabicyclo[2.2.1]heptan-6-ylamino)phenyl)-1,2,5-oxadiazol-3-amine, Intermediate 41, and 4-(4-((1SR,4SR,6RS)-2-azabicyclo[2.2.1]heptan-6-ylamino)phenyl)-1,2,5-oxadiazol-3-amine, Intermediate 42

Reaction of 4-(4-aminophenyl)-1,2,5-oxadiazol-3-amine with benzyl 6-oxo-2-azabicyclo[2.2.1]heptane-2-carboxylate (J. Malpass and C. Cox, *Tetrahedron Lett.*, 1999, 40, 1419-1422) affords a mixture of the two diastereomeric title compounds as the CBZ-protected amines. Separation of the diastereomers by chromatography followed by removal of the CBZ group from the individual isomers by hydrogenolysis affords the title amines.

Example 36

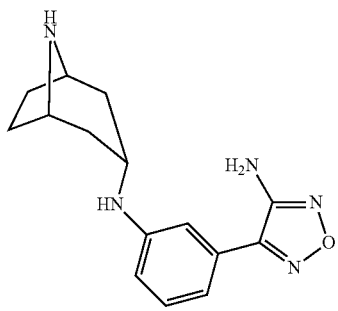 [SMILES: Nc1nonc1-c1cccc(NC2CC3CCC(C2)N3)c1]

4-(3-((1RS,3rs,5SR)-8-azabicyclo[3.2.1]octan-3-ylamino)phenyl)-1,2,5-oxadiazol-3-amine, Intermediate 43

Reaction of 4-(3-aminophenyl)-1,2,5-oxadiazol-3-amine with 8-benzyl-8-azabicyclo[3.2.1]octan-3-one affords the title compound as the benzyl-protected amine. Purification by chromatography followed by removal of the benzyl group by hydrogenolysis affords the title amine.

Example 37

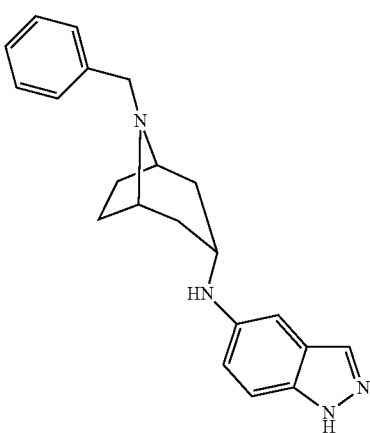 [SMILES: c1ccc(CN2C3CCC2CC(Nc2ccc4[nH]ncc4c2)C3)cc1]

N-((1RS,3rs,5SR)-8-benzyl-8-azabicyclo[3.2.1]octan-3-yl)-1H-indazol-5-amine, Compound 1.1.01

1-(5-((1RS,3rs,5SR)-8-benzyl-8-azabicyclo[3.2.1]octan-3-ylamino)-1H-indazol-1-yl)-2,2-dimethylpropan-1-one (900 mg, 2.2 mmol, prepared in Example 15) was dissolved in methanol (25 mL), potassium carbonate (1.0 g, 7.2 mmol) was added, and the mixture was stirred at ambient temperature for 2 days. When the reaction was complete as judged by HPLC, the mixture was partitioned between ethyl acetate and water, and the organic phase was dried over magnesium sulfate and evaporated to a residue. Recrystallization of the residue from methanol afforded the title compound (350 mg, 49%). NMR (CDCl$_3$) δ 9.83 (br s, 1H), 7.89 (s, 1H), 7.41-7.24 (m, 6H), 6.79-6.75 (d, 1H), 6.69 (s, 1H), 3.83 (br s, 1H), 3.68 (br s, 1H), 3.56 (s, 2H), 3.21 (m, 2H), 2.30-2.21 (m, 2H), 2.13-2.10 (m, 2H), 1.98-1.93 (m, 2H), 1.79-1.74 (m, 2H)

Example 38

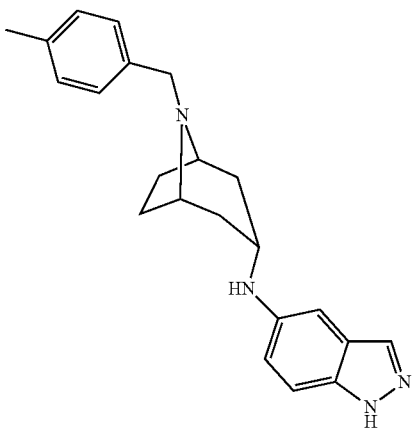 [SMILES: Cc1ccc(CN2C3CCC2CC(Nc2ccc4[nH]ncc4c2)C3)cc1]

N-((1RS,3rs,5SR)-8-(4-methylbenzyl)-8-azabicyclo[3.2.1]octan-3-yl)-1H-indazol-5-amine, Compound 1.1.02

A solution of Intermediate 21 (100 mg, 0.31 mmol) and 4-methylbenzaldehyde (48.6 mg, 0.40 mmol) in DMSO (1 mL) was treated with sodium triacetoxyborohydride (120 mg, 0.57 mmol), and the mixture was stirred for 18 h. Addition of water formed a precipitate, which was washed with water.

The precipitate was dissolved in methanol and was treated with potassium carbonate (300 mg, 0.22 mmol). The mixture was stirred overnight, after which it was diluted with ethyl acetate and washed with water. The organic phase was dried over magnesium sulfate and evaporated to a residue. Crystallization of the residue from methanol afforded the title compound (24 mg, 23%). $^1$H NMR (CDCl$_3$) δ 9.80 (br s, 1H), 7.90 (s, 1H), 7.34-7.29 (m, 2H), 7.18-7.13 (m, 2H), 6.80-6.67 (m, 2H), 3.80 (br s, 1H), 3.68 (br s, 1H), 3.52 (s, 2H), 3.20 (s, 2H), 2.38 (s, 3H), 2.32-2.20 (m, 2H), 2.18-2.04 (m, 2H), 1.98-1.92 (m, 2H), 1.80-1.72 (m, 2H)

Example 39

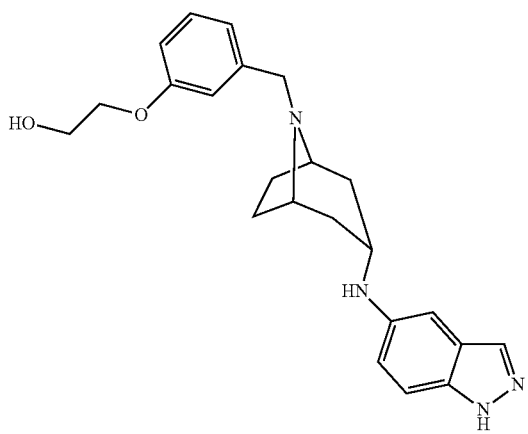 [SMILES: OCCOc1cccc(CN2C3CCC2CC(Nc2ccc4[nH]ncc4c2)C3)c1]

2-(3-(((1RS,3rs,5SR)-3-((1H-indazol-5-yl)amino)-8-azabicyclo[3.2.1]octan-8-yl)methyl)phenoxy)ethanol, Compound 1.1.03

Reaction of Intermediate 21 (100 mg, 0.31 mmol) with 3-(2-hydroxyethoxy)benzaldehyde (66 mg, 0.44 mmol) using the method described in Example 38 afforded the title compound (28 mg, 23%) after crystallization from methanol/water. $^1$H NMR (CDCl$_3$) δ 9.80 (br s, 1H), 7.90 (s, 1H), 7.35-7.20 (m, 2H), 7.08-6.94 (m, 2H), 6.82-6.69 (m, 3H), 4.14-4.08 (m, 2H), 4.00-3.94 (m, 2H), 3.90-3.72 (br s, 1H), 3.70-3.64 (m, 1H), 3.54 (s, 2H), 3.22-33.18 (m, 2H), 2.32-2.20 (m, 2H), 2.16-1.92 (m, 5H), 1.81-1.74 (m, 2H)

Example 40

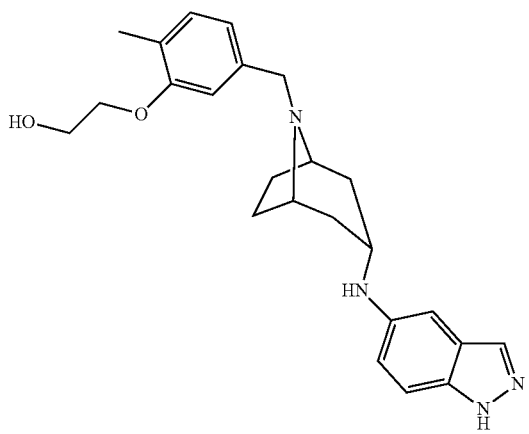 [SMILES: Cc1ccc(CN2C3CCC2CC(Nc2ccc4[nH]ncc4c2)C3)cc1OCCO]

2-(5-(((1RS,3rs,5SR)-3-((1H-indazol-5-yl)amino)-8-azabicyclo[3.2.1]octan-8-yl)methyl)-2-methylphenoxy)ethanol, Compound 1.1.04

Reaction of Intermediate 21 (120 mg, 0.40 mmol) with 3-(2-hydroxyethoxy)-4-methylbenzaldehyde (73 mg, 0.44 mmol) using the method described in Example 38 afforded the title compound (64 mg, 42%) after isolation by extraction into ethyl acetate and chromatography on silica gel. $^1$H NMR (CDCl$_3$) δ 9.80 (br s, 1H), 7.88 (s, 1H), 7.33-7.24 (m, 1H), 7.11-7.08 (m, 1H), 6.98 (s, 1H), 7.86-7.83 (m, 1H), 7.78-7.73 (m, 1H), 7.68 (s, 1H), 4.18-4.11 (m, 2H), 4.06-3.94 (m, 2H), 3.86-3.76 (br s, 1H), 3.72-3.65 (m, 1H), 3.52 (s, 2H), 3.22-3.18 (m, 2H), 2.30-2.19 (m, 5H), 2.16-1.90 (m, 5H), 1.80-1.73 (m, 2H)

Example 41

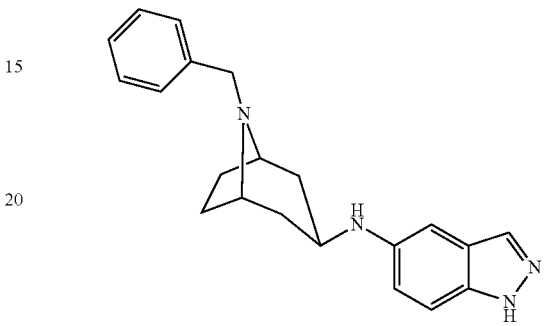

N-((1RS,3sr,5SR)-8-benzyl-8-azabicyclo[3.2.1]octan-3-yl)-1H-indazol-5-amine, Compound 2.1.01

Reaction of Intermediate 22 (145 mg, 0.60 mmol) with benzaldehyde (100 mg, 0.94 mmol) using the method described in Example 38, omitting the potassium carbonate treatment, afforded the title compound (80 mg, 40%) after isolation by extraction into ethyl acetate and chromatography on silica gel. $^1$H NMR (CDCl$_3$) δ 9.80 (br s, 1H), 7.90 (s, 1H), 7.41-7.20 (m, 6H), 6.82-6.78 (m, 2H), 3.73-3.59 (m, 3H), 3.30-3.24 (m, 2H), 2.18-1.98 (m, 4H), 1.79-1.70 (m, 2H), 1.60-1.50 (m, 2H)

Example 42

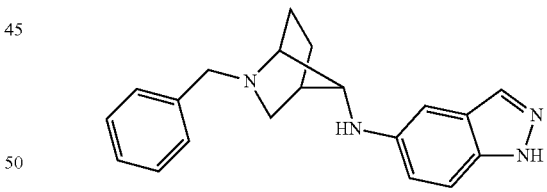

N-((1SR,4SR,7RS)-2-benzyl-2-azabicyclo[2.2.1]heptan-7-yl)-1H-indazol-5-amine, Compound 3.1.01

A solution of 1-(5-(((1SR,4SR,7RS)-2-benzyl-2-azabicyclo[2.2.1]heptan-7-ylamino)-1H-indazol-1-yl)-2,2-dimethylpropan-1-one (the intermediate benzyl compound of Example 11, 175 mg, 0.44 mmol) in methanol (2.5 mL) was treated with potassium carbonate (72 mg, 0.52 mmol), and the mixture was stirred for 18 h. The mixture was partitioned between ethyl acetate and water, and the organic phase was dried over sodium sulfate and evaporated to a residue. Chromatography of the residue on silica gel afforded the title compound (70 mg, 50%). $^1$H NMR (CDCl$_3$) δ 9.80 (br s, 1H), 7.88 (s, 1H), 7.39-7.21 (m, 6H), 6.92-6.85 (m, 2H), 3.80 (m, 1H), 3.63 (s, 1H), 3.16-3.12 (m, 2H), 2.40-2.37 (m, 1H), 2.04-1.96 (m, 2H), 1.85-1.76 (m, 2H), 1.60-1.40 (m, 2H)

Examples 43-108

Reaction of the indicated intermediate amines with aldehydes using the method of Example 37 affords the corresponding target compounds, as shown in Examples 43-108:

Example 43

N-((1RS,3rs,5SR)-8-(4-methylbenzyl)-8-azabicyclo[3.2.1]octan-3-yl)isoquinolin-5-amine, Compound 1.2.01

Reaction of Intermediate 27 with 4-methylbenzaldehyde affords the title compound.

Example 44

2-(5-(((1RS,3rs,5SR)-3-(isoquinolin-5-ylamino)-8-azabicyclo[3.2.1]octan-8-yl)methyl)-2-methylphenoxy)ethanol, Compound 1.2.02

Reaction of Intermediate 27 with 3-(2-hydroxyethoxy)-4-methylbenzaldehyde affords the title compound.

Example 45

4-(3-(((1RS,3rs,5SR)-8-(4-methylbenzyl)-8-azabicyclo[3.2.1]octan-3-yl)amino)phenyl)-1,2,5-oxadiazol-3-amine, Compound 1.3.01

Reaction of Intermediate 43 with 4-methylbenzaldehyde affords the title compound.

Example 46

N-((1RS,3sr,5SR)-8-(4-methylbenzyl)-8-azabicyclo[3.2.1]octan-3-yl)-1H-indazol-5-amine, Compound 2.1.02

Reaction of Intermediate 22 with 4-methylbenzaldehyde affords the title compound.

Example 47

2-(5-(((1RS,3sr,5SR)-3-((1H-indazol-5-yl)amino)-8-azabicyclo[3.2.1]octan-8-yl)methyl)-2-methylphenoxy)ethanol, Compound 2.1.03

Reaction of Intermediate 22 with 3-(2-hydroxyethoxy)-4-methylbenzaldehyde affords the title compound.

Example 48

N-((1RS,3sr,5SR)-8-(3-fluorobenzyl)-8-azabicyclo[3.2.1]octan-3-yl)-1H-indazol-5-amine, Compound 2.1.04

Reaction of Intermediate 22 with 3-fluorobenzaldehyde affords the title compound.

Example 49

N-((1RS,3sr,5SR)-8-(4-methylbenzyl)-8-azabicyclo[3.2.1]octan-3-yl)isoquinolin-5-amine, Compound 2.2.01

Reaction of Intermediate 28 with 4-methylbenzaldehyde affords the title compound.

Example 50

2-(5-(((1RS,3sr,5SR)-3-(isoquinolin-5-ylamino)-8-azabicyclo[3.2.1]octan-8-yl)methyl)-2-methylphenoxy)ethanol, Compound 2.2.02

Reaction of Intermediate 28 with 3-(2-hydroxyethoxy)-4-methylbenzaldehyde affords the title compound.

Example 51

N-((1SR,4SR,7RS)-2-(4-methylbenzyl)-2-azabicyclo[2.2.1]heptan-7-yl)-1H-indazol-5-amine, Compound 3.1.02

Reaction of Intermediate 14 with 4-methylbenzaldehyde affords the title compound.

Example 52

N-((1SR,4SR,7RS)-2-(4-chlorobenzyl)-2-azabicyclo[2.2.1]heptan-7-yl)-1H-indazol-5-amine, Compound 3.1.03

Reaction of Intermediate 14 with 4-chlorobenzaldehyde affords the title compound.

Example 53

N-(5-(((1SR,4SR,7RS)-7-((1H-indazol-5-yl)amino)-2-azabicyclo[2.2.1]heptan-2-yl)methyl)-2-methylphenyl)methanesulfonamide, Compound 3.1.04

Reaction of Intermediate 14 with N-(5-formyl-2-methylphenyl)methanesulfonamide affords the title compound.

Example 54

N-((1SR,4SR,7RS)-2-(4-methylbenzyl)-2-azabicyclo[2.2.1]heptan-7-yl)isoquinolin-5-amine, Compound 3.2.01

Reaction of Intermediate 30 with 4-methylbenzaldehyde affords the title compound.

Example 55

2-(5-(((1SR,4SR,7RS)-7-(isoquinolin-5-ylamino)-2-azabicyclo[2.2.1]heptan-2-yl)methyl)-2-methylphenoxy)ethanol, Compound 3.2.02

Reaction of Intermediate 30 with 3-(2-hydroxyethoxy)-4-methylbenzaldehyde affords the title compound.

Example 56

4-(4-(((1SR,4SR,7RS)-2-(4-methylbenzyl)-2-azabicyclo[2.2.1]heptan-7-yl)amino)phenyl)-1,2,5-oxadiazol-3-amine, Compound 3.3.01

Reaction of Intermediate 40 with 4-methylbenzaldehyde affords the title compound.

Example 57

N-((1SR,4SR,7SR)-2-(4-methylbenzyl)-2-azabicyclo[2.2.1]heptan-7-yl)-1H-indazol-5-amine, Compound 4.1.01

Reaction of Intermediate 23 with 4-methylbenzaldehyde affords the title compound.

Example 58

2-(5-(((1SR,4SR,7SR)-7-((1H-indazol-5-yl)amino)-2-azabicyclo[2.2.1]heptan-2-yl)methyl)-2-methylphenoxy)ethanol, Compound 4.1.02

Reaction of Intermediate 23 with 3-(2-hydroxyethoxy)-4-methylbenzaldehyde affords the title compound.

Example 59

N-((1SR,4SR,7SR)-2-(4-methylbenzyl)-2-azabicyclo[2.2.1]heptan-7-yl)isoquinolin-5-amine, Compound 4.2.01

Reaction of Intermediate 31 with 4-methylbenzaldehyde affords the title compound.

Example 60

N-(5-(((1SR,4SR,7SR)-7-(isoquinolin-5-ylamino)-2-azabicyclo[2.2.1]heptan-2-yl)methyl)-2-methylphenyl)methanesulfonamide, Compound 4.2.02

Reaction of Intermediate 31 with N-(5-formyl-2-methylphenyl)methanesulfonamide affords the title compound.

Example 61

N-((1SR,4SR,7SR)-2-(3-fluorobenzyl)-2-azabicyclo[2.2.1]heptan-7-yl)isoquinolin-5-amine, Compound 4.2.03

Reaction of Intermediate 31 with 3-fluorobenzaldehyde affords the title compound.

Example 62

N-((1SR,4SR,6SR)-2-(4-methylbenzyl)-2-azabicyclo[2.2.1]heptan-6-yl)-1H-indazol-5-amine, Compound 5.1.01

Reaction of Intermediate 16 with 4-methylbenzaldehyde affords the title compound.

Example 63

N-((1SR,4SR,6SR)-2-(3-methoxybenzyl)-2-azabicyclo[2.2.1]heptan-6-yl)-1H-indazol-5-amine, Compound 5.1.02

Reaction of Intermediate 16 with 3-methoxybenzaldehyde affords the title compound.

Example 64

2-(3-(((1SR,4SR,6SR)-6-((1H-indazol-5-yl)amino)-2-azabicyclo[2.2.1]heptan-2-yl)methyl)phenoxy)ethanol, Compound 5.1.03

Reaction of Intermediate 16 with 3-(2-hydroxyethoxy)benzaldehyde affords the title compound.

Example 65

N-((1SR,4SR,6SR)-2-(4-methylbenzyl)-2-azabicyclo[2.2.1]heptan-6-yl)isoquinolin-5-amine, Compound 5.2.01

Reaction of Intermediate 32 with 4-methylbenzaldehyde affords the title compound.

Example 66

N-(3-(((1SR,4SR,6SR)-6-(isoquinolin-5-ylamino)-2-azabicyclo[2.2.1]heptan-2-yl)methyl)phenyl)methanesulfonamide, Compound 5.2.02

Reaction of Intermediate 32 with N-(5-formyl-2-methylphenyl)methanesulfonamide affords the title compound.

Example 67

4-(4-(((1SR,4SR,6SR)-2-(4-methylbenzyl)-2-azabicyclo[2.2.1]heptan-6-yl)amino)phenyl)-1,2,5-oxadiazol-3-amine, Compound 5.3.01

Reaction of Intermediate 41 with 4-methylbenzaldehyde affords the title compound.

Example 68

N-((1SR,4SR,6RS)-2-(4-methylbenzyl)-2-azabicyclo[2.2.1]heptan-6-yl)-1H-indazol-5-amine, Compound 6.1.01

Reaction of Intermediate 15 with 4-methylbenzaldehyde affords the title compound.

Example 69

N-(3-(((1SR,4SR,6RS)-6-((1H-indazol-5-yl)amino)-2-azabicyclo[2.2.1]heptan-2-yl)methyl)phenyl)methanesulfonamide, Compound 6.1.02

Reaction of Intermediate 15 with N-(3-formylphenyl)methanesulfonamide affords the title compound.

Example 70

N-((1SR,4SR,6RS)-2-(4-methylbenzyl)-2-azabicyclo[2.2.1]heptan-6-yl)isoquinolin-5-amine, Compound 6.2.01

Reaction of Intermediate 33 with 4-methylbenzaldehyde affords the title compound.

Example 71

2-(3-(((1SR,4SR,6RS)-6-(isoquinolin-5-ylamino)-2-azabicyclo[2.2.1]heptan-2-yl)methyl)phenoxy)ethanol, Compound 6.2.02

Reaction of Intermediate 33 with 3-(2-hydroxyethoxy)benzaldehyde affords the title compound.

Example 72

N-((1SR,4SR,6RS)-2-(4-methoxybenzyl)-2-azabicyclo[2.2.1]heptan-6-yl)isoquinolin-5-amine, Compound 6.2.03

Reaction of Intermediate 33 with 4-methoxybenzaldehyde affords the title compound.

Example 73

4-(4-(((1SR,4SR,6RS)-2-(4-methylbenzyl)-2-azabicyclo[2.2.1]heptan-6-yl)amino)phenyl)-1,2,5-oxadiazol-3-amine, Compound 6.3.01

Reaction of Intermediate 42 with 4-methylbenzaldehyde affords the title compound.

Example 74

N-((1RS,4RS,5SR)-2-(4-methylbenzyl)-2-azabicyclo[2.2.1]heptan-5-yl)-1H-indazol-5-amine, Compound 7.1.01

Reaction of Intermediate 18 with 4-methylbenzaldehyde affords the title compound.

Example 75

2-(5-(((1RS,4RS,5SR)-5-((1H-indazol-5-yl)amino)-2-azabicyclo[2.2.1]heptan-2-yl)methyl)-2-methylphenoxy)ethanol, Compound 7.1.02

Reaction of Intermediate 18 with 3-(2-hydroxyethoxy)-4-methylbenzaldehyde affords the title compound.

Example 76

N-((1RS,4RS,5SR)-2-(3-chlorobenzyl)-2-azabicyclo[2.2.1]heptan-5-yl)-1H-indazol-5-amine, Compound 7.1.03

Reaction of Intermediate 18 with 3-chlorobenzaldehyde affords the title compound.

Example 77

N-((1RS,4RS,5SR)-2-(4-methylbenzyl)-2-azabicyclo[2.2.1]heptan-5-yl)isoquinolin-5-amine, Compound 7.2.01

Reaction of Intermediate 34 with 4-methylbenzaldehyde affords the title compound.

Example 78

N-(5-(((1RS,4RS,5SR)-5-(isoquinolin-5-ylamino)-2-azabicyclo[2.2.1]heptan-2-yl)methyl)-2-methylphenyl)methanesulfonamide, Compound 7.2.02

Reaction of Intermediate 34 with N-(5-formyl-2-methylphenyl)methanesulfonamide affords the title compound.

Example 79

N-((1RS,4RS,5RS)-2-(4-methylbenzyl)-2-azabicyclo[2.2.1]heptan-5-yl)-1H-indazol-5-amine, Compound 8.1.01

Reaction of Intermediate 17 with 4-methylbenzaldehyde affords the title compound.

Example 80

N-(5-(((1RS,4RS,5RS)-5-((1H-indazol-5-yl)amino)-2-azabicyclo[2.2.1]heptan-2-yl)methyl)-2-methylphenyl)methanesulfonamide, Compound 8.1.02

Reaction of Intermediate 17 with N-(5-formyl-2-methylphenyl)methanesulfonamide affords the title compound.

Example 81

N-((1RS,4RS,5RS)-2-(4-methylbenzyl)-2-azabicyclo[2.2.1]heptan-5-yl)isoquinolin-5-amine, Compound 8.2.01

Reaction of Intermediate 35 with 4-methylbenzaldehyde affords the title compound.

Example 82

2-(5-(((1RS,4RS,5RS)-5-(isoquinolin-5-ylamino)-2-azabicyclo[2.2.1]heptan-2-yl)methyl)-2-methylphenoxy)ethanol, Compound 8.2.02

Reaction of Intermediate 35 with 3-(2-hydroxyethoxy)-4-methylbenzaldehyde affords the title compound.

Example 83

N-((1RS,4RS,5RS)-2-(4-fluorobenzyl)-2-azabicyclo[2.2.1]heptan-5-yl)isoquinolin-5-amine, Compound 8.2.03

Reaction of Intermediate 35 with 4-fluorobenzaldehyde affords the title compound.

Example 84

N-((1SR,2RS,4RS)-7-(4-methylbenzyl)-7-azabicyclo[2.2.1]heptan-2-yl)-1H-indazol-5-amine, Compound 9.1.01

Reaction of Intermediate 24 with 4-methylbenzaldehyde affords the title compound.

Example 85

N-(5-((((1SR,2RS,4RS)-2-((1H-indazol-5-yl)amino)-7-azabicyclo[2.2.1]heptan-7-yl)methyl)-2-methylphenyl)methanesulfonamide, Compound 9.1.02

Reaction of Intermediate 24 with N-(5-formyl-2-methylphenyl)methanesulfonamide affords the title compound.

Example 86

N-((1SR,2RS,4RS)-7-(4-methoxybenzyl)-7-azabicyclo[2.2.1]heptan-2-yl)-1H-indazol-5-amine, Compound 9.1.03

Reaction of Intermediate 24 with 4-methoxybenzaldehyde affords the title compound.

Example 87

N-((1SR,2RS,4RS)-7-(4-methylbenzyl)-7-azabicyclo[2.2.1]heptan-2-yl)isoquinolin-5-amine, Compound 9.2.01

Reaction of Intermediate 29 with 4-methylbenzaldehyde affords the title compound.

Example 88

2-(5-(((1SR,2RS,4RS)-2-(isoquinolin-5-ylamino)-7-azabicyclo[2.2.1]heptan-7-yl)methyl)-2-methylphenoxy)ethanol, Compound 9.2.02

Reaction of Intermediate 29 with 3-(2-hydroxyethoxy)-4-methylbenzaldehyde affords the title compound.

Example 89

(1RS,4SR,6RS)—N-(1H-indazol-5-yl)-2-(4-methylbenzyl)-2-azabicyclo[2.2.2]octan-6-amine, Compound 10.1.01

Reaction of Intermediate 20 with 4-methylbenzaldehyde affords the title compound.

Example 90

2-(5-(((1RS,4SR,6RS)-6-((1H-indazol-5-yl)amino)-2-azabicyclo[2.2.2]octan-2-yl)methyl)-2-methylphenoxy)ethanol, Compound 10.1.02

Reaction of Intermediate 20 with 3-(2-hydroxyethoxy)-4-methylbenzaldehyde affords the title compound.

Example 91

(1RS,4SR,6RS)—N-(isoquinolin-5-yl)-2-(4-methylbenzyl)-2-azabicyclo[2.2.2]octan-6-amine, Compound 10.2.01

Reaction of Intermediate 36 with 4-methylbenzaldehyde affords the title compound.

Example 92

N-(5-((((1RS,4SR,6RS)-6-(isoquinolin-5-ylamino)-2-azabicyclo[2.2.2]octan-2-yl)methyl)-2-methylphenyl)methanesulfonamide, Compound 10.2.02

Reaction of Intermediate 36 with N-(5-formyl-2-methylphenyl)methanesulfonamide affords the title compound.

Example 93

(1RS,4SR,6RS)-2-(4-chlorobenzyl)-N-(isoquinolin-5-yl)-2-azabicyclo[2.2.2]octan-6-amine, Compound 10.2.03

Reaction of Intermediate 36 with 4-chlorobenzaldehyde affords the title compound.

Example 94

(1RS,4SR,6SR)—N-(1H-indazol-5-yl)-2-(4-methylbenzyl)-2-azabicyclo[2.2.2]octan-6-amine, Compound 11.1.01

Reaction of Intermediate 19 with 4-methylbenzaldehyde affords the title compound.

Example 95

2-(5-(((1RS,4SR,6SR)-6-((1H-indazol-5-yl)amino)-2-azabicyclo[2.2.2]octan-2-yl)methyl)-2-methylphenoxy)ethanol, Compound 11.1.02

Reaction of Intermediate 19 with 3-(2-hydroxyethoxy)-4-methylbenzaldehyde affords the title compound.

Example 96

(1RS,4SR,6SR)—N-(1H-indazol-5-yl)-2-(3-methylbenzyl)-2-azabicyclo[2.2.2]octan-6-amine, Compound 11.1.03

Reaction of Intermediate 19 with 3-methylbenzaldehyde affords the title compound.

Example 97

(1RS,4SR,6SR)—N-(isoquinolin-5-yl)-2-(4-methylbenzyl)-2-azabicyclo[2.2.2]octan-6-amine, Compound 11.2.01

Reaction of Intermediate 35 with 4-methylbenzaldehyde affords the title compound.

Example 98

N-(5-(((1RS,4SR,6SR)-6-(isoquinolin-5-ylamino)-2-azabicyclo[2.2.2]octan-2-yl)methyl)-2-methylphenyl)methanesulfonamide, Compound 11.2.02

Reaction of Intermediate 35 with N-(5-formyl-2-methylphenyl)methanesulfonamide affords the title compound.

Example 99

N-(2-(4-methylbenzyl)-2-azabicyclo[2.2.1]heptan-4-yl)-1H-indazol-5-amine, Compound 12.1.01

Reaction of Intermediate 25 with 4-methylbenzaldehyde affords the title compound.

Example 100

N-(5-((-4-((1H-indazol-5-yl)amino)-2-azabicyclo[2.2.1]heptan-2-yl)methyl)-2-methylphenyl)methanesulfonamide, Compound 12.1.02

Reaction of Intermediate 25 with N-(5-formyl-2-methylphenyl)methanesulfonamide affords the title compound.

Example 101

N-(2-(4-methylbenzyl)-2-azabicyclo[2.2.1]heptan-4-yl)isoquinolin-5-amine, Compound 12.2.01

Reaction of Intermediate 38 with 4-methylbenzaldehyde affords the title compound.

Example 102

2-(5-((4-(isoquinolin-5-ylamino)-2-azabicyclo[2.2.1]heptan-2-yl)methyl)-2-methylphenoxy)ethanol, Compound 12.2.02

Reaction of Intermediate 38 with 3-(2-hydroxyethoxy)-4-methylbenzaldehyde affords the title compound.

Example 103

N-(2-(3-chlorobenzyl)-2-azabicyclo[2.2.1]heptan-4-yl)isoquinolin-5-amine, Compound 12.2.03

Reaction of Intermediate 38 with 3-chlorobenzaldehyde affords the title compound.

Example 104

N-(1H-indazol-5-yl)-2-(4-methylbenzyl)-2-azabicyclo[2.2.2]octan-4-amine, Compound 13.1.01

Reaction of Intermediate 26 with 4-methylbenzaldehyde affords the title compound.

Example 105

2-(5-((4-((1H-indazol-5-yl)amino)-2-azabicyclo[2.2.2]octan-2-yl)methyl)-2-methylphenoxy)ethanol, Compound 13.1.02

Reaction of Intermediate 26 with 3-(2-hydroxyethoxy)-4-methylbenzaldehyde affords the title compound.

Example 106

N-(1H-indazol-5-yl)-2-(3-methoxybenzyl)-2-azabicyclo[2.2.2]octan-4-amine, Compound 13.1.03

Reaction of Intermediate 26 with 3-methoxybenzaldehyde affords the title compound.

Example 107

N-(isoquinolin-5-yl)-2-(4-methylbenzyl)-2-azabicyclo[2.2.2]octan-4-amine, Compound 13.2.01

Reaction of Intermediate 39 with 4-methylbenzaldehyde affords the title compound.

Example 108

N-(5-((4-(isoquinolin-5-ylamino)-2-azabicyclo[2.2.2]octan-2-yl)methyl)-2-methylphenyl)methanesulfonamide, Compound 13.2.02

Reaction of Intermediate 39 with N-(5-formyl-2-methylphenyl)methanesulfonamide affords the title compound.

Example 109

Rho kinase Inhibition Assay

Inhibition of Rho kinase 2 and Rho kinase 1 activity was determined using the IMAP™ Screening Express Kit (Molecular Devices product number #8073). Rho kinase 2 enzyme (Upstate/Chemicon #14-451), Rho kinase 1 (Upstate/Chemicon #14-601) and Flourescein tagged substrate peptide Fl-AKRRRLSSLRA (Molecular Devices product number R7184) was pre-incubated with a test compound for 5 minutes in buffer containing 10 mM Tris-HCl pH 7.2, 10 mM $MgCl_2$, and 0.1% BSA. Following the pre-incubation, 10 µM ATP was added to initiate the reaction. After 60 minutes at room temperature, Molecular Devices IMAP™ binding solution was added to bind phosphorylated substrate. After 30 minutes of incubation in the presence of the IMAP™ beads, the fluorescence polarization was read and the ratio was reported as mP. $IC_{50}$ values for compounds and $EC_{50}$ values for ATP were calculated using the Prism software from Graphpad.

This assay demonstrates a compound's ability to inhibit Rho kinase 2 in an in vitro setting using the isolated enzyme. All of the compounds studied inhibited Rho kinase 1 and Rho kinase 2 with Ki values below 1 µM, many of these inhibiting below 100 nM.

TABLE II

Rho kinase Assay Data.

| Compound | Rho kinase 1 Ki, nM | Rho kinase 2 Ki, nM |
|---|---|---|
| 1.1.01 | 72 | 29 |
| 1.1.02 | 91 | 20 |
| 1.1.03 | 59 | 21 |
| 1.1.04 | 35 | 10 |
| 2.1.01 | 806 | 220 |
| 3.1.01 | 976 | 464 |

Example 110

NIH/3T3 Cell Morphology Assay

NIH/3T3 cells are grown in DMEM-H containing glutamine and 10% Colorado Calf Serum. Cells are passaged regularly prior to reaching confluence. Eighteen to 24 hours prior to experimentation, the cells are plated onto Poly-L-Lysine-coated glass bottom 24-well plates. On the day of experimentation, the cell culture medium is removed and is replaced with the same medium containing from 10 nM to 25 µM of the test compound, and the cells are incubated for 60 minutes at 37° C. The culture medium is then removed and the cells are washed with warmed PBS and fixed for 10 minutes with warmed 4% paraformaldehyde. The cells are permeabilized with 0.5% Triton-X, stained with TRITC-conjugated phalloidin and imaged using a Nikon Eclipse E600 epifluorescent microscope to determine the degree of actin disruption. Results are expressed as a numerical score indicating the observed degree of disruption of the actin cytoskeleton at the test concentration, ranging from 0 (no effect) to 4 (complete disruption), and are the average of at least 2 determinations.

Active compounds show measurable activity in the cell morphology assay, providing substantial effects on the actin cytoskeleton at the testing concentration (score of 2 at 1 µM). The assay demonstrates that a compound's in vitro Rho kinase inhibition activity can manifest itself in morphology changes, such as actin stress fiber disassembly and alteration in focal adhesions in intact cells leading to inhibition of acto-myosin driven cellular contraction. These morphology changes are thought to provide the basis for the beneficial pharmacological effects sought in the setting of the disease processes described in this application

Example 111

Human Neutrophil Chemotaxis

Neutrophils are thought to contribute actively to the pathogenesis of allergic conjunctivitis, asthma and COPD. The infiltration and presence of inflammatory cells such as macrophages and neutrophils in the airway is considered to be a hallmark of COPD. Neutrophils can contribute to the pathogenic features of COPD through generation of reactive oxygen intermediates, increased secretion of mucus, elastolytic enzymes, metalloproteases, and myeloperoxidase (Beeh, K M. *Clinical and Experimental Allergy*. 36: 142-157, 2006). Although allergic asthma has been more strongly correlated with the presence of eosinophils, neutrophils are also present in the asthmatic airway and are activated and are able to release mediators that promote and prolong asthma symptoms. Increasing evidence suggests that neutrophils may be central players with an important role in the pulmonary inflammatory process present in asthma ((MacDowell, A L. *Current Allergy and Asthma Reports*. 7: 464-468, 2007). Inhibition of Rho kinase in vitro has been shown in the literature to inhibit the chemotactic peptide induced migration of human neutrophils (Niggli, V. *FEBS Letters*. 445: 69-72. 1999).

Peripheral blood from healthy human volunteers is collected and the neutrophils are isolated by Ficoll-paque density centrifugation followed by dextran sedimentation and hypotonic lysis of the red blood cells. Neutrophil chemotaxis is assessed using a modified Boyden Chamber (Neuroprobe, 96-well) with a 3 µm pore polycarbonate membrane. The ability of the tested compounds to block chemotaxis induced by a 1 µM fMLP challenge during a one hour incubation at 37° C. with 5% $CO_2$ is assessed in a dose response manner.

The results demonstrate that Rho kinase inhibition by Formula I compounds inhibited human neutrophil migration toward a chemotactic stimulant in vitro.

Example 112

Human Eosinophil Chemotaxis

Eosinophils are known to play a pivotal role in the pathogenesis of allergic asthma and conjunctivitis. Eosinophils are a major source of growth factors, lipids, basic granule proteins, cytokines and chemokines that contribute to the asthmatic disease state. Although infiltration and activation of other inflammatory cells actively contribute, it is the chemotaxis of eosinophils that is considered to be the single most important event in the pathogenesis of allergic inflammation. (See Adachi, T et. al., *The Journal of Immunology*. 167: 4609-4615, 2001.)

Human Eosinophil Isolation

Peripheral blood from healthy human volunteers is collected and the PMNs are separated via Ficoll-paque density centrifugation followed by hypotonic lysis of the red blood cells. Subsequently, the human eosinophils are isolated from the cell suspension via StemCell Technologies Human Eosinophil Enrichment kit (Cat. No 19256) according to the manufacturer's recommendations. Briefly, unwanted cells are specifically labeled with dextran-coated magnetic nanoparticles using bispecific Tetrameric Antibody Complexes (TAC) directed against cell surface antigens on human blood cells: CD2, CD3, CD14, CD16, CD19, CD20, CD36, CD56, CD123, glycophorin A and dextran. The unwanted cells are then separated from the unlabelled eosinophils using the EasySep® magnetic isolation procedure.

In Vitro Chemotaxis

Eosinophil chemotaxis is assessed using a modified Boyden Chamber (Neuroprobe, 96-well) with a 5 µm pore membrane. The ability of the tested compounds to block chemotaxis induced by a 10 nM eotaxin challenge (mouse) or 1 nM eotaxin challenge (human) during one hour incubation at 37° C. with 5% $CO_2$ is assessed. Chemotaxis is quantified via microscopy by counting the number of migrated cells in at least 3 view fields per treatment. The results demonstrate that chemotaxis is induced by eotaxin and that the chemotactic response is subsequently inhibited by Rho kinase inhibitor compounds.

Example 113

Human Monocyte Cytokine Secretion Assay

Relevance:

This assay demonstrates a compound's ability to inhibit the secretion of multiple pro-inflammatory cytokines from human monocytes. Reduction in the levels of pro-inflammatory cytokines is associated with improvement in disorders with an inflammatory component.

Protocol

Peripheral blood from healthy human volunteers is collected and the monocytes are isolated via Ficoll-paque density centrifugation. Monocytes are purified via an Easy Sep© Monocyte Enrichment Kit (Product number 19059) according to the manufacturer's instructions. The purified monocytes are then plated in 96-well plates at a density of 300,000 cells/mL in RPMI 1640+10% heat inactivated FBS media. The cells are allowed to pre-incubate with test compound for 30 minutes (37° C., 5% $CO_2$, humidified air); after which the supernatant is removed and media containing compound and 1 ng/mL LPS is added. Cells are allowed to incubate with compounds and LPS for 4 hours at 37° C. after which the supernatant is removed and stored at −80° C. Cytokine concentrations in the supernatant are determined using commercially available Bio-Rad Bio-plex™ kits according the manufacturer's instructions. Compounds of Formula I inhibit the release of multiple cytokines from human monocytes.

Example 114

Intraocular Pressure Pharmacodynamic Assay

Adult cynomolgus monkeys of both sexes are studied. All experiments are conducted in accordance with the ARVO Statement for the Use of Animals in Ophthalmic and Vision Research and in compliance with National Institutes of Health.

Prior to study inclusion a trained ophthalmologist performs a slit lamp examination to determine the integrity of the corneal epithelium and endothelium, presence of flare or cells in the AC, and clarity of the lens. All animals are free of ocular abnormalities when studied.

Following baseline IOP measurements, freshly prepared formulations containing vehicle (10 mM acetate buffered saline containing 0.01% benzalkonium chloride and 0.05% EDTA, pH 4.5) and one of the test compounds or vehicle alone are topically administered to the central cornea of supine animals as two 20 µl drops at 30 second intervals with blinking prevented between drops. Animals are treated twice daily for 3.5 days at 8 AM and 4 PM. Following administration, IOP is measured every hour for 6 hours using a minified Goldmann applanation tonometer. Slit lamp exams are conducted at 3 and 6 hours. The intraocular pressure of animals after treatment with the test compounds or vehicle at day 1 and day 4 from hour 0 to hour 6 is plotted.

This pharmacodynamic assay shows that compounds are able to achieve meaningful reductions in intraocular pressure when dosed topically in normotensive primates. It further shows that the compounds are well-tolerated on the ocular surface when dosed in a therapeutically relevant fashion. Reduction in intraocular pressure in this way is the primary objective of current glaucoma therapy. The assay described here is the most widely accepted method for the preclinical evaluation of intraocular pressure lowering agents.

Example 115

Increase of Endothelial Integrity and Decrease in Endothelial Permeability Following Treatment with Compounds of this Invention Endothelial integrity is crucial in the regulation of movement of fluid and extravasation of leukocytes/inflammatory cells into tissue. Increased endothelial integrity leads to decreased fluid movement and decreased extravasation of leukocytes into tissue thus resulting in decreased tissue edema (Dudek S M et al., *J Appl Physiol,* 91:1487-1500, 2001 and Vandenbroucke E et al., *Ann NY Acad Sci,* 1123:134-145, 2008).
Protocol The assay is conducted essentially as in Tasaka S et al. *Am J Resp Cell Mol Biol,* 32:503-510, 2004. Pulmonary artery endothelial cells (PAECs) are collected and cultured in a humidified 5% $CO_2$ atmosphere in the medium provided by the manufacturer supplemented with 2% fetal calf serum. Endothelial cell monolayers are prepared on filters. In brief, tissue culture plate well inserts are incubated with bovine fibronectin at 37° C. for three hours to facilitate cell attachment. The fibronectin solution is aspirated, and the endothelial cells are suspended in the culture medium that is placed on a membrane filter at a density of $4 \times 10^5$ cells per filter insert. The inserts are placed into a 6-well culture plate, where each individual well is filled with 2 ml of culture medium and incubated at 37° C. in a humidified 5% $CO_2$ atmosphere until PAECs reach confluence on the filter.

In order to measure permeability, the albumin that is transferred across a cultured endothelial cell monolayer grown on a porous filter is measured. PAECs on the filter are pretreated with 0.1 µM to 100 µM of a compound of Formula I for thirty minutes and then incubated with $10^2$ U/ml of TNF-alpha for six or twenty-four hours. Following the incubation, the TNF-alpha containing supernatant is aspirated and 500 µl of phosphate buffered saline (PBS) containing 0.1% bovine albumin is added to the chamber located on the top of the filter insert. The insert is then placed into a culture plate well which is filled with 0.7 ml of PBS. This PBS solution is now surrounding the filter insert and occupies the lower chamber. After incubation for twenty minutes, the insert is removed from the well. The albumin concentration of the lower chamber is measured with a protein assay kit.
Results The TNF-alpha induced permeability of the endothelial monolayer to albumin is decreased following the treatment of the EC monolayer with Formula I Rho kinase inhibitor compounds.

Example 116

Murine Model of Allergic Conjunctivitis

This example illustrates the efficacy of compounds of Formula I of this invention in treatment of allergic conjunctivitis (AC) in ragweed induced experimental allergic conjunctivitis. The model is prepared essentially as in Ozaki, A. et al. *The J. of Immunol.* 175:5489-5497, 2005.
Protocol Induction of experimental AC by active immunization. BALB/c or C57BL/6 mice (6-9 wk old) are systemically subcutaneously (s.c.) sensitized with ragweed (RW) emulsified in aluminum hydroxide hydrate gel on day 0. On days 7 and 14, mice are immunized intraperitoneally (i.p.) with RW (100 µg/mouse) in PBS. Rho kinase inhibitors are instilled three times daily for three days prior to challenge via eye drops (~2.5 µl) at concentrations ranging from 0.01-5%. A week after the second immunization, mice are challenged with RW (1 mg/5 µl PBS/eye) via eye drops. Clinical symptoms in the conjunctiva 15 and 30 min after administration of the challenge eye drop are evaluated as chemosis, redness, tearing, discharge, and scratching behavior, based on modified Draize criteria. Clinical appearance and photographs are evaluated by two masked observers. Scratching behavior is monitored for 30 seconds, and the frequency of scratching counted and evaluated as follows: one to three times, mild; four to six times, moderate; and more than seven times, severe. The final score is calculated as the sum of both eyes in each mouse. After 24 h, eyes are collected for histological analysis, and infiltrating cell number is counted in the conjunctiva. Vertical plane sections, including the optic nerve, are subjected to Giemsa and H&E staining.
Results Groups treated with Rho kinase inhibitor demonstrate improvements in at least one of the follow outcomes when compared with control animals: lid swelling, chemosis, redness, discharge, swelling, scratching as compared to control animals. Additionally histological assessments of eye vertical plane sections indicate attenuation of infiltration of inflammatory cells in Rho kinase inhibitor treatment groups as compared to controls.

Example 117

Promoting Effect on Neuritogenesis in Cultured Rabbit Trigeminal Nerve Cell

Restoration of corneal sensitivity in conditions leading to corneal hyposensitivity (such as following PRK and LASIK surgery and other corneal neuropathies) can be achieved by agents that induce neurotiogenesis. This example illustrates the efficacy of compounds of Formula I of this invention to induce neuritogenesis.
Protocol
The trigeminal nerve cell is isolated from 2-3 day-old NZW rabbits according to the report of Chan et al. (Chan, Kuan Y. and Haschke, Richard H., *Exp. Eye Res.*, 41: 687-699, 1985). Under ether anesthesia, after cardiac perfusion with saline, the trigeminal ganglia is removed, dispersed using a nerve dispersion solution to give a cell suspension. For the cell culture, Neurobasal medium supplemented with B27 Supplement (Invitrogen Corp., final concentration 2% v/v) and L-glutamine is used and the cultured conditions are 5% $CO_2$, 95% air at 37° C. The cells are seeded at about $3\times10^3$ cells/well on a cover glass with a polylysine/laminin coating, which is immersed in a 24 well plate. As the test substance, a Rho kinase inhibitor compound of Formula I is added, and the control group is free of addition. After 48 hr of culture, the cells are fixed with 4% paraformaldehyde at room temperature for 2 hr, and nerve cell body and neurite are fluorescence stained using an anti-neurofilament 200 antibody that specifically recognizes neurofilaments which are intermediate filaments specific to a nerve cell and a fluorescent secondary antibody reactive therewith. The stained cells are imported as images from a fluorescence microscope into a computer and the cell body diameter and neurite length of the imported cell images are measured using image analysis software. The cells of 3 wells are measured for each treatment group (kinase inhibitor and control). The cells having a neurite with a length of not less than twice the diameter of a cell body are taken as neuritogenetic cells, and the percentage (%) of the neuritogenetic cells in the total cells measured is calculated. Fluorescence microscope images of cultured rabbit trigeminal nerve cells demonstrate that not many cells in the non-treated control group had an extended neurite growth. However, in the kinase inhibitor-treated group, many cells have a long-extended neurite outgrowth and have a higher neuritogenetic cell percentage relative to the control group.

Example 118

Improving Effect on Rabbit Corneal Hyposensitivity Following Microkeratome Sectioning Protocol
New Zealand white rabbits are used. The animals are housed separately in cages in a room set to room temperature, 12 hr light cycle from arrival to the end of the test. Animals have a free access to pelletized food and tap water. Prior to the start of the test, the anterior segment of eye of the animal is visually observed and cornea stained marks by fluorescein observed, and the rabbits showing no abnormality are selected. Using Cochet-Bonnet corneal sensitivity meter, the initial value of corneal sensitivity is measured. Intramuscular injection ketamine and xylazine is given to the animals to perform systemic anesthesia, and the eyeball sufficiently exposed. Using a microkeratome, a corneal flap (diameter 8.5 mm) is prepared with a 130 μm thick blade (Arbelaez M C. et al., J. Refract Surg., May-Jun. 18, 2002 (3 Suppl): S357-60). The corneal flap is placed back into position under a microscope, and the animal woken from the anesthesia while observing the animal to prevent displacement of the flap. The next day, the condition of the animals is observed, and the animals having normally positioned corneal flap are selected.

The solution containing compounds of the Formula I and the control solution are administered by instillation for 1 week or 2 weeks from the next day of the corneal flap preparation. The instillation administration is performed to the surgery eye 4 times a day (30 instillations) at 2 hr intervals using a micropipette. Concurrently, the test substance is instilled 4 times every day for one week after the surgery, 0.1% Bromfenac sodium ophthalmic solution is instilled as an anti-inflammatory agent at the first and the third instillations and 0.3% ophthalmic solution of Lomefloxacin hydrochloride are instilled as an antibacterial agent at the second and the fourth instillations.

Corneal sensitivity is measured once every week from one to eight weeks after the surgery. The masked measurements are performed so that the operator will not know which administration group the subject rabbit belonged to. The corneal sensitivity is expressed by the maximal length of a nylon filament (diameter 0.12 mm) of Cochet-Bonnet corneal sensitivity meter, which induces a brink reflex upon contact of a tip of the filament with the center of the cornea. Administration of Rho-kinase inhibitor of Formula I promotes the recovery of corneal hyposensitivity due to corneal nerve section.

Example 119

Efficacy of a Compound of Formula I in Reducing Inflammation in Model of Lacrimal Gland Inflammation-Induced Dry Eye in Rabbits Protocol
The rabbit model of lacrimal gland inflammation-induced dry eye is used as an animal model of human dry eye disease. Rabbit lacrimal glands are injected with the T-cell mitogen Concanavalin A (Con A) to induce the conditions of dry eye. Measurements of inflammation, tear function, and corneal epithelial cell integrity are subsequently assessed as markers of efficacy. Matrix metalloproteinase-9 (MMP-9) and pro-inflammatory cytokines are quantified in tissue extracts. Tear function is monitored by measuring tear fluorescein clearance and tear breakup time (TBUT). Corneal epithelial cell integrity is determined by quantifying the uptake of methylene blue dye following the exposure of rabbits to a low humidity environment.

The compounds of Formula I in the concentration range 0.01-5% w/v or vehicle control is administered as a topical ophthalmic formulation with a positive displacement pipette in a volume of 30 μl alto rabbits randomly assigned into treatment groups and dosed topically 4 times per day (QID) at various times during (prophylactic) or after (therapeutic) lacrimal gland injection.
Results
Improvement in tear function and/or reduction of ocular surface injury or inflammation is observed in Compound-treated animals compared with vehicle-treated animals.

Example 120

Efficacy of Compounds of Formula I in reducing angiogenesis

Wet macular degeneration and edema is characterized by the accumulation of fluid in the macula as a result of leaky blood vessels. Angiogenesis, resulting in leaky blood vessels in the macula, can cause fluid retention leading to macular edema and wet macular degeneration. Reduction in angiogenesis or vascular permeability in the macula may help in the prevention of macular edema and wet macular degeneration.

Protocol: Directed In Vivo Angiogenesis Angioreactor

Sterile, surgical silicone tubing is cut to standard 1-cm lengths. These are plugged at one end, and sterilized by steam autoclave. These are referred to as "angioreactors." Using a Hamilton syringe, sterilized angioreactors are filled at 4° C. with 18 µl of Matrigel with or without angiogenic factors. These are incubated at 37° C. for 1 hour to allow gel formation, before subcutaneous implantation into the dorsal flank of C57/BL6, C57/BL6 MMP-2-deficient or athymic nude mice. Before collection of the angioreactors, mice receive a 100 µl injection of 25 mg/ml of FITC-dextran in phosphate-buffered saline (PBS) via tail vein. Quantification is performed by removal of the Matrigel and digestion in 200 µl of Dispase solution for 1 hour at 37° C. After digestion, the incubation mix is cleared by centrifugation in a benchtop centrifuge and fluorescence of the supernatant aliquots are measured in 96-well plates using an HP model spectrofluorimeter. The mean relative fluorescence ±SD is determined.

Characterization of Vascular Permeability During DIVAA

The contributions of vascular permeability to the FITC-dextran signal during quantification of angiogenic responses in the DIVAA assay are determined. The time course of FITC-dextran accumulation within the angioreactor in response to 500 ng/ml of either FGF-2 or VEGF is obtained at 9 days after implantation in angioreactors containing either FGF-2 or VEGF. Mice are injected intravenously with 100 µl of FITC-labeled dextran by tail vein. Angioreactors are then recovered at 10, 30, and 45 minutes and 1 hour after intravenous injection. FITC-dextran levels are assayed after Dispase digestion by fluorescence spectrometry as described (Guedez, et al. *Am J Pathol.* 162(5): 1431-1439).

Endothelial Cell Invasion Assay

FITC-labeled *Griffonia* lectin (FITC-lectin), an endothelial cell selective reagent, is used to quantify invading endothelial cells into the Matrigel. Briefly, after recovery of DIVAA angioreactors and digestion with Dispase as described above, cell pellets and insoluble fractions are collected by centrifugation. The cell pellets are resuspended in 1 ml of phosphate buffered saline (PBS) and washed three times with PBS. After the final wash the cells are again collected by centrifugation and resuspended in 200 µl of 25 µg/ml of FITC-lectin and incubated at 4° C. overnight. The stained cell pellets are again centrifuged and washed three times with cold PBS. The final pellet is resuspended in 100 µl and relative fluorescence is determined for triplicate assays as described above. Mean relative fluorescence units ±SD are determined as above (Guedez, et al. *Am J Pathol.* 162(5): 1431-1439).

Histological Examination

Nine days after implantation, angioreactors together with the immediate surrounding tissue are dissected and fixed in 10% neutral buffered formalin. Histological sections of paraffin-embedded assays are prepared by 10-µm sectioning and stained by conventional hematoxylin and eosin methods. Sections are also stained using *Griffonia* lectin (FITC-lectin). Stained sections are examined and photographed using a Zeiss Axioscope fluorescent microscope with a digital camera attachment (Spot model 1.3.0; Diagnostic Instruments, Sterling Heights, Mich.). The FITC-dextran signals within whole implants are examined using an inverted fluorescent microscope (Olympus 1×70) and photographed (Guedez, et al. *Am J. Pathol.* 162(5): 1431-1439).

Gelatinase Activity

Biochemical analysis of the gelatinase (MMP-2 and MMP-9) activity is performed by zymogram analysis. Matrigel is removed from recovered implants and resuspended in 200 al of PBS. After mechanical disruption with a pipette tip samples are centrifuged. Aliquots of the supernatant are prepared with 2× Novex Tris-glycine sample buffer (Invitrogen, Carlsbad, Calif.) and applied to Novex 10% zymogram gels. Electrophoresis and zymogram analysis are performed as previously described (Guedez, et al. *Am J Pathol.* 162(5): 1431-1439).

Dosing of Compounds of this Invention

Compounds of this invention are dosed i.p. or p.o. at the dose of 1 mg/kg to 100 mg/kg of body weight one to five times per day.

Results

Angiogenesis in this model examines the formation of neovasculature in the angioreactors of the test animals. Different contributing factors to angiogenesis are examined by DIVAA, characterization of vascular permeability, endothelial cell invasion, histological examination, and gelatinase activity. Improvement in at least one of the above-mentioned endpoints is observed in animals dosed with the compounds of Formula I.

Example 121

Efficacy of Compounds of Formula I in Treating Proliferative Vitreoretinopathy (PVR). Type I Collagen Gel Contraction Assay

The type I collagen gel contraction assay is used as an in vitro assay for studying the contractile properties of cells and is a surrogate assay for PVR. The contraction assay, previously described, (Ikuno Y, Kazlauskas A. et al. *Invest Ophthalmol Vis Sci.,* 43:41-46, 2002) is performed with slight modifications. Cells are suspended in 1.5 mg/mL neutralized collagen I at a density of $10^6$ cells/mL and transferred into a 24-well plate that has been preincubated with a solution of PBS and 5 mg/mL BSA overnight. The gel is solidified by incubating at 37° C. for 90 minutes, and then the well is flooded with EMEM and 5 mg/mL BSA. The cells are treated with 1 to 100 µM Rho kinase inhibitor compounds of Formula I or with control PBS. The gels are incubated at 37° C. with 5% $CO_2$. The initial gel diameter is 15 mm. The medium is replaced every 24 hours. The extent of contraction is calculated by subtracting the diameter of the well at a given time point from the initial diameter (15 mm).

Effect of Compounds on PVR in a Rabbit Model

PVR is induced in the left eyes of pigmented rabbits by using a gas vitrectomy technique by injection of 0.4 mL of $C_3F_8$ into the vitreous cavity 4 mm posterior to the corneal limbus after anesthesia is induced (Ikuno Y, Leong F L, Kazlauskas et al. *Invest Ophthalmol Vis Sci.,* 43:483-489, 2002). Ten days later, 0.1 mL of RPE medium containing $1 \times 10^5$ of retinal pigment epithelial (RPE) cells is injected into the vitreous cavity together with 0.1 mL of platelet-rich plasma (PRP), with a 30-gauge needle. The sixth-passage RPE cells are used in this model.

Compounds of this invention were dosed by direct injection of 50 µl of formulated compound or vehicle directly into the mid-vitreous cavity. In the treated group, the experimental eye of each rabbit is injected with sufficient Rho kinase inhibitor compound of Formula I dissolved in 0.05 mL physiological saline immediately after RPE cell injection to achieve a final intraocular concentration of approximately of 50 µM to 10 mM. For the control group, 0.05 mL saline solution is injected. Rabbits are treated in a similar manner on days 7, 14, and 21.

Each eye is examined by indirect ophthalmoscopy, and fundus video photographs are taken 3, 7, 14, 21, and 28 days after the RPE injection. The development of PVR is evaluated on videography in a masked fashion, and the PVR is graded according to the scale of Fastenberg et al. (Fastenberg D M, Diddie K R, Dorey K, Ryan S J. *Am J Ophthalmol*, 93:565-572, 1982).

Results

Treatment with compound significantly inhibits RPE-induced gel contraction in a dose-dependent manner. Rabbits that receive RPE and PRP followed by either compound or the control saline solution injection every week show significant improvements in at least one of the following outcomes: (1) decreased percentage of total retinal detachment; (2) lower PVR score.

Example 122

Efficacy of a Compound of Formula I in Reducing Inflammation in Rabbit Model of Meibomianitis, Blepharitis, and Conjunctivitis Blepharitis is accompanied by increased inflammation in the eye lid and the surrounding tissue. The following assays demonstrates efficacy of a Compound of Formula I in decreasing this inflammation.

New Zealand white rabbits are anesthetized with ketamine (100 mg/kg) and xylazine (10 mg/kg). Meibomian gland duct orifices are closed by cautery in the right eyes of all rabbits as previously described (Gilbard J P, et al. "Tear film and ocular surface changes after meibomian gland orifice closure in the rabbit." *Ophthalmology*, 96:1180-1186, 1989). Animals are divided into four treatment groups (designated groups I, II, III, and IV): group I receives no treatment; group II receives vehicle only four times a day for five days each week; group III receives tetracycline hydrochloride 1% (w/v) (Sigma Chemical, St. Louis, Mo.) four times a day for five days each week; and group IV receives a Compound of Formula I (between 0.01 and 5.0%, w/v) four times a day for five days each week. Treatments begin at 8 weeks post-op and continue until 20 weeks.

All rabbits are sacrificed at 20 weeks postoperatively by overdose with pentobarbital. At the time of death, corneal epithelium is removed for measurement of corneal epithelial glycogen level as previously described (Friend J et al. *Invest Ophthalmol Vis Sci*, 24:203-207, 1983; Sherwood M B et al. *Ophthalmology*, 96:327-335, 1989). Conjunctival biopsies are then taken for counting of goblet cell density as previously described (Gilbard J P et al. *Invest Ophthalmol Vis Sci*, 28:225-228, 1987). Lower eyelids are then removed by sharp dissection and placed in one-half strength Karnovsky's fixative. The tissue is dehydrated through graded alcohols and embedded in methacrylate. Three micron sections are cut through the eyelids horizontally for light microscopy, and stained with alkaline giemsa.

Leukocytes are quantified in tissue sections using a method similar to that described by Sherwood et al. (Sherwood M B et al. *Ophthalmology*, 96:327-335, 1989). For descriptive purposes, eyelid tissues are divided into three zones: 1) tarsal conjunctival epithelium, 2) underlying stroma, and 3) meibomian glands and adjacent tissue, including tarsal plate. Two separate sections, separated by a distance sufficient to provide two separate inflammatory cell populations, are examined for each eyelid. Leukocytes are identified as either neutrophils, eosinophils, basophils, or mast cells.

Twenty weeks after meibomian gland orifice closure, untreated rabbits have a significant increase in eyelid tissue mast cells, eosinophils, neutrophils and basophils relative to unoperated controls. Mast cells are not seen in the conjunctival epithelium of normal eyes nor after meibomian gland orifice closure. With this exception, all leukocyte types increase in all three tissue zones. Treatment with a Compound of Formula I decreases the number of leukocytes in the tissue when compared with vehicle-treated animals.

Example 123

Tracheal Relaxation Assay

Relevance

The mechanism by which bronchoconstricting agents induce smooth muscle contraction is known to involve the activation of Rho kinase (Yoshii et al, Am J Respir Cell Mol Biol 20:1190-1200 (1999)). These data demonstrate that inhibition of Rho pathways with the described compounds induces relaxation of smooth muscle. Since diseases accompanied by airway hyperreactivity and/or bronchoconstriction, such as asthma, COPD, RSV infection, LAM and IPF, involve a contraction of airway smooth muscle, agents that induce a relaxant response in the tracheal smooth muscle can be candidates for treatment of such diseases. Standard clinical treatments for respiratory disorders involving airway hyperreactivity and/or bronchoconstriction, such as albuterol, formoterol and salmeterol, have been shown to demonstrate relaxant properties in tracheal smooth muscle (Battram et al, J Pharmacol Exp Therap 317:762-770 (2006)). Therefore, the activity of the present compounds in this ex vivo model supports the use of these agents in diseases of airway hyperreactivity.

Protocol

The effects of compounds to induce relaxation of pre-contracted rat trachealis are determined. Male Sprague-Dawley rats weighing 301-325 gm are sacrificed by asphyxiation in a $CO_2$ chamber. Trachea are excised, cleaned of connective tissue and cut into cylindrical segments of 2-3 mm length. Two stainless steel wires are guided through the lumen of the tracheal ring. One wire is fixed in the tissue bath and the other is connected to a force transducer via surgical silk. Preparations are mounted in 5 ml water-jacketed organ baths (Radnoti Glass Technology) filled with Krebs buffer (95 mM NaCl, 5 mM KCl, 2.6 mM $CaCl_2$, 1.2 mM $MgSO_4$, 24.9 mM $NaHCO_3$, 1.2 mM $KH_2PO_4$, 10 mM glucose) maintained at 37° C. and gassed with 95% $O_2$ and 5% $CO_2$. Indomethacin (1 µM), a cyclooxygenase inhibitor, is added to the Krebs buffer and is present throughout the experiments. Contractile tensions are measured using an isometric force transducer and signals are analyzed using specialized software. The preparations are allowed to equilibrate at a resting tension of 0.3 to 0.5 gm prior to two challenges with 60 mM KCl to assess tissue viability. After washing, tissues are treated with 1 µM carbachol for 10 to 15 minutes to induce a contractile response. Rho kinase inhibitor compounds of this invention are added cumulatively to the bath every 30 minutes and reductions in tension are recorded.

Application of compounds of this invention to the tissue bath results in a reduction in contractile tension.

Example 124

Effect of Inflammatory Cytokines on Tracheal Relaxation

Relevance

Pulmonary disease such as asthma and COPD are accompanied by an inflammatory response in the lung that contributes to disease severity. These inflammatory cytokines can alter tissue function and may limit the efficacy of therapeutic interventions. Demonstration of compound efficacy in tissues that have been exposed to inflammatory cytokines in vitro supports the utility of these compounds as bronchorelaxants in disease states such as asthma that are accompanied by inflammation in vivo.

Protocol

Male Sprague-Dawley rats weighing 301-325 gm are sacrificed by asphyxiation in a $CO_2$ chamber. Trachea are excised, cleaned of connective tissue and cut into cylindrical segments of 2-3 mm length. Tissues are treated for 18 hours at 37° C. in F12 media with penicillin-streptomycin and 0.1% BSA alone or with 10 ng/ml IL-1β☐ and 100 ng/ml TNF-α. Tissues are then washed free of cytokines with Krebs buffer. Contractile tensions are measured using an isometric force transducer and signals are analyzed using specialized software. Tissues are treated with 300 nM carbachol for 10 to 15 minutes to induce a contractile response. Rho kinase inhibitor compounds of this invention are added cumulatively to the bath every 30 minutes and reductions in tension are recorded.

Compounds of this invention induce a relaxant response in vehicle-pretreated tissues as well as in cytokine-pretreated tissues.

Example 125

Pulmonary Arterial and Aortal Relaxation Assay

Relevance

Smooth muscle contractile responses mediate hypertensive disorders and currently marketed therapeutics for hypertensive disorders, such as iloprost, demonstrate efficacy in norepinephrine pre-contracted pulmonary arteries (Walch et al, Brit J Pharmacol 126:859-866 (1999)). Therefore, the results indicate that the compounds are good candidates for treating diseases that involve constriction of arterial smooth muscle, such as pulmonary arterial hypertension or systemic hypertension.

Protocol

The effects of compounds to induce relaxation of pre-contracted rat pulmonary artery and rat aorta are determined. Male Sprague-Dawley rats weighing 301-325 gm are sacrificed by asphyxiation in a $CO_2$ chamber. Pulmonary artery or aorta are excised, cleaned of connective tissue and cut into cylindrical segments of 2-3 mm length. The preparations are mounted in a tissue bath by tying two threads of surgical silk through the lumen of the vessel. One silk is used to anchor the tissue to a metal wire in the bath and the other silk is connected to a force transducer. Preparations are mounted in 5 ml water-jacketed organ baths filled with Krebs buffer (95 mM NaCl, 5 mM KCl, 2.6 mM $CaCl_2$, 1.2 mM $MgSO_4$, 24.9 mM $NaHCO_3$, 1.2 mM $KH_2PO_4$, 10 mM glucose) maintained at 37° C. and gassed with 95% $O_2$ and 5% $CO_2$. Contractile tensions are measured using an isometric force transducer. The preparations are allowed to equilibrate at a resting tension of 0.1 to 0.2 gm for pulmonary artery and 2.0 gm for aorta prior to two challenges with 80 mM KCl to assess tissue viability. After washing, tissues are treated with 100 nM norepinephrine for 5 to 10 minutes to induce a contractile response. Compounds of this invention are added to the tissue bath and reductions in tension are recorded.

Application of compounds of this invention to the tissue bath results in a reduction in contractile tension.

Example 126

LPS-Induced Neutrophilia Assay

Relevance

Marked neutrophilia in the lung upon tissue inflammation can be indicative of underlying diseases such as COPD. The LPS-induced neutrophilia model is often used to determine the potential efficacy of therapeutic approaches designed for treatment of COPD.

Protocol

Male BALB/c mice, approximately 19 to 21 grams, are challenged with aerosolized LPS (10 μg/ml) for 25 minutes on study day 0. LPS aerosol is generated using an Aerogen Aeroneb nebulizer and controller providing a flow of 400 μl/min and a particle size of 2-4 μm MMAD. Compounds of this invention are administered intratracheally or orally one hour prior to LPS challenge. Four hours following LPS challenge, BALF is collected using a total of 3 ml of 0.9% sodium chloride containing 10% fetal calf serum. Total cell counts are determined using the Coulter Counter. For differential evaluations, BALF is centrifuged and cytospin slides prepared and stained with Hema3 stain. Manual leukocyte counts are then completed on 200 cells. The final concentration of individual leukocyte cell types per ml of BALF is determined by multiplication of the relative percentage of individual leukocytes with the total amount of cells/ml of BALF fluid.

Results

A reduction in LPS-induced pulmonary neutrophilia influx is seen after administration of compounds of this invention.

Example 127

Bronchodilator Assay in Rodent Model of Asthma in Ovalbumin-Sensitized Mice The main functional changes of the lungs associated with pulmonary diseases such as asthma and chronic obstructive pulmonary disease (COPD) include malfunctioning of the immune system, cellular infiltration composed primarily of eosinophils and neutrophils, acute and chronic inflammation, fluid accumulation (edema), excessive secretion of mucus, and changes in the airway walls that could lead to bronchial epithelial injury, fibrosis, and increased sensitivity to agents that cause bronchial constriction. These features need to be considered in order to understand the development and mechanics of the disease, and to develop treatments of the underlying disease process. Small animal models can be designed to mimic the airway inflammation, increased responsiveness to bronchial constrictors, changes in the airway wall, and the migration of the eosinophils and neutrophils to the lungs. Such animal models provide valuable tools to evaluate the effects of experimental compounds on these disease characteristics (Kips et al. *Eur Respir J* 2003; 22:374-382; Isenberg-Feig, et al. *Current Allergy and Asthma Reports*. 2003; 3: 70-79). A mouse model of asthma via ovalbumin sensitization is used to evaluate bronchodilator efficacy of compounds of this invention.

Male BALB/c mice are randomized into groups of five males per cage and assigned to a dosing group. Animals are quarantined for 7 days under test conditions. Animals are sensitized on day 0 and 14 of study by an intraperitoneal injection with 20 μg of ovalbumin (ova) and 2.0 mg aluminum hydroxide which initiates the development of a specific T-helper (Th) cells type 2 resulting in asthmatic animals. One group of animals receives an injection of saline to use as non-asthmatic control animals. All animals are challenged with aerosolized 1% ova once daily for 25 minutes on days 28, 29, and 30 (Zosky, et al. *Respiratory Research.* 2004; 5:15). Aerosol challenge consists of using an Aerogen Aeroneb nebulizer and controller with a particle size of 4-6 μm mass median aerodynamic diameter (MMAD) with a distribution of 400 μl piper minute. This aerosol challenge is necessary to target the Th2-driven allergic inflammation in the lower airways. Airway hyperreactivity is measured upon methacholine challenge on day 32.

Compounds of this invention and the control vehicle are administered to animals on the day of airway hyperreactivity evaluation 30 minutes to 1 hour before the mathacholine challenge to determine the direct bronchodilator effects of the compounds. Compounds are administered p.o. (orally), i.p. (intraperitoneally) or i.t. (intratracheally) at varying doses. On day 32 of the experiment, airway hyperreactivity is evaluated by placing conscious, unrestrained animals in a whole body plethysmometer (Buxco Wilmington, N.C.) and exposing them to escalating doses of nebulized methacholine, a known bronchial constrictor which acts through the muscarinic receptors of the lungs, (doses: 0.325-50 mg/ml). Exposure to the methacholine doses consisted of a 3 minute period during which a nebulizer is aerosolizing the methacholine and an additional 3 minute period following the cessation of nebulization. Over this 6 minute period, the plethysmometer monitors and generates numerical values for all parameters of the breath pattern. Enhanced pause (Penh), a unitless index of airway hyperreactivity, is derived from the expiratory side of the respiratory waveform measured via the plethysmograph and is used as an indirect measure of airway resistance and hyperreactivity. Penh is an indicator of changes in resistance within the airways and has been shown to be a valid marker for airway responsiveness to allergen challenge (Hamelmann, et al. *Am J Respir Crit Care Med.* 1997; 156:768-775). Following the methacholine dose response, all animals were anesthetized, bled and euthanized.

Results

Evaluation of the pulmonary mechanics data shows a methacholine dose response trend of increased Penh levels. The ovalbumin-sensitized animals show a heightened response to the methacholine when compared to saline-sensitized animals, which indicates an asthma-like hyperresponsiveness to the broncho-constricting agent when compared to the nonsensitized control animals exposed to inhaled ovalbumin or completely naïve animals. Treating ovalbumin-sensitized, animals with Rho kinase inhibitors of this invention yields a reduction in airway hyperresponsivness.

Example 128

Anti-Inflammatory Assay in Rodent Model of Asthma in Ovalbumin-Sensitized Mice

Substantial evidence suggests that cytokines play an important role in orchestrating and regulating this inflammatory process through the involvement of T-helper type 2 lymphocytes. Characteristics of T-cell mediated inflammatory immune response are dependent on the cytokines predominating during the course of the disease. The Th2 cytokines are associated with eosinophils, mast cell activation and preferential switching to IgE production, all being elements of the immune system associated with response to allergens. Therefore, a reduction in the levels of cytokines identified as key players in pulmonary inflammation is an indication of treating pulmonary inflammation.

A mouse model of asthma via ovalbumin sensitization is created as described in Example 127. The anti-inflammatory dosing paradigm is utilized to evaluate the anti-inflammatory effects of compounds of this invention. The anti-inflammatory dosing paradigm consists of dosing the animals once a day starting on day 27 and finishing on day 30 (1 hr prior to the aerosolized ovalbumin challenges on days 28 to 30) but not on day 32 when hyper-reactivity evaluation occurs. On day 32, animals are monitored for pulmonary eosinophilia, cytokine production and airway hyperreactivity.

Assessment of Cell Counts and Inflammatory Cytokines in BALF

On day 32 lavage fluid (BALF) is collected by infusing 3.0 ml of saline with 10% fetal calf serum into the lungs via the trachea and then withdrawing the fluid. The total amount of cells/ml of BALF fluid is determined via manual cell count on hemocytometer. The BALF is centrifuged, supernatant is removed and analyzed for cytokine concentrations as described below, and cell pellet reconstituted in 500 μL of fluid. Cytospin slides are prepared from the cell pellet using 100 μL of fluid and spinning samples for 5 minutes at 5000 rpms in a cytospin centrifuge. Following Hema3 stain, relative percentages of individual leukocytes are determined on a 200 cell count for each sample. The final concentration of individual leukocyte cell types per ml of BALF is determined by multiplication of the relative percentage of individual leukocytes with the total amount of cells/ml of BALF fluid.

Evaluation of the differential counts performed on these samples show an increased number of inflammatory cells in the asthmatic animals. Mice treated with compounds of this invention according to the anti-inflammatory dosing paradigm show reduced eosinophil infiltration.

The concentrations of cytokines in the BALF samples are determined using commercially available Bio-plex kits (Bio-Rad) for the detection of mouse IL-5, IL-13, and Eotaxin. Mice treated with compounds of this invention according to the anti-inflammatory dosing paradigm show reduced levels of cytokines in BALF.

Prevention of Airway Hypperreactivity

Airway hyperreactivity is evaluated by placing conscious, unrestrained animals in a whole body plethysmometer (Buxco Wilmington, N.C.) and exposing them to escalating doses of nebulized methacholine on day 32. Administration of compounds of this invention once a day during days 27 to 30 results in prevention of airway hyperreactivity to metacholine dosed on day 32.

Example 129

Efficacy of Compounds in Animal Model of Idiopathic Pulmonary Fibrosis

This example illustrates the efficacy of compounds of this invention in treatment of IPF in bleomyocin-induced pulmonary fibrosis in mice.

Protocol

The model is based on the description in Shimizu Y et al. *Am. J. Resp. Crit. Care Med.* 163: 210-217, 2001. Pathogen-free 6-wk-old female C57BL/6 mice are used for the experiments. The animals are maintained under standard conditions with free access to water and rodent laboratory food. The animals receive bleomyocin (BLM) i.p. injections on day 0, 2, 4, 6 and 8 at a dose of 40 mg/kg. BLM accumulates in the subpleural regions, resulting in the preferential development of lung fibrosis at subpleural lesions. This is very similar to the pathological features of human IPF (Ekimoto H et al. *Gan To Kagaku Ryoho* 10:2550-2557, 1983). Body weights are measured before every administration of the compounds. A compound of Formula I is administered via i.p. administration every day at the dose of 1 mg/kg to 100 mg/kg of body weight starting on day 0 and continuing to day 40. A control group of animal receives i.p. saline.

At day 40, mice are sacrificed, and their thoraces are then exposed. The lungs are washed with cold phosphate-buffered saline (PBS) and surgically removed. The excised lungs are used for histopathological examination and assayed for OH-proline contents. The left lungs are used to evaluate the fibrotic score by histological examination, and the right lungs for measurement of OH-proline contents. Additional mice are used to determine cell differentiation in the lumen of the lung as determined by bronchoalveolar lavage (BAL). BAL is performed on Days 7, 14, 21, and 40 after initial injection of BLM. Mice are sacrificed, and BAL is performed.

Histologic Examination

Morphological evaluation of fibrotic changes in the lungs is performed on Day 40. The excised lungs are immediately fixed with 10% formaldehyde neutral buffer solution for 48 h, and then embedded in paraffin. Sagittal sections are cut at 2 mm thickness and stained with hematoxylin-eosin and Masson-trichrome. The total lung area of the sections is used for the fibrotic scale microscope evaluation (Olympus, BX50F4). Criteria for grading lung fibrosis are according to the method reported by Ashcroft and coworkers (Ashcroft T et al. *J Clin Pathol.* 41:467-470, 1988): Grade 0, normal lung; Grade 1, minimal fibrous thickening of alveolar or bronchiolar walls; Grade 3, moderate thickening of walls without obvious damage to the lung architecture; Grade 5, increased fibrous with definite damage to lung architecture and formation of fibrous bands or small fibrous masses; Grade 7, severe distortion of architecture and large fibrous area; Grade 8, total fibrous obliteration of the field. Severity of fibrotic changes in each lung section is assessed as the mean score for severity from the observed microscopic fields. The grade of lung fibrosis is scored on a scale from 0 to 8 by examining 20 randomly chosen regions per sample at a magnification of 3100. To minimize investigator variability, all histological specimens are randomly numbered and scored by another investigator in a single blinded fashion.

OH-Proline Assay

OH-proline contents of the lungs are measured objectively to estimate lung fibrosis (Green G D et al. *Anal Biochem.* 201:265-269, 1992). The right lungs of each mouse are dissected free from major bronchi, and the wet weights are measured. They are hydrolyzed in 500 ml of 12 N hydrochloric acid and in the same aliquot of distilled water at 110 C. 20 h, in dry block. After the resultant hydrolysate is neutralized with sodium hydroxide, a 100-ml supernatant is mixed in 1.5 ml of 0.3 N lithium hydroxide solution. The OH-proline content is determined by high-performance liquid chromatography (HPLC) and expressed as micrograms per right lung.

Bronchoalveolar Lavage and Cell Counting

Bronchoalveolar lavage fluid (BALF) is collected by infusing 3.0 ml of saline with 10% fetal calf serum into the lungs via the trachea and then withdrawing the fluid. The total amount of cells/ml of BALF fluid is determined via manual cell count on hemocytometer. The BALF is centrifuged, and cell pellet reconstituted in 500 µL of fluid. Cytospin slides are prepared from the cell pellet using 100 µL of fluid and spinning samples for 5 minutes at 5000 rpms in a cytospin centrifuge. Following Hema3 stain, relative percentages of individual leukocytes are determined on a 200 cell count for each sample. The final concentration of individual leukocyte cell types per ml of BALF is determined by multiplication of the relative percentage of individual leukocytes with the total amount of cells/ml of BALF fluid.

Results

At day 40 following the first BLM administration, the fibrotic changes in the lung, the hydroxyproline content in the lung, and the cell count of leukocytes (total cell count, macrophage cell count, lymphocyte cell count and/or nertrophil cell count) in BALF are measured and compared in the compound-treated mice vs. saline-treated mice. Improvement in at least one of the above-mentioned endpoints is observed with compound.

Example 130

Efficacy of Compounds in Treating RSV-Infection Induced Airway Hyperresponsiveness Protocol The experiment is conducted essentially as in Hashimoto K et al. *Thorax*, 57:524-527, 2002. In summary, ovalbumin (OVA) sensitized mice, which are also RSV infected, demonstrate prolonged methacholine-induced airway hyperresponsiveness (AHR) when compared to OVA sensitized mice without RSV infection. According to past observations, ovalbumin (OVA)-induced AHR lasted only a few days past the discontinuance of OVA aerosol in mice that were ovalbumin sensitized and mock infected. In contrast, OVA-sensitized mice infected with RSV during the OVA aerosol treatments (OVA/RSV) had AHR for more than 2 weeks after infection (Peebles R S et al. *J. Med. Virol.* 57(2):186-92, 1999).

Pathogen free 8 week old female BALB/c mice are used. The A2 strain of RSV virus is prepared as previously described in Graham B S et al. *J Med Virol* 26:153-62, 1998. Mice are injected intraperitoneally with 0.1 ml (10 µg) ovalbumin complexed with 2 mg $Al(OH)_3$ as previously described (Peebles R S et al. *J. Med. Virol.* 57(2):186-92, 1999). After 14 days, the mice are placed in an acrylic box and exposed to aerosols of 1% ovalbumin diluted in sterile phosphate buffered saline (PBS) using a nebulizer for 40 minutes each day for 8 days. Mice are infected with RSV (as previously described on day 3 of OVA inhalation (Peebles R S et al. *J. Med. Virol.* 57(2):186-92, 1999). Fourteen days after RSV inoculation (and 9 days after OVA inhalation), the mice undergo AHR testing via methacholine challenge. The mice are administered with Formula I compound i.p. at 1-100 mg/kg of body weight. AHR is measured one hour after the treatment (Peebles R S et al. *J. Med. Virol.* 57(2):186-92, 1999).

AHR Measurements

AHR is measured as previously described (Peebles R S et al. *J. Med. Virol.* 57(2):186-92, 1999). Methacholine is dissolved in normal saline and administered intravenously at starting doses of 5 µg/kg and 6.25 µg/kg, respectively. The mean volume per methacholine dose is approximately 35 µl and 50 µl, respectively. The methacholine concentration is increased in multiples of three in the dose response challenge with methacholine.

Results

Airway hyperresponsiveness is measured as described above. Improvement in AHR is observed in OVA-sensitized, RSV-infected animals treated with compounds of this invention when compared to OVA-sensitized, RSV-infected animals treated with vehicle.

Example 131

Efficacy of Compounds in Treating PAH

Protocol

The experiment is conducted essentially as in Abe K et al. *Circ. Res.* 94: 385-393, 2004. Male Sprague Dawley rats are administered either monocrotaline or vehicle. Each MCT-treated rat receives a single subcutaneous injection (right or left flank) of MCT (60 mg/kg body weight) on day 0. Control animals receive a single subcutaneous injection of vehicle. A compound of this invention is administered daily starting on day 0 and continued until necropsy. Groups of animals are sacrificed on Days 21, 28, and 63. A compound of Formula I is administered i.p. or p.o. at 1-100 mg/kg of body weight.

Right Ventricle (RV) Hypertrophy

The RV is dissected from the left ventricle (LV) plus the septum (S) and weighed to determine the extent of RV hypertrophy (RVH) as follows: RV/(LV+S)(Cowan K N et al. *Nat Med.* 6:698-702, 2000).

Survival Analysis

The effects of a compound of this invention on the survival of MCT-injected rats are examined. The day of MCT injection is defined as day 0. This survival analysis covers the entire experimental period to day 63.

Hemodynamic Measurements

After the animals are anesthetized with sodium pentobarbital (30 mg/kg, IP), polyethylene catheters are inserted into the RV through the jugular vein and into the carotid artery for hemodynamic measurements. RV systolic pressure (RVSP) is measured with a polygraph system (AP-601G, Nihon Kohden).

Morphometric Analysis of Pulmonary Arteries

After the hemodynamic measurements, lung tissue is prepared for morphometric analysis by using the barium injection method (Cowan K N et al. *Nat Med.* 6:698-702, 2000). All barium-filled arteries of 15 to 50 µm in diameter, which are nonmuscular under normal conditions, are evaluated for muscularization of pulmonary microvessels (Cowan K N et al. *Nat Med.* 6:698-702, 2000). For each artery, the median wall thickness (MWT) is expressed as follows: percent wall thickness=[(medial thickness×2)/external diameter]×100 (Cowan K N et al. *Nat Med.* 6:698-702, 2000).

Results

The survival over the course of treatment from day 0 to day 63 after the MCT administration and the right ventricular hypertrophy, RVSP, MWT at day 21, 28 and 63 after the MCT administration are measured and compared in the compound-treated MCT-exposed rats vs. saline-treated MCT-exposed rats. Improvement in at least one of the above-mentioned endpoints is observed for at least one of the time points.

Example 132

Efficacy of Compounds in Treating LPS-Induced Lung Injury

Protocol

The LPS-induced lung injury model is often used to determine a potential efficacy of therapeutic approaches designed for treatment of COPD. A compound of this invention is administered i.p. at 1-100 mg/kg of body weight one hour prior to LPS exposure. A control group of animals receives i.p. vehicle. BALB/c mice are placed in a clear mass dosing Plexiglas chamber and exposed to aerosolized LPS ranging in dose from 1-100 ug for 25 minutes. Animals are free roaming and allowed to inhale the LPS aerosol. At 4-24 hours following the LPS challenge pulmonary mechanics is assessed or bronchoalveolar lavage is conducted. Pulmonary mechanics is assessed by exposing the animals to increasing doses of methacholine. For the lavage, animals are humanely euthanized followed by a bronchoalveolar lavage (BAL) to evaluate the cytokine concentrations in the bronchoalveolar lavage fluid (BALF).

In Vivo Assessment of Pulmonary Mechanics

The evaluation of airway sensitivity to bronchial constrictors is assessed using a whole body plethysmograph system. Conscious unrestrained mice are placed in the chamber and allowed to acclimate for 10 minutes followed by dose response ranging from 0.01 mg/ml to 50 mg/ml of methacholine dosed by nebulization into the chamber. The plethysmograph system generates a derived numerical value called Penh which is used to indicate bronchial constriction. Each dose of methacholine will last for a 3 minute nebulization period followed by a 3 minutes rest period for a total of 6 minutes of Penh measurement for each of the methacholine doses. Each animal will remain in the chamber for up to 2 hours for analysis.

In Vitro Assessment of Cytokine and Chemokine Levels

Supernatant retained from the bronchoalveolar lavage is analyzed for concentrations of proinflammatory cytokines and chemokines including but not limited to the following: Il-1beta, IL-1alpha, TNF-alpha, TNF-beta, RANTES, IL-6, IL-8, IL1-11, GM-CSF, MIP-1-alpha, MIP-1-beta, MCP1, MCP2, MCP3 and MCP4. The concentrations of these cytokines and chemokines in the BALF samples are determined using commercially available kits.

Results

Penh and cytokines in BALF are measured as described above four hours following the LPS exposure. Improvement in at least one of the above-mentioned endpoints is observed.

Example 133

Treatment of Human Patients Diagnosed with LAM

Patients suffering from LAM are administered a compound of this invention, which is delivered into the lumen of their lung in the amounts ranging from 0.001 to 100 mg; preferably 0.1 to 100 mg. Alternatively, patients suffering from LAM are administered a compound of this invention that is delivered systemically in the amounts ranging from 0.01 to 100 mg/kg of patient's body weight; preferably 0.1 to 100 mg/kg of patient's body weight. After initial dose, additional doses can be administered.

It is observed that the administration of a compound of this invention improves the health status of the patient as measured by improvement in at least one of the following measurable signs, symptoms and other variables clinically relevant to LAM. Such improvements include decreased frequency of pneumothorax, decrease frequency of pulmonary bleeding, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decrease in angiomyolipoma volume, decreased mortality or morbidity, decreased length of hospital stay, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method, amount of epithelial lining fluid, wet to dry lung weight, alveolar fluid clearance or radiographic visualization methods, decrease in the levels of inflammatory cells in the lung or outside of the lung in other anatomical compartments or spaces including systemic circulation, decrease in the amount of pro-inflammatory molecules including cytokines and chemokines in the lung or outside of the lung in other anatomical compartments or spaces including systemic circulation, decreased pathological remodeling of the airway, decrease in patient-reported or physician-observed signs such as difficulty of breathing, or severity of coughing and/or wheezing.

Example 134

Prevention of Acute Lung Injury in an Oleic-Acid Rat Model of ARDS

The aspiration of stomach contents into the lungs during obstetric anesthesia (Am J Obstet Gynecol 1946; 52:191) and aspiration of gastric contents is now recognized as an important risk factor for ARDS (Pepe P E et al. *Am J Surg,* 144: 124-30, 1982; Hudson L D et al. *Am J Respir Crit Care Med,* 151:293-301, 1995; Doyle R L et al. *Am J Respir Crit Care Med,* 152:1818-24, 1995). Oleic acid-induced lung injury is a well established model of ARDS (Dickey B F et al. *Am. J. Pathol.,* 103:376-383, 1981). It is characterized by diffuse interstitial and alveolar edema with focal hemorrhage and vascular congestion, and by interstitial and alveolar infiltration of leukocytes (Beilman G. Lipids 30:817-823, 1995).

Both sexes of Wistar rats are randomly separated into treatment groups: untreated control, oleic acid-treated control, oleic acid plus a compound of this invention, untreated plus a compound of this invention. All oleic acid treated animals receive a single intravenous (i.v.) administration while untreated animals receive a single i.v. administration of saline. Oleic acid and saline are injected into the tail vein under light anesthesia with ketamine. Acute lung injury is induced by intravenous administration of 100 mg/kg of oleic acid (cis-9-octadecanoic acid). Oleic acid is initially diluted in ethanol and saline is added to a final concentration of 25 mg/ml of oleic acid. A compound of this invention is administered at a dose from 1 to 100 mg/kg either orally, intravenously, intraperitoneally, intracheally or intranasally. Animals receive drugs or saline four hours prior to necropsy.

Four hours after the administration of the drugs, the rats are anaesthetized with a high dose of ketamine (80 mg/kg, i.m.), the thorax is opened and blood samples are taken by cardiac puncture for malondialdehyde, myeloperoxidase, 3-nitro-1-tyrosine and nitrite/nitrate analysis (as markers of lung injury). Thereafter, both lungs are harvested. Some pieces of lungs are preserved in formaldehyde solution (10%) for histopathologic evaluation. Haematoxylin-eosin-stained slides are prepared using standard methods. Other lung pieces are used for biochemical examination and Western blotting.

In oleic acid only treated animals, pronounced acute lung damage is observed. The lung tissue is much darker red in the oleic acid group than in the other groups. Furthermore, an increase in congestion, neutrophil infiltration and even derangement of pulmonary architecture is observed under light microscopy. Increases in serum and tissue nitrite/nitrate, 3-nitro tyrosine, myeloperoxidase and malondialdehyde levels are also observed. Western blot analysis indicates that oleic acid administration significantly upregulates the expression of Rho-kinase (ROCK-1 and ROCK-2).

Administration of a compound of this invention causes a significant improvement in at least one of the following parameters: lung histology with score(s) assessing lung tissue damage, inflammation, and edema; gross appearance of the lung including the color of the lung similar to that in the sham group; normalization of serum nitrite/nitrate, myeloperoxidase and malondialdehyde or tissue 3-nitro tyrosine, myeloperoxidase or malondialdehyde levels; or western blot analysis confirming the restorative effect of Compounds of Formula I on expression of ROCK 1 and 2.

Example 135

Attenuation of Microvascular Leak in Rat Model of VILI

Microvascular leak is one of the defining features of the ARDS and VILI. Male Sprague-Dawley rats are anesthetized intraperitoneally with ketamine and diazepam. Rats are ventilated with room air at 85 breaths/minute for 2 hours either with a ventilation (VT) of 7 ml/kg (VT7) or 20 ml/kg (VT20) and zero end expiratory pressure. A group of animals with a VT of 20 ml/kg receives 10 ml/kg of normal saline (NS) to correct hypotension related to large VT (VT20NS). Airway pressure and systemic arterial pressure are monitored. A compound of this invention (1-100 mg/kg) is given intraperitoneally 30 minutes before starting mechanical ventilation.

After 90 minutes of mechanical ventilation, an intravenous injection of 30 mg/kg Evans Blue Dye (EBD) (Sigma Chemical) is given through the internal jugular vein. EBD extravasation into the lung parenchyma as an estimate of protein permeability is quantitated as previously described (Green T P et al. *J Lab Clin Med,* 111:173-183, 1988). EBD leak in the lung is significantly higher in VT20 and VT20NS groups compared with the VT7 group. There is no significant difference in EBD leak between VT20 and VT20NS. After administration of a compound of this invention, an improvement in at least one of the following parameters is observed: EBD leak in the lung is decreased in VT20 (+) Compound of Formula I and/or VT20NS (+) Compound of Formula I groups compared with VT20 and VT20NS groups; and/or lung weight is significantly higher in VT20 and VT20NS groups compared with VT7 and compound of Formula I attenuates the increase in lung weight in the large VT groups.

Example 136

A Randomized Trial of a Compound of this Invention in Patients with ARDS

With the assent of the attending physician, informed consent is obtained from the patient or next of kin as soon as possible after case identification. Physiologic measurements and specimen collection begins at the time of entry into the study. Three days after the patient has met criteria for ARDS or at entry into the study (whichever is later), he/she is randomized to receive a compound of this invention (0.5-50 mg/kg) or placebo, administered by intravenous infusion or directly into the lumen of the lung once daily for 14 days.

The primary endpoint for this study is the duration of mechanical ventilation. Additional important endpoints include changes in the severity of physiologic derangements of respiratory gas exchange, non-respiratory organ failure, and incidence of ventilator-associated pneumonia. Additional assessments designed to determine the mechanism of benefit of a compound of this invention include measures of lung epithelial cell integrity and measures of alveolar macrophage (lung inflammatory cell) function. It is observed that the administration of a compound of this invention improves ARDS by the improvement of any of the primary or secondary endpoints measured in this study.

Example 137

Efficacy of Compounds of this Invention Attenuating Pathophysiologies Relevant to CF Treatment There are currently no animal models of CF lung disease. The examples listed below illustrate the ability of compounds of this invention to affect cellular and physiological processes known to be involved in the pathogenesis of CF lung disease in in vitro assays and in non-CF animal models with relevant pathological alterations of the respiratory system.
Efficacy of Compounds of this Invention in Airway Smooth Muscle Relaxation and Prevention of Airway Hyperreactivity Relevant to CF
Relevance.

The clinical manifestation of CF lung disease includes airway hyperreactivity involving the contraction of airway smooth muscle, and bronchodilators such as those used in the treatment of CF (albuterol, formoterol and salmeterol) have been shown to induce tracheal smooth muscle relaxation (Battram et al, *J Pharmacol Exp Therap* 317:762-770, 2006). Therefore, the properties of compounds of this invention as described in Examples 123, 124 and 127 demonstrate the therapeutic utility of these compounds in treatment of CF lung disease related to airway hyperreactivity and bronchoconstriction.
Efficacy of Compounds of this Invention in Attenuation of CF-Related Pulmonary Hypertension with Right Ventricular Hypertrophy
Relevance.

Advanced CF lung disease often involves pulmonary hypertension and associated right ventricular hypertrophy leading to heart failure (Eckles M and Anderson P. *Semin Respir Crit Care Med* 24:323-30, 2003), and currently marketed therapeutics for hypertensive disorders demonstrate efficacy in norepinephrine pre-contracted pulmonary arteries (Walch et al, *Brit J Pharmacol* 126:859-866, 1999). CF lung disease is also characterized by excessive vascular smooth muscle cell proliferation (Hays S R et al. *Thorax* 60:226, 2005; Eckles M and Anderson P. *Semin Respir Crit Care Med* 24:323-30, 2003). Therefore, the properties of compounds of this invention as described in Examples 125 and 131 demonstrate the therapeutic efficacy of these compounds in treatment of CF lung disease related to pulmonary hypertension and associated right ventricular hypertrophy leading to heart failure.
Efficacy of Compounds of his Invention in Reduction of Pulmonary Inflammation Relevant to CF
Relevance.

CF lung disease is characterized by pulmonary inflammation, airway hyperreactivity, and pulmonary fibrosis, and anti-inflammatory drugs are important therapeutic agents in the treatment of CF (Schmitt-Grohé S and Zielen S. *Paediatr Drugs*. 7(6):353-63, 2005; Elizur A et al. *Chest* 133(2): 489-95, 2008). Airway eosinophil infiltration plays a role in CF pathogenesis (Schmitt-Grohé S and Zielen S. *Paediatr Drugs*. 7(6):353-63, 2005). CF lung disease also involves infiltration of polymorphonuclear leukocytes (Elizur A et al. *Chest* 133(2):489-95, 2008). Therefore, the anti-inflammatory efficacy of compounds of this invention as described in Examples 111, 112, 113 and 128 demonstrate therapeutic utility of these compounds in treatment of CF.

Example 138

Efficacy of Compounds of this Invention in Reduction of Pulmonary Inflammation, Airway Hyperreactivity, Bronchoconstriction, Pulmonary Permeability and Edema Accompanying Bronchiectasis Pulmonary inflammation is a key pathophysiology accompanying bronchiectasis. Therefore, the anti-inflammatory efficacy of compound of this invention as described in Examples 111, 112, 113 and 128 demonstrate therapeutic utility of these compounds in treatment of bronchiectasis. Bronchoconstriction and airway hyperreactivity is a key pathophysiology accompanying bronchiectasis. Therefore, efficacy of compounds of this invention as described in Examples 123, 124 and 127 demonstrates therapeutic utility of these compounds in treatment of bronchiectasis. In addition, the following examples illustrate the efficacy of compounds of this invention in reduction of LPS induced pulmonary permeability in rats and LPS-induced airway wall thickening in mice.
Protocol Model is prepared essentially as in Eutamene et al Eur. Resp. J., 25(5):789-796, 2005. Male Wistar rats are anaesthetized using pentobarbital (60 mg/kg body weight-1 intraperitoneally) and anesthesia is maintained with half of this dose 2 h later. An endotracheal cannula equipped with a small catheter is inserted through a tracheotomy. For experiments using LPS from *P. aeruginosa* or vehicle (sterile 0.9% NaCl), an iso-osmolar solution is prepared, containing 5% bovine serum albumin in phosphate-buffered saline. The solution is filtered through a 0.2-mm filter and 0.5 mCi iodine-125-labelled human serum albumin ([125I] albumin) is added to the bovine serum albumin solution. Then LPS from *P. aeruginosa* (1 mg/rat-1) or vehicle is added to the instillate immediately prior to instillation into the trachea at a constant rate of 10 mL/min-1 for 15 min. Four hours after tracheal infusion of [$^{125}$I]-albumin labeled alveolar instillate plus LPS, radioactivity is measured in three compartments: plasma, lung airspace (via bronchoalveolar lavage (BAL)), and total lung tissue. For the evaluation of pulmonary permeability, rats are pretreated twice daily for 2 days with the compounds of Formula I (first bolus administered i.p. or p.o. at 1-100 mg/kg body weight and successive administrations at 1-100 mg/kg body weight) or vehicle (0.2 mL 10% ethanol). The last administration of kinase inhibitor or vehicle is performed 1 h before intratracheal infusion of LPS from *P. aeruginosa*. Four hours after LPS infusion, measurements of epithelial permeability are performed. Evaluations of airway epithelial barrier (AEB) permeability required measurement of residual [$^{125}$I]-albumin, the airspace protein tracer, in the lung, as well as accumulation of [$^{125}$I]-albumin in the plasma. Four hours after infusion of LPS from *P. aeruginosa*, residual [$^{125}$I]-albumin is measured in BAL fluid, lung tissue (after lavage) and plasma. Plasma [$^{125}$I]-albumin levels are measured in abdominal aorta blood samples. The plasma fraction is determined by multiplying the number of counts obtained by the plasma volume (0.07 body weight (1-haematocrit)). All of these residual counts (BAL fluid, lung tissue and plasma) are expressed as a percentage of the total number of counts of [$^{125}$I]-albumin administered intratracheally (100%).

Results

Intratracheal infusion of LPS from *P. aeruginosa* enhances airway epithelial paracellular permeability to large molecules, and the percentage of [$^{125}$I] collected in lung tissue is significantly increased in LPS-treated rats compared to controls. In contrast, levels of [$^{125}$I] in BAL fluid are decreased in LPS animals compared to controls, confirming the increase in albumin passage from the airspace to lung tissue. Pretreatment with the compounds of this invention reduces the increase in lung epithelial permeability induced by LPS and/or the compounds of this invention restore [$^{125}$I] levels in BAL fluid from LPS-treated rats to values closer to controls.

Example 139

Efficacy of Compounds of this Invention in Reduction of Pulmonary Remodeling Accompanying Bronchiectasis The following example illustrates the efficacy of compounds of this invention in the treatment of bronchiectasis in mouse model of LPS induced airway wall thickening. The model is prepared essentially as in (Vernooy et al., Am. J. Respir. Cell Mol. Biol., 26:152-159, 2002.)

Protocol

Male Swiss mice 12 week old are used. Animals are housed individually in standard laboratory cages and allowed food and water ad libitum throughout the experiments. Mice are repeatedly challenged with LPS twice a week for a period of 12 weeks by intratracheal instillation in an attempt to induce a chronic pulmonary inflammation. The dose of LPS used is approximately 5 µg/instillation/mouse. Sham mice are instilled intratracheally with LPS-free sterile 0.9% NaCl, whereas control mice receive no treatment. Intratracheal instillation is performed by a nonsurgical technique. In brief, mice are anesthetized by intraperitoneal injection of xylazine/ketamine. A volume of 50 µL is instilled intratracheally via cannula, followed by 0.1 ml of air. After intratracheal treatment, the mice are kept in an upright position for 10 min to allow sufficient spreading of the fluid throughout the lungs. The compounds this invention are administered i.p. or p.o. at 1-100 mg/kg body weight daily starting with the first LPS administration into the animals over the course of the 12 weeks.

Airway wall thickening is determined using standard morphometric technique on alpha-SMA stained paraffin section cut from the upper part of the left lung. Conducting airways (width >190 µm) are captured at 20× with a digital camera and the smooth muscle cell area surrounding the airways is quantified by computerized morphometry using the an imaging analysis system. Increased width of the smooth muscle layer is taken as evidence of airway wall thickening. Standard morphometric technique is used to determine the presence of emphysematous changes in the lungs. In brief, H&E stained paraffin sections cut from the upper part of the left lung are used, and 10 randomly selected fields are sampled by projecting a microscopic image of the lung section on a screen with a square reference lattice containing one horizontally and one vertically placed test line. The number of intersections of alveolar walls on the test lines are quantified by computerized morphometry using an imaging analysis system and used to quantify alveolar mean linear intercept (LM, the average distance between alveolar walls). Increased LM is taken as evidence of alveolar enlargement.

Results

Treatment of LPS-exposed animals with compounds of this invention results in reduced airway wall thickening or decreases in LM during at least one of the time-points over the 12-week LPS exposure when compared to LPS-exposed untreated animals over the same time period.

Example 140

Efficacy of Compounds of this Invention in Attenuating Pathophysiologies Relevant to AATD Efficacy of Compounds of this Invention in Airway Smooth Muscle Relaxation and Prevention of Airway Hyperreactivity Relevant to AATD Relevance.

The clinical manifestation of AATD lung disease includes airway hyperreactivity involving the contraction of airway smooth muscle, and bronchodilators such as those used in the treatment of AATD (formoterol and salmeterol) have been shown to induce tracheal smooth muscle relaxation (Battram et al, *J Pharmacol Exp Therap* 317:762-770, 2006). Therefore, the properties of compounds of this invention as described in Examples 123, 124 and 127 demonstrate the therapeutic utility of these compounds in treatment of AATD lung disease related to airway hyperreactivity and bronchoconstriction.

Efficacy of Compounds of this Invention in Reduction of Pulmonary Inflammation Relevant to AATD Relevance.

AATD lung disease involves pulmonary inflammation, airway hyperreactivity, and pulmonary fibrosis, and anti-inflammatory drugs are important therapeutic agents in the treatment of AATD. Therefore, the anti-inflammatory efficacy of compounds of this invention as described in Examples 111, 112, 113 and 128 demonstrate therapeutic utility of these compounds in treatment of AATD.

Example 141

Efficacy of Compounds of this Invention in an Animal Model of Rhinitis

Nasal congestion due to inflammation and tissue edema is one of the key pathophysiologies defining rhinitis. In the following dog model of ragweed-induced rhinitis, nasal congestion is measured via acoustic rhinometry and nasal resistance.

Protocol

Newborn dogs receive an intraperitoneal injection containing 200 µg of ragweed extract in 0.5 ml of 0.9% saline mixed with 30 mg of aluminum hydroxide within 24 hours of birth. (Becker et. al. *J Appl Physiol.* 1989. 66:2691-2697; Yeates et. al. *Proc Assoc Am Physicians.* 1997, 109: 440-52). Booster injections are repeated weekly for 6 weeks and biweekly until 16 weeks of age. Sensitization to the allergen is confirmed by analysis of ragweed-specific IgE levels in the serum of the animals. For the experiment, fasted dogs are anesthetized and intubated. A nasal cathether is placed in each nostril to facilitate measurements of airway resistance. Nasal congestion in ragweed-sensitized dogs is induced by local, acute administration of histamine as the challenging allergen. Acoustic rhinometry and nasal airway resistance are measured between 4 and 24 hr post histamine administration to evaluate benefit of formulated compounds (Tiniakov et al. *J Appl Physiol* 2003. 94: 1821-1828).

Compounds of this invention are dosed via bilateral intranasal administration at 30-60 minutes before histamine challenge at a dose volume of 100 µL per nostril at a concentration range of 10 µM to 10 mM range. A control group receives bilateral nasal administration of vehicle (placebo) at the same administration volume as active.

Acoustic Rhinometry

Nasal resistance can be measured in both the right and left nasal passages by using an anterior constant flow nasal rhinomanometry device. Changes in the geometry of the nasal cavity can be estimated using Acoustic Rhinometry System. The acoustic wave tube is fitted with a handmade plastic tip designed to match to the shape of the dog's nostrils. Acoustic measurements of the geometric parameters of the right nasal passage are performed at various times after allergen or constricting agent is applied. Volume of the right nasal airway and cross-sectional areas of right nasal cavity at the levels of a nasal valve, anterior and posterior regions of maxilloturbinates, and the moturbinates can be calculated using acoustic rhinometry.

Measurement of Nasal Resistance

Airway resistance can be measured in combination with acoustic rhinometry. Nasal airways resistance is determined by measuring the air pressure required to achieve a constant predetermined flow through the nasal passage. This constant airflow is delivered to the nasal passage through a nasal catheter coupled to a pressure transducer. The nasal catheter is snugly placed into the nostril and the cuff inflated to form a seal. Nasal resistance is defined as the pressure differential between the input air pressure and atmospheric pressure divided by the airflow. In these studies, nasal resistance can be measured in the left nasal airway and geometric parameters of the right nasal airway are measured with the acoustic rhinometer, simultaneously. To do this, allergen or constricting agent is locally delivered to both nasal passages.

Results

Between 4 and 24 hours following nasal administration of histamine, animals are evaluated for acoustic rhinometry and nasal resistance. Improvement in either acoustic rhinometry or nasal resistance is observed between 4-hr to 24-hr in animals dosed with a compound of this invention when compared to animals that receive placebo.

Example 142

Efficacy of Compounds of this Invention in Attenuating Pathophysiologies Associated with Rhinosinusitis The following example illustrates the efficacy of compounds of this invention in treatment of inflammation in mouse model of sinusitis. The model is prepared essentially as in Blair, C., et al. J Allergy Clin. Immunol, 108(3):424-9, 2001.

Protocol

Pathogen-free 6 to 8-week-old BALB/c mice of either sex are used. Each group of animals is kept isolated from the other groups in a biohazard containment facility. All mice use is in accordance with National Institutes of Health Laboratory Animal Care Guidelines.

A group of animals is pretreated with a compound of this invention via intraperitoneal administration twice daily at 1-100 mg/kg of body weight on Day 1-3 and one hour prior to inoculation on day 4 while the control group is dosed with vehicle. S. pneumoniae (ATCC49619) is used for induction of acute sinusitis. The strain is antigenically similar to type 19 S. pneumoniae, the most common strain cultured from human sinuses. The S. pneumoniae is grown on blood agar plates, and colonies are suspended in sterile saline solution immediately before inoculation of the mice. The mice are anesthetized with intraperitoneal injection of ketamine/xylazine, and sufficient amount of the S. pneumoniae suspension is placed in each naris to induce infection. The mice are killed on day 5 after infection; prior experiments have shown peak infection in the sinuses at that time point.

On the day of sacrifice, the mice are sedated with a respiratory-failure dose of pentobarbital sodium (Nembutal) at 120 mg/kg. The animal is transcardially (through the right atrium) perfused with lactated Ringer's solution; this is followed by perfusion with a solution of 4% formaldehyde and 0.5% glutaraldehyde in 0.1 mmol/L of phosphate buffer. Next, the animal is decapitated and sections of the nasal passages are cut at a thickness of 8 μm, mounted on glass slides, and stained with Luna stain or hematoxylinand eosin.

Light Microscopy and Enumeration of Inflammatory Cells

Three anatomically similar sections are chosen from each mouse for analysis: an anterior section at the level of the maxillary sinuses, a middle section (more posterior and sampling the end of the maxillary sinuses and the beginning of the ethmoidal turbinals), and a third posterior section. Individual sections are analyzed, after masking, by use of a computer-aided light microscope in conjunction with reconstruction software. To quantify the degree of inflammation, we use 400× magnification and trace the total sinus cavity area and the area of the sinus occupied by neutrophil clusters; this allows us to calculate the percent of the sinus cavity filled with neutrophil clusters. Mucosa adjacent to neutrophil clusters is also traced and examined for polymorphonuclear cells, allowing us to report the number of cells per square millimeter. A random sampling of 4 mucosal areas from each of the 3 sections from each mouse is evaluated for the parameters described above, and the average of these measurements is computed for each mouse and used for statistical analysis. Eosinophils and mononuclear cells, as well as eosinophils in the lung, are counted in similar manner.

Results

The resulting inflammatory cell counts demonstrate that treatment with a compound of this invention attenuates the inflammatory cell numbers identified in the nasal passage ways of mice with experimental sinusitis when compared to the non-treated animals with experimental sinusitis.

Example 143

Efficacy of Compounds of this Invention in Attenuating Pathophysiologies Associated with OB/BOOP Due to Lung Transplantation or HSCT Efficacy of Compounds of this Invention in Airway Smooth Muscle Relaxation and Prevention of Airway Hyperreactivity Relevant to OB/BOOP Due to Lung Transplantation or HSCT Relevance.

The clinical manifestation of OB/BOOP in the lung includes airflow limitation in the airway involving inflammation and the contraction of airway smooth muscle, Therefore, the properties of compounds of this invention as described in Examples 123, 124 and 127 demonstrate the therapeutic utility of these compounds in treatment of OB/BOOP related to airway hyperreactivity and bronchoconstriction.

Efficacy of Compounds of this Invention in Reduction of Pulmonary Inflammation Relevant to OB/BOOP Due to Lung Transplantation or HSCT Relevance.

OB/BOOP involves pulmonary inflammation, airway hyperreactivity, and pulmonary fibrosis, and anti-inflammatory drugs are important therapeutic agents in the treatment of OB/BOOP. Therefore, the anti-inflammatory efficacy of compounds of this invention as described in Examples 111, 112, 113 and 128 demonstrate therapeutic utility of these compounds in treatment of OB/BOOP.

Efficacy of Compounds of this Invention in an Animal Model of BOOP

The following example illustrates the efficacy of compounds of this invention in treatment of BOOP in an animal model of virally induced intraluminal fibrosis. The model is prepared essentially as in Majesky et al., *Am J Pathol,* 163: 1467-1479, 2003.

Protocol

Four- to 5-week-old female CBA/J mice are lightly anesthetized and infected by the intranasal (i.n.) application of $1 \times 10^6$ PFU of reovirus 1/L in 30 ml (15 ml in each nostril) in sterile saline on day 0. Control animals are inoculated with sterile saline alone. A compound of this invention is administered to mice beginning on day 5 post-reovirus 1/L infection and given daily until the completion of the time-course. As a control standard compound, 10 mg/kg of methylprednisolone is administered i.p. to mice beginning on day 5 post-reovirus 1/L infection and given daily until the completion of the time-course. On days 7, 10, and 14 BAL fluid is taken for measurement of cytokines. On day 14 or day 21, animals are sacrificed for histological evaluation of the lung.

Cytokine Determination in BAL Fluid

BAL is performed in situ by injecting and withdrawing a 0.5 ml aliquot of Hank's balanced salt solution (HBSS) twice through an intubation needle (21 gauge). BAL fluid is analyzed for mouse IFN-γ and MCP-1 using commercially available ELISA kits.

Histology

On day 14 or 21, lungs are inflated in situ with 10% neutral buffered formalin (0.5 mls) by intratracheal (i.t.) intubation, removed, and suspended in an additional 10% neutral buffered formalin overnight before being embedded in paraffin H&E stain and Mason's trichrome stain, which are used to visualize collagen deposition, are performed on 4-μm sections. Inflammatory infiltration with the development of follicular bronchiolitis (FB), which is defined as a mononuclear cell infiltrate that condenses into prominent peribronchiolar lymphoid accumulations, is blindly evaluated. FB is scored on a scale of 0 to 3: 0, normal; 1, mild (less than 4 follicles per lobe); 2, moderate (between 5 and 8 follicles per lobe); 3, severe (greater than 8 follicles per lobe). Fibrosis is scored on a scale of 0 to 4: 0, normal; 1, mild; 2, moderate; 3, severe; 4, very severe.

OH-Proline Assay

On day 14 or 21, OH-proline contents of the lungs are measured objectively to estimate lung fibrosis (Green G D et al. *Anal Biochem.* 201:265-269, 1992). The right lungs of each mouse are dissected free from major bronchi, and the wet weights are measured. They are hydrolyzed in 500 ml of 12 N hydrochloric acid and in the same aliquot of distilled water at 110 C. 20 h, in dry block. After the resultant hydrolysate is neutralized with sodium hydroxide, a 100-ml supernatant is mixed in 1.5 ml of 0.3 N lithium hydroxide solution. The OH-proline content is determined by high-performance liquid chromatography and expressed as micrograms per right lung.

Results

On the indicated day, the fibrotic changes in the lung, the hydroxyproline content in the lung, and the cytokine content in the BAL fluid are measured and compared in the compound-treated mice vs. saline-treated mice. Administration of a compound of this invention results in the improvement in at least one of the above-mentioned endpoints that is equal to or greater than the improvement seen with methylprednisolone.

Example 144

Efficacy of Compounds of this Invention in Attenuating Pathophysiologies Relevant to Non-IPF IIP Efficacy of Compounds of this Invention in Airway Smooth Muscle Relaxation and Prevention of Airway Hyperreactivity Relevant to Non-IPF IIP Relevance.

The clinical manifestation of non-IPF IIP includes airflow limitation in the airway involving inflammation and the contraction of airway smooth muscle, Therefore, the properties of compounds of this invention as described in Examples 123, 124 and 127 demonstrate the therapeutic utility of these compounds in treatment of non-IPF IIP related to airway hyperreactivity and bronchoconstriction.

Efficacy of Compounds of this Invention in Reduction of Pulmonary Inflammation Relevant to Non-IPF IIP Relevance.

Non-IPF IIP involves pulmonary inflammation, airway hyperreactivity, and pulmonary fibrosis, and anti-inflammatory drugs are important therapeutic agents in the treatment of non-IPF IIP. Therefore, the anti-inflammatory efficacy of compounds of this invention as described in Examples 111, 112, 113 and 128 demonstrate therapeutic utility of these compounds in treatment of non-IPF IIP.

Example 145

Efficacy of Compounds of this Invention in Attenuating Pathophysiologies Relevant to the ILD Other than IPF, Non-IPF IIPs and OB/BOOP Efficacy of Compounds of this Invention in Airway Smooth Muscle Relaxation and Prevention of Airway Hyperreactivity Relevant to ILD Other than IPF, Non-IPF IIPs and OB/BOOP Relevance.

The clinical manifestation of ILD other than IPF, non-IPF IIPs and OB/BOOP in the lung includes airflow limitation in the airway involving inflammation and the contraction of airway smooth muscle, Therefore, the properties of compounds of this invention as described in Examples 123, 124 and 127 demonstrate the therapeutic utility of these compounds in treatment of ILD other than IPF, non-IPF IIPs and OB/BOOP related to airway hyperreactivity and bronchoconstriction.

Efficacy of Compounds of this Invention in Reduction of Pulmonary Inflammation Relevant to ILD Other than IPF, Non-IPF IIPs and OB/BOOP Relevance.

ILD other than IPF, non-IPF IIPs and OB/BOOP involves pulmonary inflammation, airway hyperreactivity, and pulmonary fibrosis, and anti-inflammatory drugs are important therapeutic agents in the treatment of ILD other than IPF, non-IPF IIPs and OB/BOOP. Therefore, the anti-inflammatory efficacy of compounds of this invention as described in Examples 111, 112, 113 and 128 demonstrate therapeutic utility of these compounds in treatment of ILD other than IPF, non-IPF IIPs and OB/BOOP.

Example 146

Ocular Pharmacokinetic Assay

Intraocular fluid (aqueous humor) is collected from New Zealand White rabbits to determine corneal and anterior chamber pharmacokinetics of formulations containing test compounds. Each animal is dosed bilaterally with 2×10 μl of 25 mM of each test compound (in 10 mM acetate buffered saline, 0.01% benzalkonium chloride, 0.05% EDTA, pH 4.5) or with vehicle. During instillation, the upper and lower eyelids are immobilized and the compound is administered to the superior aspect of the globe allowing it to flow across the ocular surface. Following instillation, blinking is prevented for 30 seconds. Aqueous humor is collected from 30 minutes to 8 hours following topical instillation using a 30-gauge needle inserted proximal to the corneal scleral limbus. Subsequently 30 μl of aqueous humor is aspirated using a 300 μl syringe. Aqueous humor samples are assayed for the concentration of the test compound using an LC/MS/MS assay system. All experiments are conducted in accordance with the ARVO Statement for the Use of Animals in Ophthalmic and Vision Research and in compliance with National Institutes of Health. The results of observed aqueous humor concentrations of the test compounds at 0.5, 2, and 4 hours after instillation are determined.

This pharmacokinetic assay shows that the compounds are able to penetrate the eye when dosed topically and achieve concentrations in the aqueous humor adequate to provide substantial Rho kinase inhibition at the sight of action, that is, concentrations at or above the Rho kinase $IC_{50}$ of the compound in question. Further, it shows that compounds can show different pharmacokinetic profiles on topical ocular dosing, with some compounds showing a more prolonged presence, while others penetrate rapidly into the eye and are quickly cleared from the aqueous humor.

Example 147

Rodent Pharmacokinetic Analyses of ROCK Inhibitors

Plasma (EDTA K2 anticoagulant) is collected from male, cannulated, CD Sprague Dawley rats to determine the pharmacokinetics of formulations containing compound inhibitors of Rho kinase. Each animal is dosed orally with test compound at 20-30 μmol/kg. Blood is collected at 0.25, 0.5, 1, 2, and 4 hours. At 4 hours, animals are sacrificed according to IACUC protocol and lungs are homogenized in Matrix A lysing tubes using a FastPrep 24 tissue and cell homogenizer (MP Biomedicals, Solon, Ohio). Both plasma samples and lung extracts are assayed for compound concentrations using an on-line, solid phase extraction LC/MS/MS system. The actual lung tissue concentrations of each compound is extrapolated from the lung and plasma concentrations.

The results of these quantitative analyses will enable the selection of compounds for additional studies based on desirable pharmacokinetic profiles and preferential distribution in the target organ (lungs). Characterization of the pharmacokinetic properties and distribution of these Rho kinase inhibitors is an essential part of the selection of compounds for development as either oral or inhaled products.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:
1. A compound of Formula I:

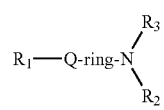

Formula I wherein:

$R_1$ is substituted aryl;

Q is $(CR_4R_5)_vC(=O)$, $(CR_4R_5)_vSO_2$, or $(CR_4R_5)_v$, in which $C(=O)$ and $SO_2$ are connected to ring;

v is 0, 1, 2, or 3;

$R_2$ is selected from the following heteroaryl systems, optionally substituted:

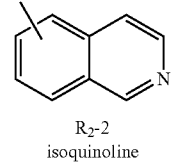

$R_2$-2
isoquinoline ring is selected from the following bridged bicyclic systems:

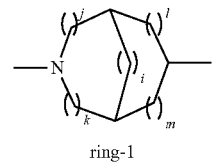

ring-1 in which N of ring is connected to Q, and the other line is connected to $NR_2R_3$;

i and n are independently 1, 2, or 3;

j, k, l, and m are independently 0, 1, or 2;

the ring is optionally substituted by alkyl, cycloalkyl, aryl, heteroaryl, heterocycle, halo, oxo, $OR_6$, $NR_6R_7$, or $SR_6$;

$R_3$-$R_7$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, optionally substituted;

when ring is ring-1, then 1≤j+k+l+m≤6; when ring is ring-2, then 1≤j+k+l+n≤6, and when ring is ring-3, then 2≤j+k+n≤6.

2. The Compound according to claim 1, wherein the ring is selected from one of the following rings:

1

-continued

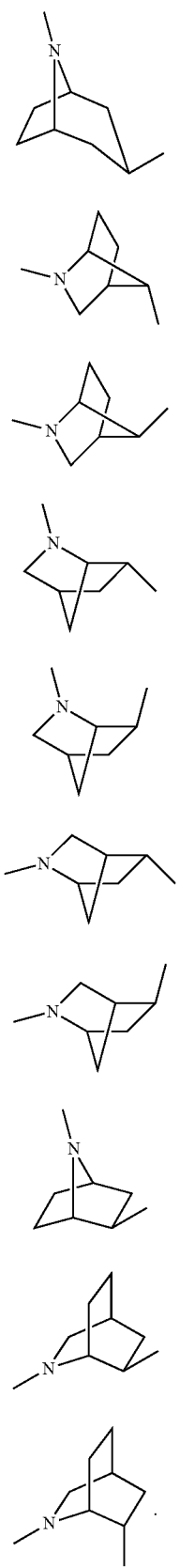

3. The Compound according to claim 2, wherein the ring is

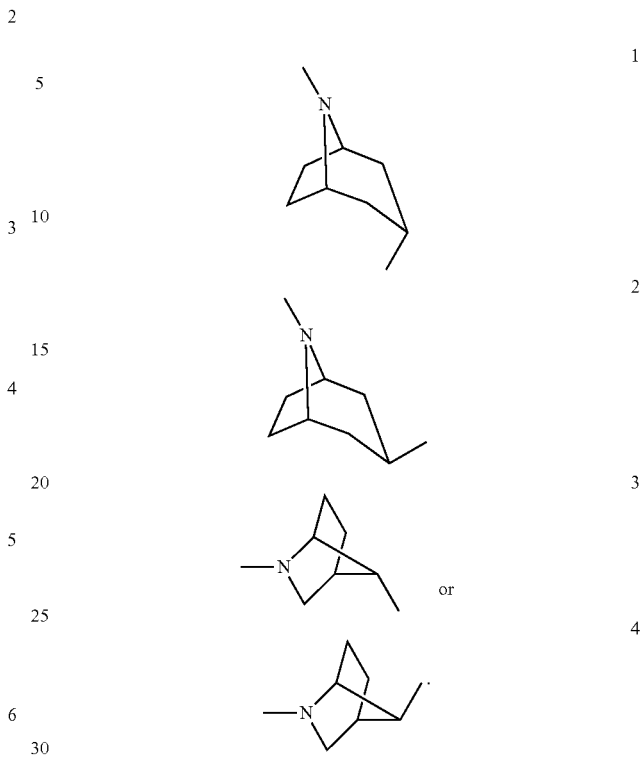

4. The Compound according to claim 1, wherein the ring is ring-1, j=k=l=m=0 or 1, and i=1 or 2.

5. The Compound according to claim 1, wherein $Q=(CR_4R_5)_v$, and v=1-3.

6. The compound according to claim 1, wherein $R_1$ has 1-3 substituents each independently in the form of Y—Z, in which Z is attached to Q and Y is a substituent on Z;

Y is independently selected from the group consisting of: H, alkyl, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, and $NR_8C(=O)NR_9R_{10}$;

Z is independently selected from the group consisting of: alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, and absent, with the proviso that if Z is absent, then Y is not H;

$R_8$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; and $R_8$-$R_{10}$ are optionally substituted by halogen, $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}(=O)R_{12}$, $NR_{11}C(=O)R_{12}$, $OC(=O)NR_{11}R_{12}$, or $NR_{11}C(=O)NR_{12}R_{13}$.

7. The compound according to claim 6, wherein Y is H, alkyl, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$.

8. The compound according to claim 7, wherein Y is alkyl, halogen, $OR_8$, or $NR_8SO_2R_9$.

9. The compound according to claim 6, wherein Z is alkyl, alkenyl, alkynyl, cycloalkyl, cycloalkenyl, cycloalkylalkyl, or is absent.

10. The compound according to claim 6, wherein $R_8$ is H, alkyl, arylalkyl, cycloalkyl, cycloalkylalkyl, or heterocycle, optionally substituted with halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and $R_9$-$R_{13}$ are H or alkyl.

11. The compound according to claim 1, which is N-((1RS,3rs,5SR)-8-(4-methylbenzyl)-8-azabicyclo[3.2.1]octan-3-yl)isoquinolin-5-amine; 2-(5-(((1RS,3rs,5SR)-3-(isoquinolin-5-ylamino)-8-azabicyclo[3.2.1]octan-8-yl)methyl)-2-methylphenoxy)ethanol; N-((1RS,3sr,5SR)-8-(4-methylbenzyl)-8-azabicyclo[3.2.1]octan-3-yl)isoquinolin-5-amine; 2-(5-(((1RS,3sr,5SR)-3-(isoquinolin-5-ylamino)-8-azabicyclo[3.2.1]octan-8-yl)methyl)-2-methylphenoxy)ethanol; N-((1SR,4SR,7RS)-2-(4-methylbenzyl)-2-azabicyclo[2.2.1]heptan-7-yl)isoquinolin-5-amine; 2-(5-(((1SR,4SR,7RS)-7-(isoquinolin-5-ylamino)-2-azabicyclo[2.2.1]heptan-2-yl)methyl)-2-methylphenoxy)ethanol; N-((1SR,4SR,7SR)-2-(4-methylbenzyl)-2-azabicyclo[2.2.1]heptan-7-yl)isoquinolin-5-amine; N-(5-(((1SR,4SR,7SR)-7-(isoquinolin-5-ylamino)-2-azabicyclo[2.2.1]heptan-2-yl)methyl)-2-methylphenyl)methanesulfonamide; N-((1SR,4SR,7SR)-2-(3-fluorobenzyl)-2-azabicyclo[2.2.1]heptan-7-yl)isoquinolin-5-amine; N-((1SR,4SR,6SR)-2-(4-methylbenzyl)-2-azabicyclo[2.2.1]heptan-6-yl)isoquinolin-5-amine; N-(3-(((1SR,4SR,6SR)-6-(isoquinolin-5-ylamino)-2-azabicyclo[2.2.1]heptan-2-yl)methyl)phenyl)methanesulfonamide; N-((1SR,4SR,6RS)-2-(4-methylbenzyl)-2-azabicyclo[2.2.1]heptan-6-yl)isoquinolin-5-amine; 2-(3-(((1SR,4SR,6RS)-6-(isoquinolin-5-ylamino)-2-azabicyclo[2.2.1]heptan-2-yl)methyl)phenoxy)ethanol; N-((1SR,4SR,6RS)-2-(4-methoxybenzyl)-2-azabicyclo[2.2.1]heptan-6-yl) isoquinolin-5-amine; N-((1RS,4RS,5SR)-2-(4-methylbenzyl)-2-azabicyclo[2.2.1]heptan-5-yl)isoquinolin-5-amine; N-(5-(((1RS,4RS,5SR)-5-(isoquinolin-5-ylamino)-2-azabicyclo[2.2.1]heptan-2-yl)methyl)-2-methylphenyl)methanesulfonamide; N-((1RS,4RS,5RS)-2-(4-methylbenzyl)-2-azabicyclo[2.2.1]heptan-5-yl)isoquinolin-5-amine; 2-(5-(((1RS,4RS,5RS)-5-(isoquinolin-5-ylamino)-2-azabicyclo[2.2.1]heptan-2-yl)methyl)-2-methylphenoxy)ethanol; N-((1RS,4RS,5RS)-2-(4-fluorobenzyl)-2-azabicyclo[2.2.1]heptan-5-yl)isoquinolin-5-amine; N-((1SR,2RS,4RS)-7-(4-methylbenzyl)-7-azabicyclo[2.2.1]heptan-2-yl)isoquinolin-5-amine; 2-(5-(((1SR,2RS,4RS)-2-(isoquinolin-5-ylamino)-7-azabicyclo[2.2.1]heptan-7-yl)methyl)-2-methylphenoxy)ethanol; (1RS,4SR,6RS)—N-(isoquinolin-5-yl)-2-(4-methylbenzyl)-2-azabicyclo[2.2.2]octan-6-amine; N-(5-(((1RS,4SR,6RS)-6-(isoquinolin-5-ylamino)-2-azabicyclo[2.2.2]octan-2-yl)methyl)-2-methylphenyl)methanesulfonamide; (1RS,4SR,6RS)-2-(4-chlorobenzyl)-N-(isoquinolin-5-yl)-2-azabicyclo[2.2.2]octan-6-amine; (1RS,4SR,6SR)—N-(isoquinolin-5-yl)-2-(4-methylbenzyl)-2-azabicyclo[2.2.2]octan-6-amine; N-(5-(((1RS,4SR,6SR)-6-(isoquinolin-5-ylamino)-2-azabicyclo[2.2.2]octan-2-yl)methyl)-2-methylphenyl)methanesulfonamide.

12. The compound according to claim 11, which is N-((1RS,3rs,5SR)-8-(4-methylbenzyl)-8-azabicyclo[3.2.1]octan-3-yl)isoquinolin-5-amine; 2-(5-(R1RS,3rs,5SR)-3-(isoquinolin-5-ylamino)-8-azabicyclo[3.2.1]octan-8-yl)methyl)-2-methylphenoxy)ethanol; N-((1RS,3sr,5SR)-8-(4-methylbenzyl)-8-azabicyclo[3.2.1]octan-3-yl)isoquinolin-5-amine; 2-(5-(((1RS,3sr,5SR)-3-(isoquinolin-5-ylamino)-8-azabicyclo[3.2.1]octan-8-yl)methyl)-2-methylphenoxy)ethanol; N-((1SR,4SR,7RS)-2-(4-methylbenzyl)-2-azabicyclo[2.2.1]heptan-7-yl)isoquinolin-5-amine; or 2-(5-(((1SR,4SR,7RS)-7-(isoquinolin-5-ylamino)-2-azabicyclo[2.2.1]heptan-2-yl)methyl)-2-methylphenoxy)ethanol.

13. A pharmaceutical composition comprising the compound of claim 1 and a pharmaceutically acceptable carrier.

\* \* \* \* \*